(12) United States Patent
Nguyen et al.

(10) Patent No.: US 11,911,280 B2
(45) Date of Patent: Feb. 27, 2024

(54) KNEE PROSTHESIS

(71) Applicant: Optimotion Implants LLC, Orlando, FL (US)

(72) Inventors: Vuong Binh Nguyen, Windermere, FL (US); Andrew Rynearson, Winter Springs, FL (US)

(73) Assignee: OPTIMOTION IMPLANTS LLC, Orlando, FL (US)

( * ) Notice: Subject to any disclaimer, the term of this patent is extended or adjusted under 35 U.S.C. 154(b) by 88 days.

(21) Appl. No.: 17/581,941

(22) Filed: Jan. 23, 2022

(65) Prior Publication Data
US 2023/0233331 A1 Jul. 27, 2023

(51) Int. Cl.
*A61F 2/38* (2006.01)
*A61F 2/30* (2006.01)

(52) U.S. Cl.
CPC ............ *A61F 2/3859* (2013.01); *A61F 2/389* (2013.01); *A61F 2/3836* (2013.01); *A61F 2002/30621* (2013.01); *A61F 2002/3863* (2013.01)

(58) Field of Classification Search
CPC ....... A61F 2/389; A61F 2/3859; A61F 2/3836
See application file for complete search history.

(56) References Cited

U.S. PATENT DOCUMENTS

| | | | |
|---|---|---|---|
| 5,059,216 | A | 10/1991 | Winters |
| 5,071,438 | A | 12/1991 | Jones et al. |
| 5,219,362 | A | 6/1993 | Tuke et al. |
| 5,344,460 | A | 9/1994 | Turanyi et al. |
| 5,413,604 | A | 5/1995 | Hodge |
| 5,964,808 | A | 10/1999 | Blaha et al. |
| 7,740,662 | B2 | 6/2010 | Barnett et al. |
| 8,480,754 | B2 | 7/2013 | Bojarski et al. |
| 8,690,954 | B2 | 4/2014 | Parisi et al. |

(Continued)

FOREIGN PATENT DOCUMENTS

| | | |
|---|---|---|
| CN | 105796212 A | 7/2016 |
| CN | 111184598 A2 | 5/2020 |
| WO | 2021149000 A1 | 7/2021 |

OTHER PUBLICATIONS

Palanisami et al., "Tibial bowing and tibial component placement in primary total knee arthroplasty in valgus knees: Are we overlooking?", Journal of Orthopaedic Surgery, 27(3) 1-9 (Jul. 2019).

*Primary Examiner* — Jason-Dennis N Stewart
(74) *Attorney, Agent, or Firm* — David Meibos; Maywood IP Law

(57) ABSTRACT

A knee joint prosthesis system for implantation in a first knee joint of a patient. The first knee joint has a condition. The knee joint prosthesis system includes a tibial baseplate component, a femoral component having a femoral articulation surface, and a tibial insert. The tibial insert includes a tibial articulation surface configured to articulate with the femoral articulation surface. The tibial articulation surface includes a medial tibial compartment asymmetrical to a lateral tibial compartment. The tibial articulation surface is shaped to cooperate with the femoral articulation surface to adapt kinematics of the first knee joint having the condition and the tibial articulation surface is also suitable for implantation in a second knee joint on a second side, the second knee joint lacking the condition.

21 Claims, 45 Drawing Sheets

(56) References Cited

U.S. PATENT DOCUMENTS

| | | |
|---|---|---|
| 9,011,547 B2 | 4/2015 | Auger et al. |
| 9,839,520 B2 | 12/2017 | Mizuguchi |
| 10,470,889 B2 | 11/2019 | Wentorf et al. |
| 11,382,757 B1 * | 7/2022 | Hajizadeh ............. A61F 2/3859 |
| 2004/0204766 A1 | 10/2004 | Siebel |
| 2009/0259314 A1 | 10/2009 | Linder-Ganz et al. |
| 2012/0197409 A1 | 8/2012 | McKinnon et al. |
| 2014/0296992 A1 | 10/2014 | Samuelson et al. |
| 2018/0140232 A1 | 5/2018 | Fleig et al. |
| 2020/0085583 A1 | 3/2020 | Hodge |

* cited by examiner

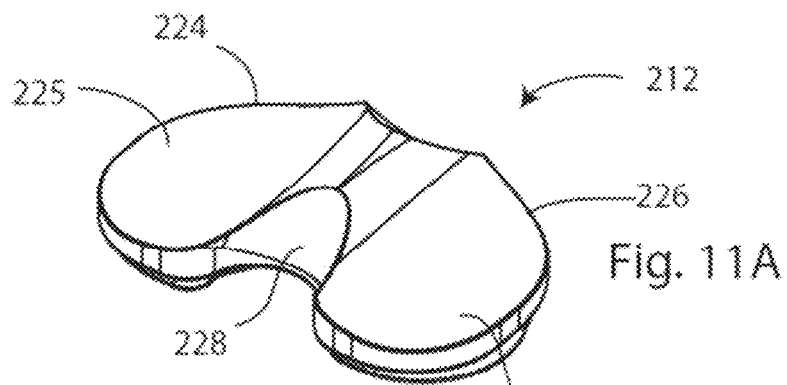
Fig. 11A
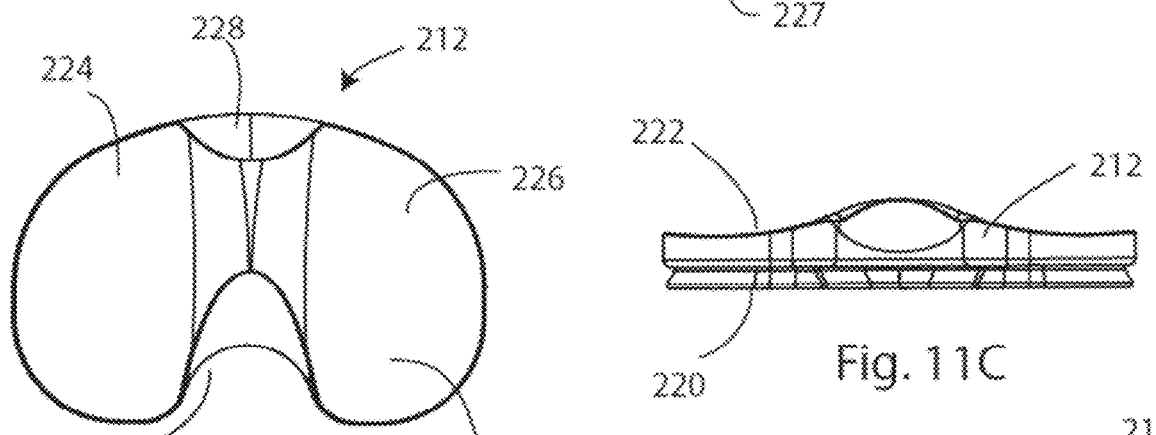
Fig. 11B
Fig. 11C
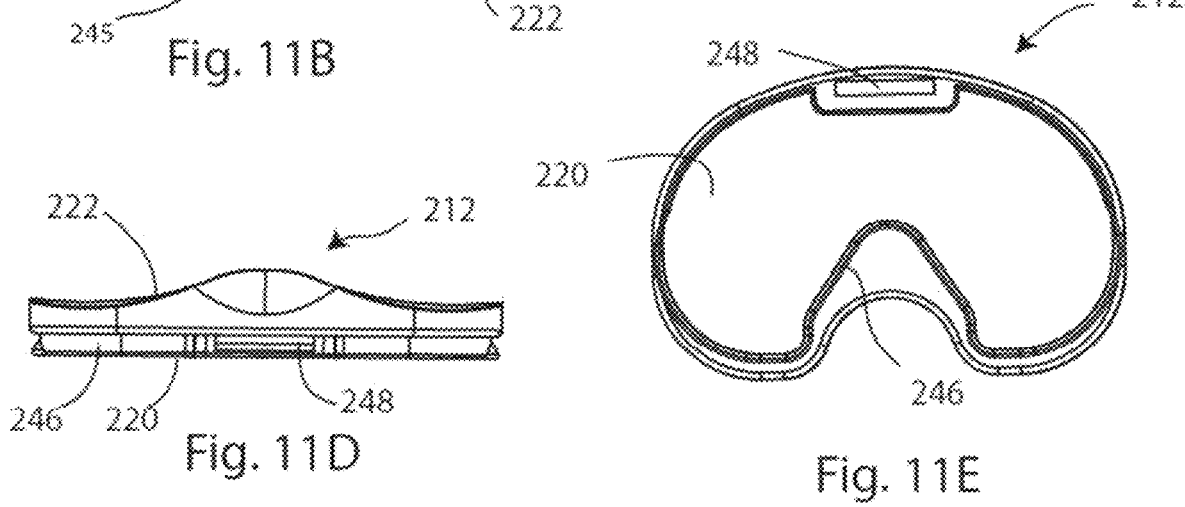
Fig. 11D
Fig. 11E

|  | Cruciate Retaining Insert | Posterior Stabilizing Insert | Constrained Condylar Knee Insert |
|---|---|---|---|
| Cruciate Retaining Femoral Component | X | X | X |
| Posterior Stabilizing Femoral Component | X | X | X |

Fig. 13

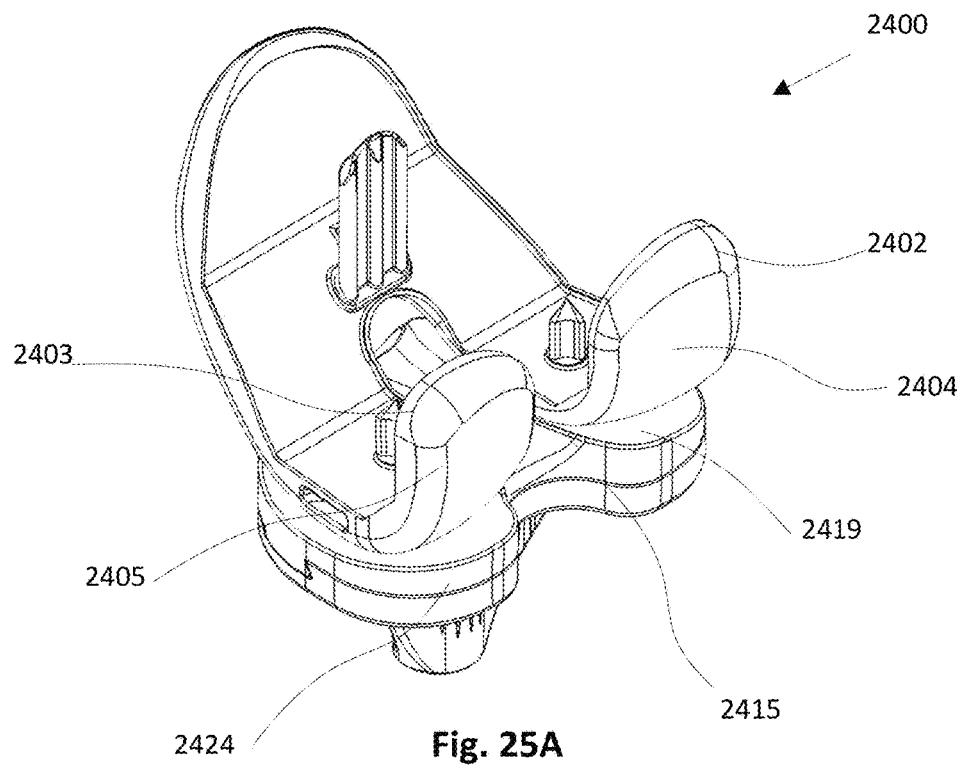
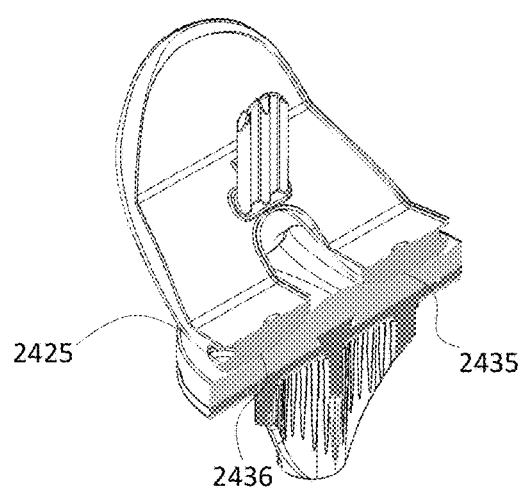
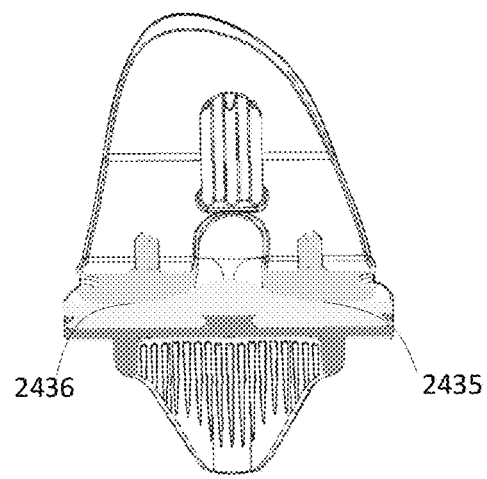
Fig. 25A
Fig. 25B
Fig. 25C

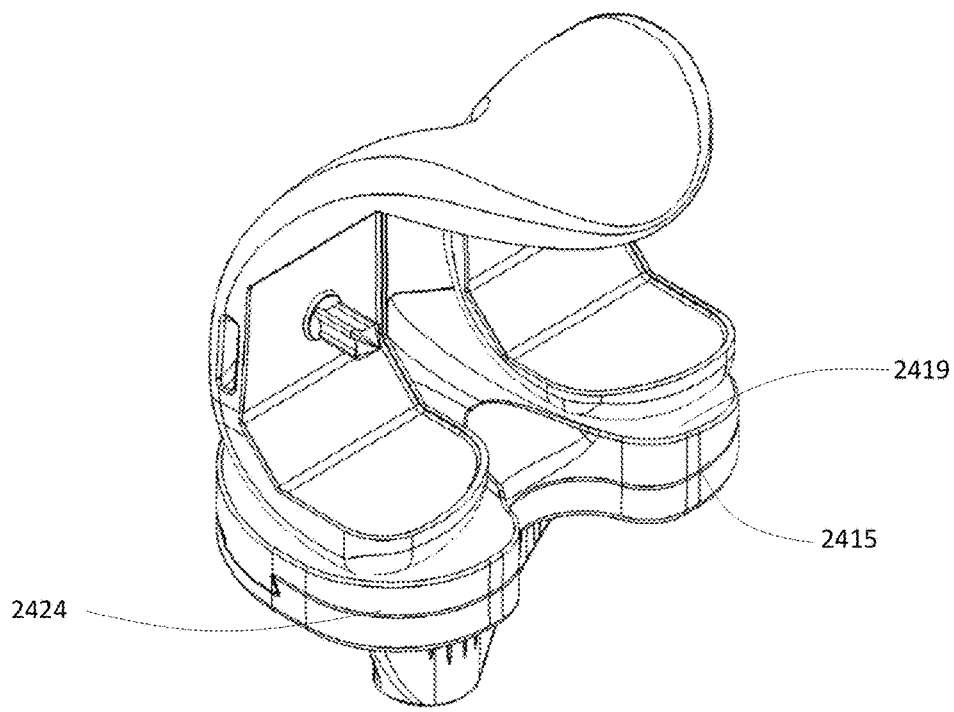
Fig. 27A
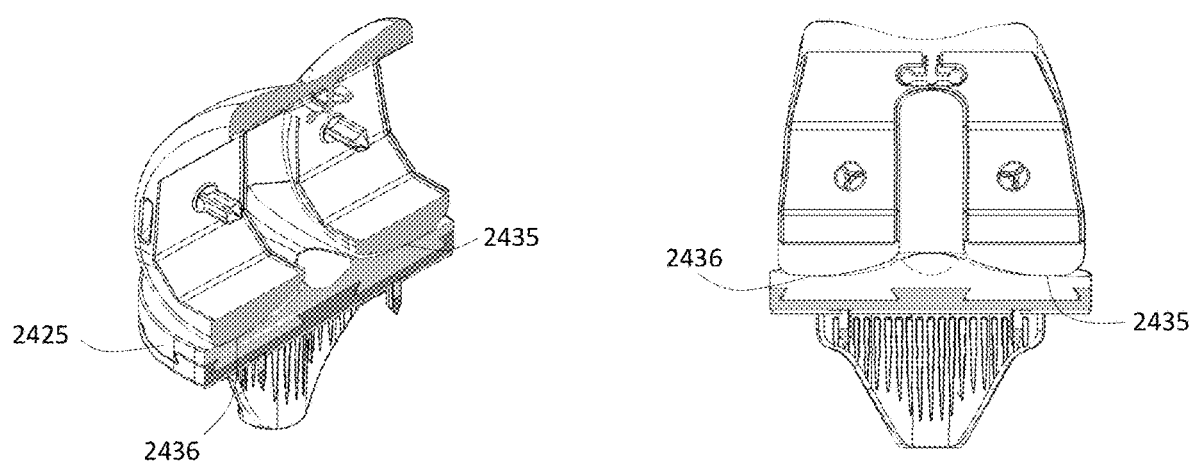
Fig. 27B
Fig. 27C

KNEE PROSTHESIS

TECHNICAL FIELD

The present disclosure relates to surgical devices, systems, instruments, and methods. More specifically, the present disclosure relates to orthopedic knee replacement surgical devices, instruments, systems, and methods.

BACKGROUND

A number of knee replacement options exist which may be implemented depending upon the level of compromise of the natural knee anatomy. The knee anatomy complex includes the knee joint between the femur distal end and the tibia proximal end, and the surrounding anterior and posterior cruciate ligaments (ACL, PCL), and medial and lateral collateral ligaments (MCL, LCL), which provide support and stabilization to the knee joint. When one or more ligaments are compromised, for example through injury, disease, or aging, a knee prosthesis system or assembly may be implanted to replace the knee joint.

A typical knee prosthesis system includes a tibial bone anchoring component, a tibial articulating component, which may be called a tibial insert, and a femoral bone anchoring component. Certain patients have experience different conditions in one knee or both knees that differ from accepted healthy knees. For example, one patient may present a right side knee that is in a varus condition while another patient may present with a right side knee in a valgus condition. Of course, other patients may present with a left knee or both knees in one or more of a varus and/or a valgus condition. For such patients, implanting a conventional knee prosthesis may result in a knee joint having constrained tibiofemoral rotation during flexion, or implanting a conventional knee prosthesis may result in a knee joint having less mediolateral stability during flexion.

Accordingly, such patients need a knee prosthesis that facilitates tibiofemoral rotation during flexion of a patient's knee with a condition. Such patients may also need a knee prosthesis that increases mediolateral stability during flexion during flexion. The present disclosure addresses these needs.

SUMMARY

The various apparatus, devices, systems, and/or methods of the present disclosure have been developed in response to the present state of the art, and in particular, in response to the problems and needs in the art that have not yet been fully solved by currently available technology.

One general aspect of the present disclosure can include a knee joint prosthesis system for implantation in a first knee joint of a patient. The knee joint prosthesis system may include a tibial baseplate component configured to be implanted on the tibia, the tibial baseplate component may include an insert interface; a femoral component configured to be implanted on the femur, the femoral component may include a femoral articulation surface; and a tibial insert that may include a baseplate interface attachable to the insert interface of the tibial baseplate component, the tibial insert may include a tibial articulation surface configured to articulate with the femoral articulation surface; where: the tibial articulation surface may include a medial tibial compartment and a lateral tibial compartment that is asymmetrical to the medial tibial compartment; the tibial articulation surface may be shaped to cooperate with the femoral articulation surface to adapt kinematics of the first knee joint having the condition; and the tibial articulation surface is suitable for implantation in a second knee joint on the second side, the second knee joint lacking the condition.

Implementations may include one or more of the following features. The knee joint prosthesis system may include a femoral component that is configured for the first side and the tibial insert is configured for the second side of the patient. In certain embodiments, the first knee joint may be a right knee joint of the patient; the second knee joint may be a left knee joint of the patient; and the tibial insert may be configured for the left knee joint and attached to the insert interface of the tibial baseplate component of the right knee joint; and another tibial insert may be configured for the right knee joint.

The tibial articulation surface may facilitate tibiofemoral rotation within the lateral tibial compartment during flexion of the first knee joint where the condition is a valgus knee joint. The tibial articulation surface may adjust mediolateral stability during flexion of the first knee joint where the condition is a varus knee joint. The tibial articulation surface may increase constraint on a lateral collateral ligament of the first knee joint and decreases tension on a medial collateral ligament of the first knee joint.

The medial tibial compartment may include a medial perimeter, a medial high point, and a medial low point and where the lateral tibial compartment may include a lateral perimeter, a lateral high point, and a lateral low point.

The femoral articulation surface may include a medial femoral compartment and a lateral femoral compartment and where the medial tibial compartment engages the lateral femoral compartment at a lateral dwell point during flexion and the lateral tibial compartment engages the medial femoral compartment at a medial dwell point during flexion. The lateral dwell point migrates anteriorly and outwardly and the medial dwell point migrates posteriorly and outwardly. In one embodiment, the medial femoral compartment and the lateral femoral compartment are symmetrical. The tibial insert may include one of a cruciate retaining tibial insert, a constrained condylar knee tibial insert, a posterior stabilizing tibial insert, and a medially-laterally asymmetric tibial insert and the condition may include one of a varus condition and a valgus condition.

One general aspect of the present disclosure can include a knee joint prosthesis system for implantation in a knee joint of a patient. The knee joint prosthesis system may include a tibial baseplate component configured to be implanted on the tibia, the tibial baseplate component may include an insert interface; a femoral component configured to be implanted on the femur, the femoral component may include a femoral articulation surface; a right side tibial insert attachable to the insert interface of the tibial baseplate component, the right side tibial insert may include a tibial articulation surface configured to articulate with the femoral articulation surface and rotate the tibia about a longitudinal axis passing through a medial tibial compartment of the right side tibial insert during flexion or extension of a right side knee joint; a left side tibial insert attachable to the insert interface of the tibial baseplate component, the left side tibial insert may include a tibial articulation surface configured to articulate with the femoral articulation surface and rotate the tibia about the longitudinal axis passing through a medial tibial compartment of the left side tibial insert during flexion or extension of a left side knee joint; and the tibial articulation surface of the right side tibial insert may be shaped to cooperate with the femoral articulation surface to change kinematics of the knee joint having the condition if the knee joint is the left side knee joint; and the tibial articulation surface of the left side tibial insert is shaped to cooperate with the femoral articulation surface to change kinematics of the knee joint having the condition if the knee joint is the right side knee joint.

Implementations may include one or more of the following features. The knee joint prosthesis system where the knee joint is a right knee joint of the patient; and where the left side tibial insert is attached to the insert interface of the tibial baseplate component of the right knee joint such that the left side tibial insert constrains the femoral articulation surface within the medial tibial compartment and mitigates the condition. The tibial articulation surface facilitates tibiofemoral rotation within the medial tibial compartment during flexion of the knee joint where the condition is a valgus knee joint. The tibial articulation surface adjusts mediolateral stability during flexion of the knee joint where the condition is a varus knee joint. The tibial articulation surface increases constraint on a lateral collateral ligament of the knee joint and decreases tension on a medial collateral ligament of the knee joint. The medial tibial compartment may include a medial perimeter, a medial high point, and a medial low point and where each of the right side tibial insert and the left side tibial insert may include a lateral tibial compartment that may include a lateral perimeter, a lateral high point, and a lateral low point. Each of the right side tibial insert and the left side tibial insert may include a lateral tibial compartment and a medial tibial compartment and where the femoral articulation surface may include a medial femoral compartment and a lateral femoral compartment and where the medial tibial compartment engages the lateral femoral compartment at a lateral dwell point during flexion and the lateral tibial compartment engages the medial femoral compartment at a medial dwell point during flexion.

One general aspect of the present disclosure can include a method for adapting kinematics of a knee joint having a condition. The method includes determining that the knee joint has the condition; implanting a femoral component on the femur, the femoral component may include a femoral articulation surface; implanting a tibial baseplate component on the tibia, the tibial baseplate component may include an insert interface; based on the condition, selecting a tibial insert configured for the second side, the tibial insert may include a baseplate interface attachable to the insert interface of the tibial baseplate component, the tibial insert may include a tibial articulation surface configured to articulate with the femoral articulation surface to adapt kinematics of the knee joint; and connecting the selected tibial insert to the tibial baseplate to adapt kinematics of the knee joint based on the condition.

Implementations may include one or more of the following features. The method where a condition of the knee joint may include one of a varus condition, a valgus condition, and a balanced condition.

One general aspect of the present disclosure can include a knee joint prosthesis system for implantation in a knee joint of a patient. The knee joint prosthesis system includes a femoral component configured to be implanted on the femur, the femoral component may include a femoral articulation surface; a right side tibial component attachable on the tibia, the right side tibial component may include a tibial articulation surface configured to articulate with the femoral articulation surface and rotate the tibia about a longitudinal axis passing through a medial tibial compartment of the right side tibial component during flexion or extension of a right side knee joint; a left side tibial component attachable on the tibia, the left side tibial component may include a tibial articulation surface configured to articulate with the femoral articulation surface and rotate the tibia about a longitudinal axis passing through a medial tibial compartment of the left side tibial component during flexion or extension of a left side knee joint; and the tibial articulation surface of the right side tibial component is shaped to cooperate with the femoral articulation surface to change kinematics of the knee joint having the condition if the knee joint may include the left side knee joint; and the tibial articulation surface of the left side tibial component is shaped to cooperate with the femoral articulation surface to change kinematics of the knee joint having the condition if the knee joint may include the right side knee joint.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings.

FIG. 11A is a perspective rear view of another tibial insert of the disclosure; FIG. 11B is a top view of the tibial insert of FIG. 11A; FIG. 11C is a posterior view of the tibial insert of FIG. 11A; FIG. 11D is an anterior view of the tibial insert of FIG. 11A; FIG. 11E is a bottom view of the tibial insert of FIG. 11A.

FIG. 13 is a chart demonstrating the interchangeability of the tibial inserts disclosed herein with various femoral components.

FIG. 25A is perspective posterior view of a knee prosthesis assembly in 0 degree flexion.

FIG. 25B is a perspective posterior view of the knee prosthesis assembly of FIG. 25A with a medial-lateral cross-section.

FIG. 25C is a posterior view of the knee prosthesis assembly of FIG. 25B.

FIG. 27A is perspective posterior view of a knee prosthesis assembly in 90 degree flexion.

FIG. 27B is a perspective posterior view of the knee prosthesis assembly of FIG. 27A with a medial-lateral cross-section.

FIG. 27C is a posterior view of the knee prosthesis assembly of FIG. 27B.

Figure 1A:
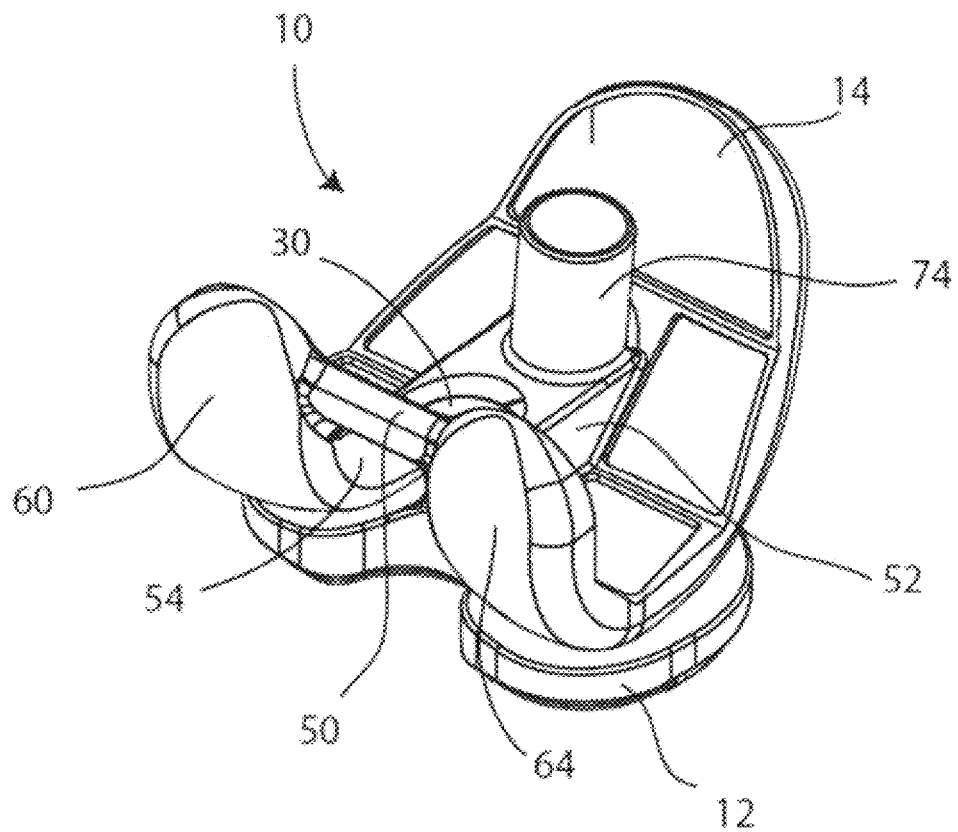
FIG. 1A is a perspective rear view of an assembly of the disclosure, including a posterior stabilizing femoral component and a tibial insert coupled in extension.

It is to be understood that the drawings are for purposes of illustrating the concepts of the disclosure and may not be to scale. Furthermore, the drawings illustrate exemplary embodiments and do not represent limitations to the scope of the disclosure.

DETAILED DESCRIPTION

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the following more detailed description of the embodiments of the apparatus, instruments, systems, and methods, as represented in the Figures, is not intended to limit the scope of the disclosure, as claimed, but is merely representative of exemplary embodiments of the disclosure.

Standard medical planes of reference and descriptive terminology are employed in this specification. While these terms are commonly used to refer to the human body, certain terms are applicable to physical objects in general. A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric.

The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular. Anterior means toward the front of a body.

Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. Antegrade means forward moving from a proximal location/position to a distal location/position or moving in a forward direction. Retrograde means backward moving from a distal location/position to a proximal location/position or moving in a backwards direction. Sagittal refers to a midline of a patient's anatomy, which divides the body into left or right halves. The sagittal plane may be in the center of the body, splitting it into two halves.

As used herein, a "deploy" or "deployment" refers to an act, action, process, system, method, means, or apparatus for inserting an implant or prosthesis into a part, body part, and/or patient. "Deploy" or "deployment" can also refer to an act, action, process, system, method, means, or apparatus for placing something into therapeutic use. A device, system, component, medication, drug, compound, or nutrient may be deployed by a human operator, a mechanical device, an automated system, a computer system or program, a robotic system, or the like.

As used herein, "implant" refers to a medical device manufactured to replace a missing biological structure, support a damaged biological structure, or enhance an existing biological structure. Medical implants are man-made devices. The surface of implants that contact the body may be made of, or include a biomedical material such as titanium, stainless steel, carbon fiber, another metallic alloy, silicone, or apatite, or any combination of these depending on what is the most functional. In some cases implants contain electronics, e.g. artificial pacemaker and cochlear implants. Some implants are bioactive, such as subcutaneous drug delivery devices in the form of implantable pills or drug-eluting stents. Orthopedic implants may be used to alleviate issues with bones and/or joints of a patient's body. Orthopedic implants are used to treat bone fractures, osteoarthritis, scoliosis, spinal stenosis, and chronic pain. Examples of orthopedic implants include, but are not limited to, a wide variety of pins, rods, screws, anchors, and plates used to anchor fractured bones while the bones heal or fuse together. (Search "implant (medicine)" on Wikipedia.com May 26, 2021. CC-BY-SA 3.0 Modified. Accessed Jun. 30, 2021.)

The present disclosure is an apparatus, system, and method for implantation in a knee joint of a patient where the knee joint has a condition such as varus or valgus. In one embodiment, the system uses a tibial insert and/or a tibial component configured for a second knee opposite of the knee joint receiving arthroplasty. By using a tibial insert and/or a tibial component designed for an opposite knee, the condition of the knee joint is remediated.

Figure 1B:
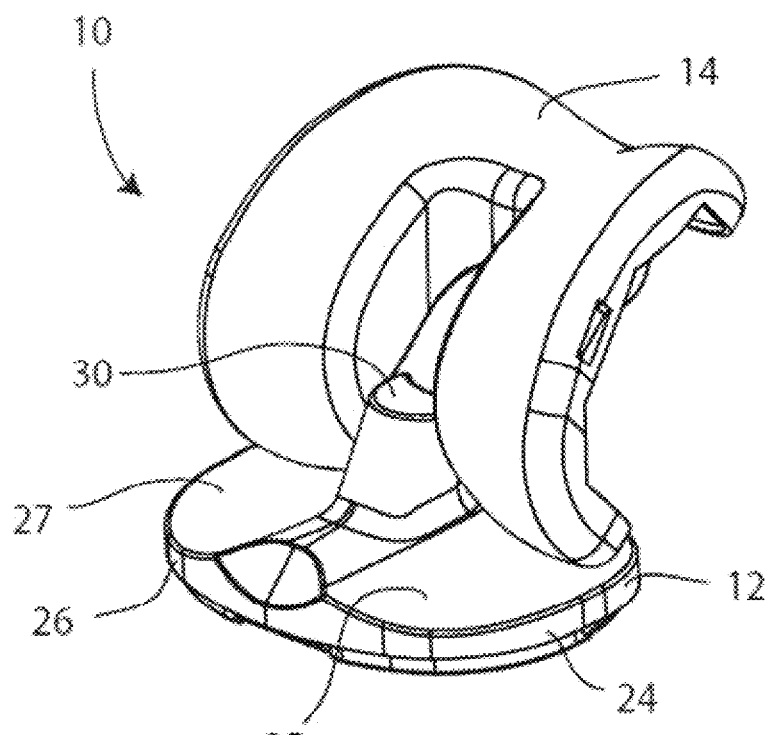
FIG. 1B is a perspective front view of the assembly of FIG. 1A in flexion.
Figure 2:
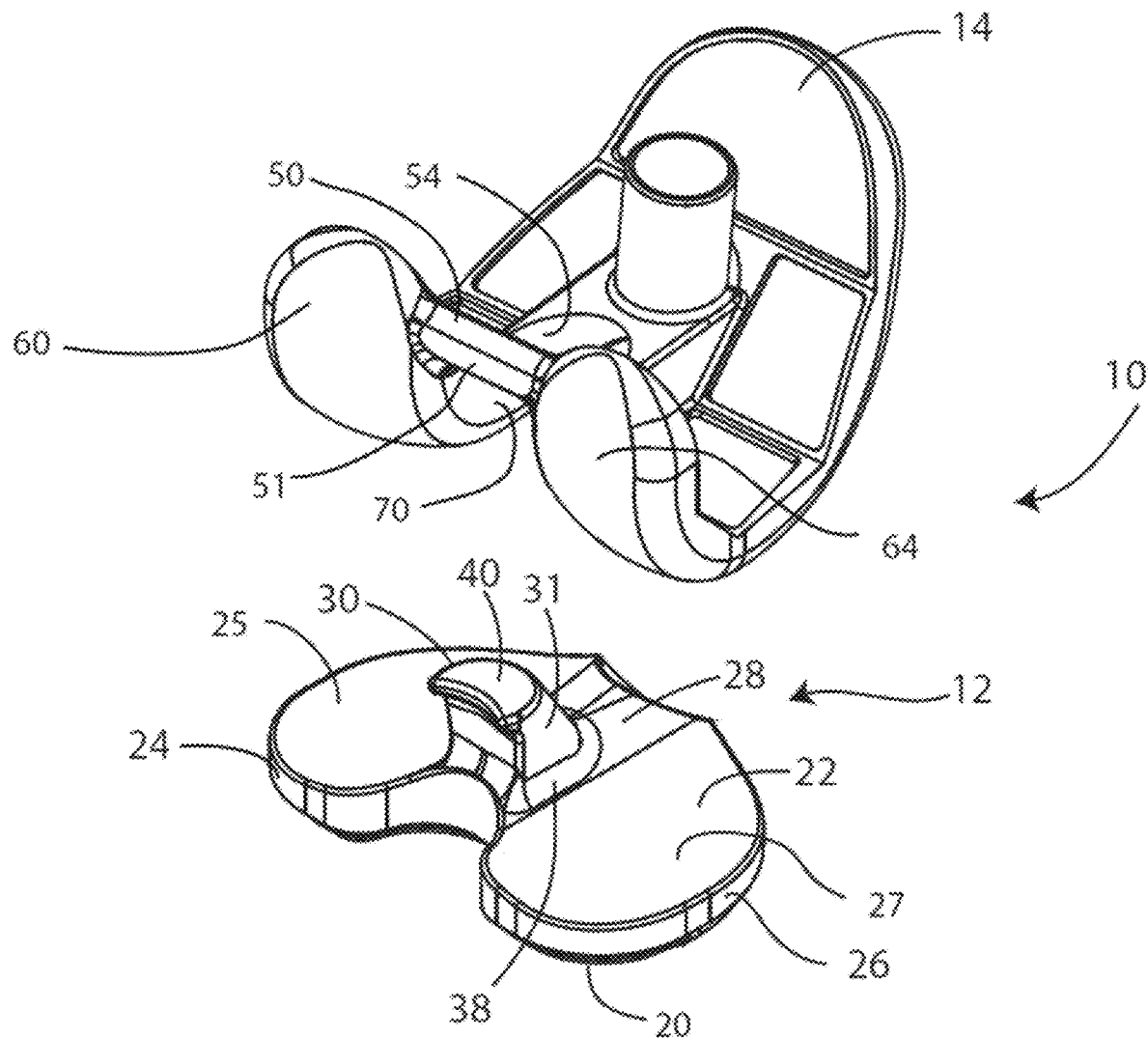
FIG. 2 is an exploded view of the assembly of FIG. 1A.

Referring to FIGS. 1A-2, an assembly 10 for an implantable knee prosthesis is shown including a femoral component 14 and a tibial insert 12. As used herein, "femoral" describes a feature, aspect, component, function, attribute, structure or part that is, or is configured to, connect to, couple to, interact with, interoperate with or is otherwise associated with a femur bone of a human or animal. As used herein, an "insert" refers to an apparatus, instrument, structure, device, component, system, or assembly that is structured, organized, configured, designed, arranged, or engineered to couple or connect to one or more other components, parts, or devices. In certain embodiments, an insert is configured to be inserted or deployed between two or more other components or structures. The femoral component 14 and tibial insert 12 are shown coupled in extension in FIG. 1A, coupled in flexion in FIG. 1B, and shown in an exploded view in FIG. 2. The tibial insert 12 may be further coupled to a tibial baseplate component (See FIG. 24A) which may be implanted in a prepared tibia of a patient (also not shown). The femoral component 14 and tibial insert 12 illustrated in FIGS. 1A-2 are right femoral and tibial insert components. In certain embodiments, left femoral and tibial insert components may be mirror images of the right femoral and tibial insert components shown in FIGS. 1A-2. The femoral component 14 may also be referred to as a posterior stabilizing femoral component 14 (or "PS femoral component") and the tibial insert 12 may also be referred to as a posterior stabilizing tibial insert (or "PS insert").

FIGS. 3A-3D show the PS insert 12 of FIGS. 1A-2 in isolation. The PS insert 12 may include a fixation side 20, which may be an inferior side, opposite an articulation side 22, which may be a superior side. The articulation side 22 may include a medial tibial compartment 24 having a medial condylar articulation surface 25 and a lateral tibial compartment 26 having a lateral condylar articulation surface 27.

As used herein, "tibial" describes a feature, aspect, component, function, attribute, structure or part that is, or is configured to, connect to, couple to, interact with, interoperate with or is otherwise associated with a tibia bone of a human or animal. As used herein, a "compartment" refers to a section, chamber, part or area, or one of a set of parts into which an area may be subdivided. (Search "compartment" on wordhippo.com. WordHippo, 2021. Web. Accessed 8 Dec. 2021. Modified.)

A central portion 28 may separate the medial tibial compartment 24 from the lateral tibial compartment 26. A post 30 may protrude superiorly from the central portion 28 and extend from a post base 38 to a post top or post superior end 40. From the anterior perspective (shown in FIG. 3B) and/or the posterior perspective (shown in FIG. 3A), the post 30 may have its maximum medial-lateral or horizontal width toward the post superior end 40 of the post 30, and its minimum medial-lateral or horizontal width toward the post base 38 of the post 30. The post 30 may also be bilaterally symmetrical from the anterior and/or posterior perspectives. A recess 45 may be formed posterior to the central portion 28, between the medial and lateral tibial compartments 24, 26, and may provide room for a posterior cruciate ligament (not shown). The PS insert 12 may further include an insert base 46, which may further include an engagement feature 48 for engagement with a tibial baseplate component.

Continuing with FIGS. 1A-3D, the post 30 may have an articulation surface 31 extending around the post 30 on the medial, posterior, lateral, and anterior aspects of the post 30. As used herein, "articulation" refers to a joint or juncture between bones or cartilage in a skeleton of a vertebrate. In certain embodiments, "articulation" may also refer to the action or manner of jointing or interrelating, or the state of being jointed or interrelated (search "articulation" on Merriam-Webster.com. Merriam-Webster, 2021. Web. 15 Nov. 2021. Modified.)

Figure 3A:
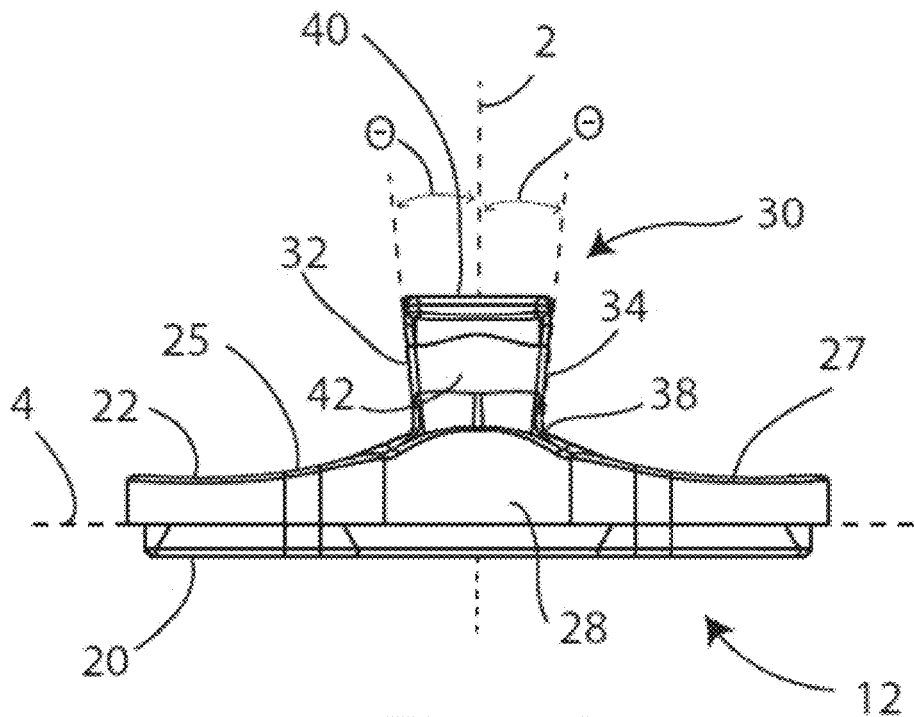
FIG. 3A is a posterior view of the tibial insert of FIG. 1A.
Figure 3B:
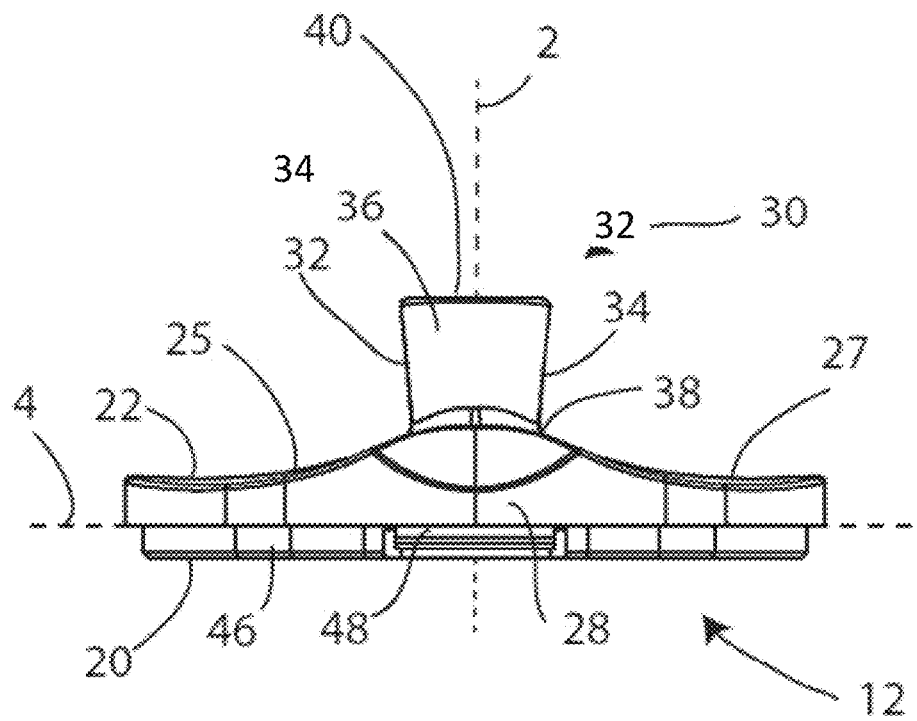
FIG. 3B is an anterior view of the tibial insert of FIG. 1A.
Figure 6:
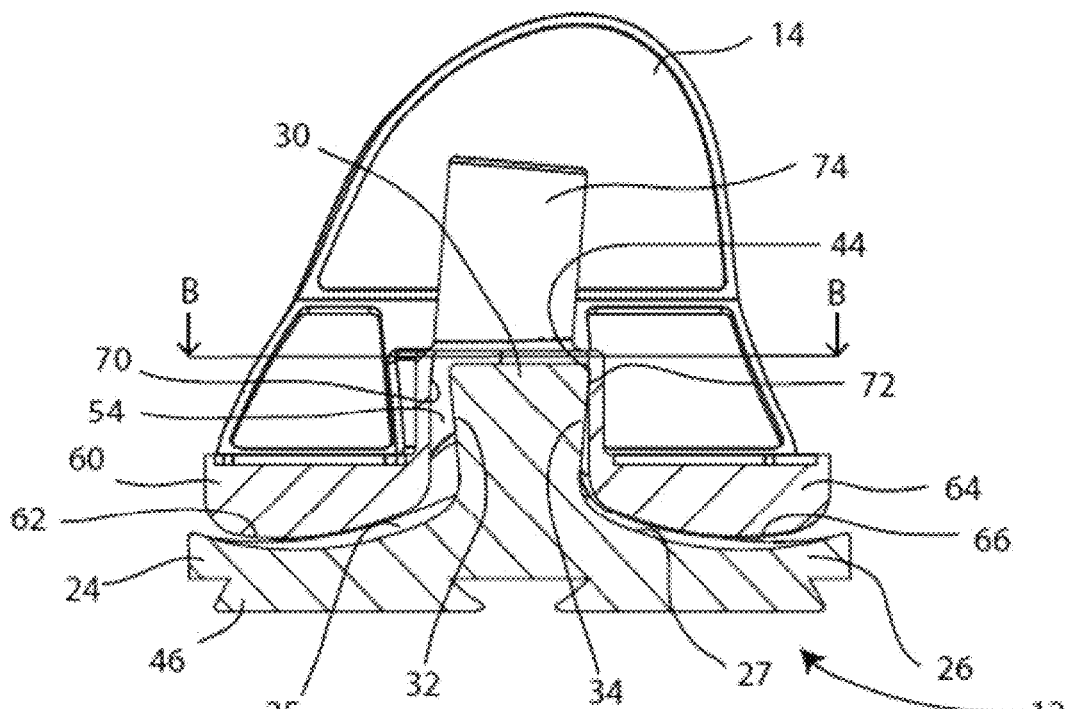
FIG. 6 is a posterior cross-sectional view of the assembly of FIG. 1A, taken along line A-A in FIG. 5.
Figure 7:
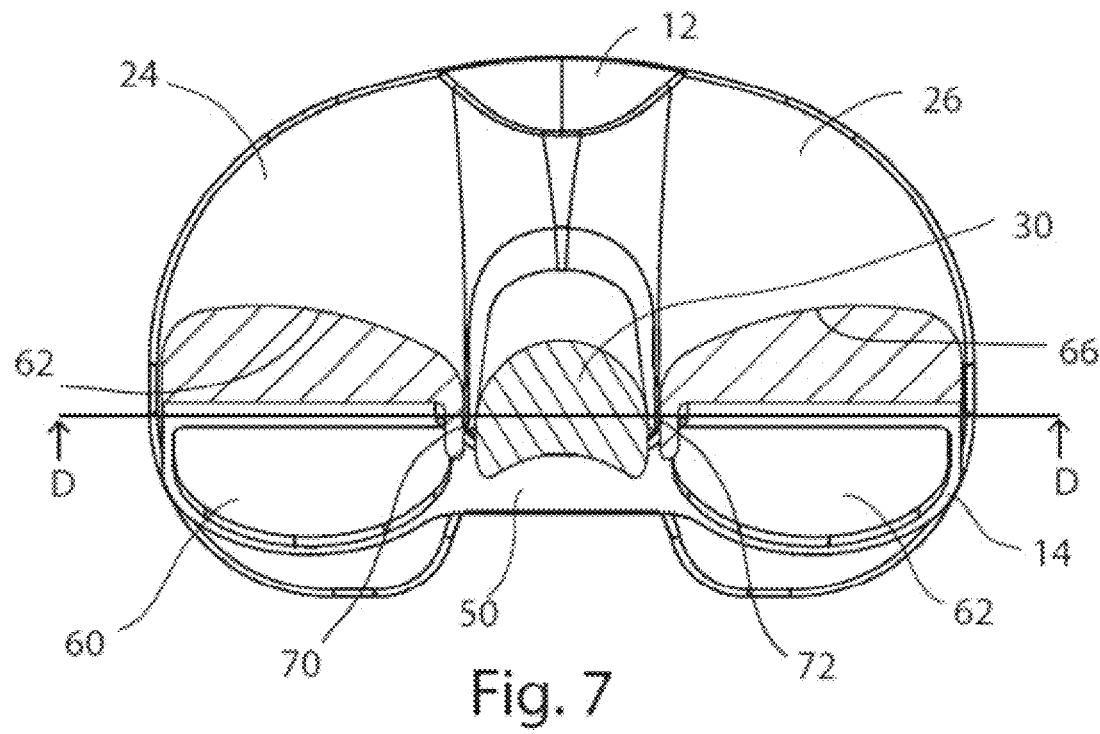
FIG. 7 is a top down cross-sectional view of the assembly of FIG. 1B, taken along line C-C in FIG. 8.
Figure 8:
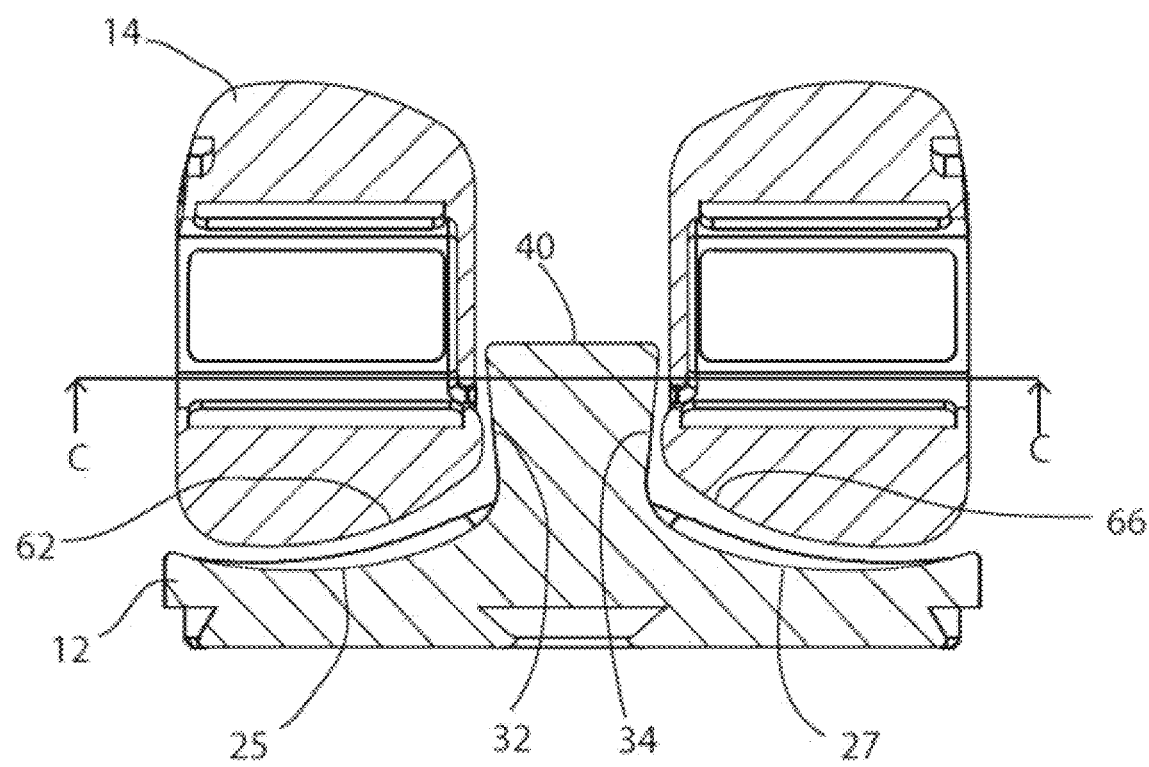
FIG. 8 is a posterior cross-sectional view of the assembly of FIG. 1B, taken along line a D-D in FIG. 7.

The articulation surface 31 may include a medial articulation surface 32, a lateral articulation surface 34, an anterior post surface 36, and a posterior articulation surface 42. The medial and lateral articulation surfaces 32, 34 may be non-parallel to one another and taper inward from the post superior end 40 to the post base 38 relative to an insert midline vertical axis 2, as shown in FIGS. 3A and 3B. As shown in FIG. 3A, an angle θ between the vertical axis 2 and each tapered surface 32, 34 may be about 6.5, in at least one embodiment. Since the post 30 may be bilaterally symmetrical, the angle θ may be the same on both the medial and lateral articulation surfaces 32, 34 of the post 30. In other embodiments of the disclosure, angle θ may range from about 6° to 11° degrees. The medial articulation surface 32 may be continuous with the medial condylar articulation surface 25, and the lateral articulation surface 34 may be continuous with the lateral condylar articulation surface 27, as can been further seen in cross-section in FIGS. 6 and 8. The anterior post surface 36 may extend between the medial and lateral articulation surfaces 32, 34 and may be convexly rounded. The anterior post surface 36 may also taper outward from the post superior end 40 to the post base 38 relative to the midline vertical axis 2, as best seen in FIG. 3D. In other embodiments of the PS insert 12, the anterior post surface 36 may include less or no taper.

Figure 3C:
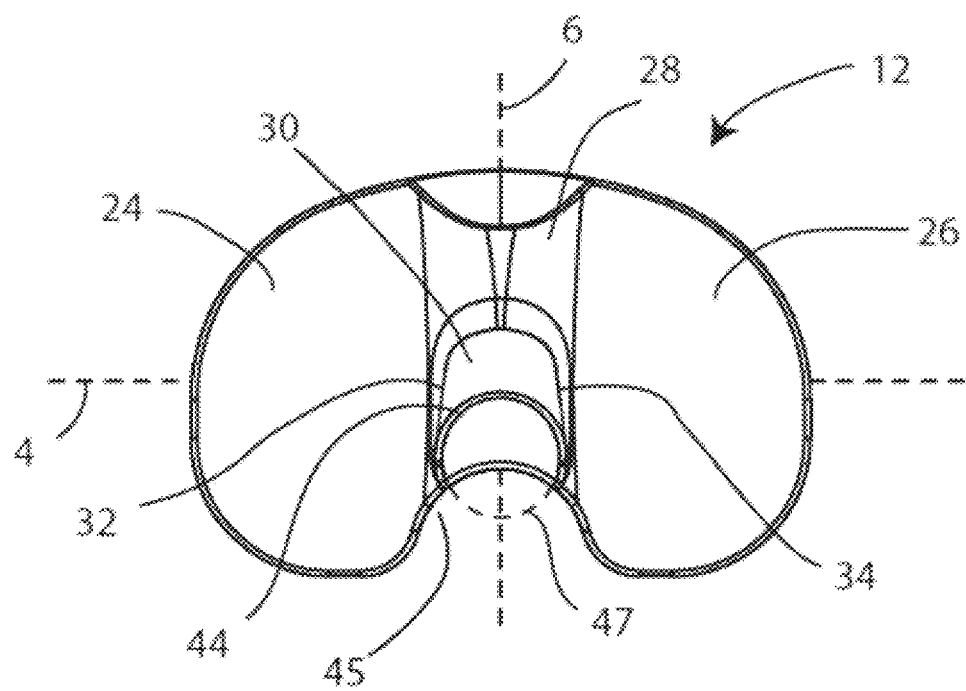
FIG. 3C is a superior view of the tibial insert of FIG. 1A.
Figure 3D:
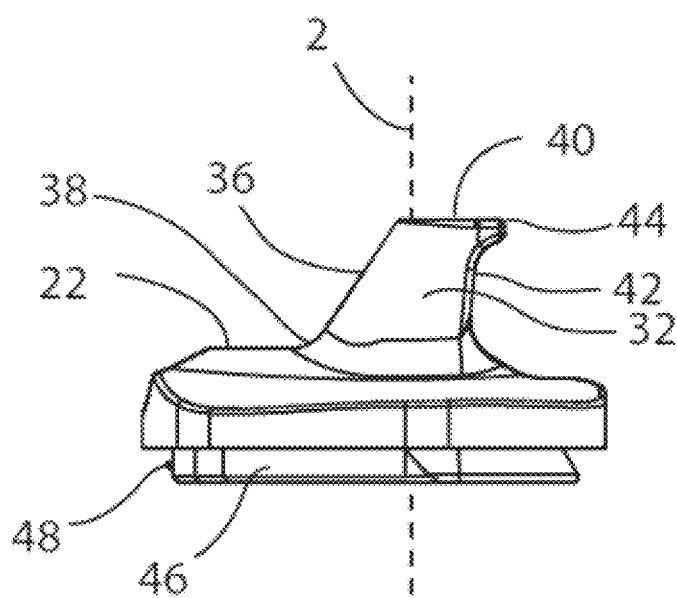
FIG. 3D is a medial side view of the tibial insert of FIG. 1A.
Figure 4:
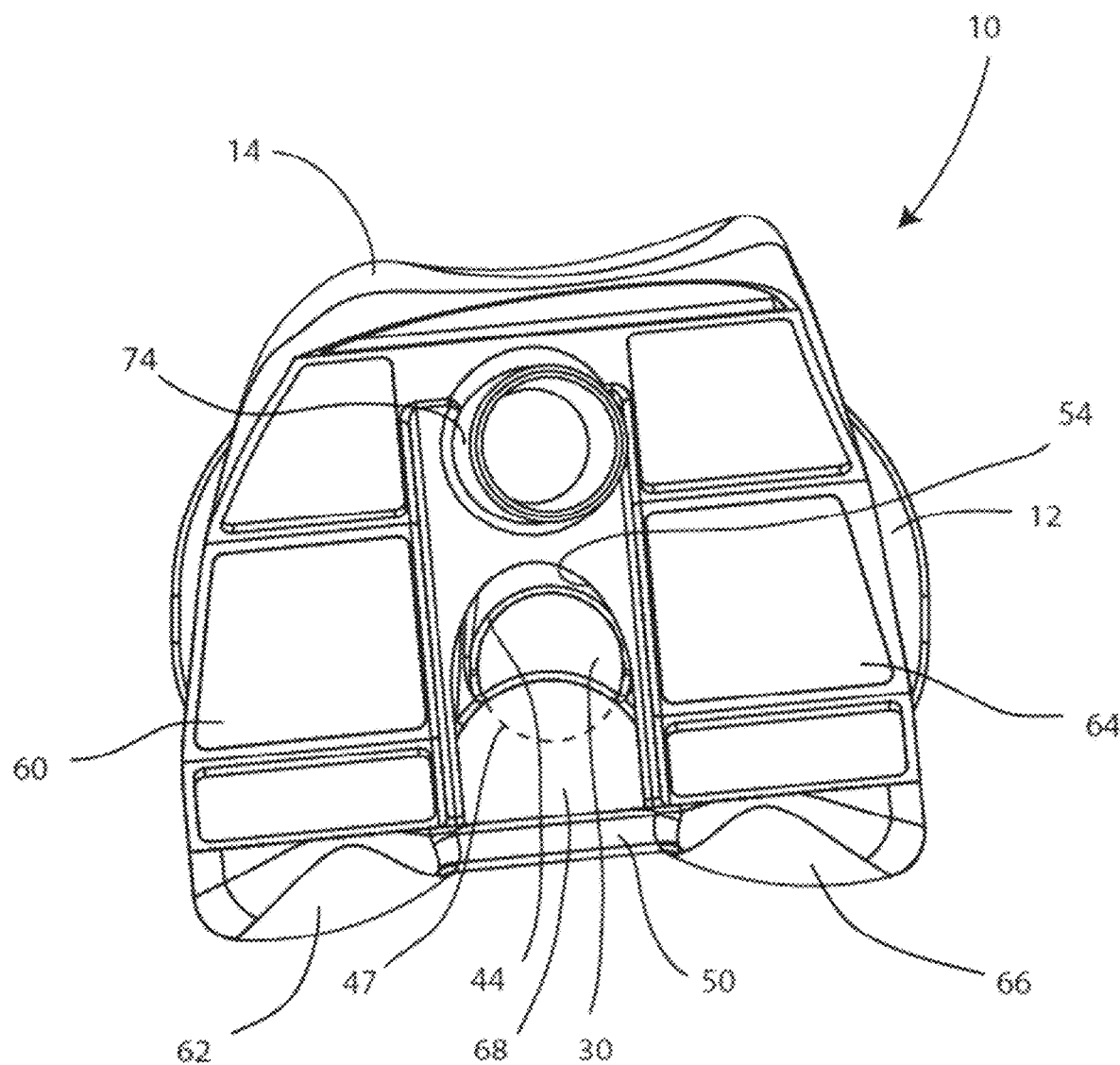
FIG. 4 is a top down view of the assembly of FIG. 1A.
Figure 5:
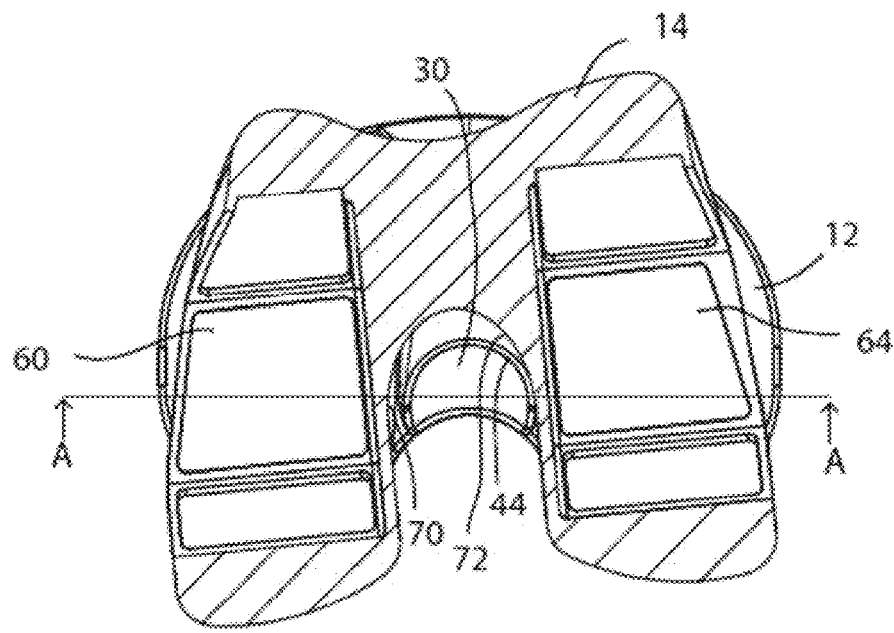
FIG. 5 is a top down cross-sectional view of the assembly of FIG. 1A, taken along line B-B in FIG. 6.

Referring to FIG. 3C, the boundary of the post superior end 40 defines a rounded rim 44 shaped as a portion of a circle defined by a circular envelope 47, as seen from a superior perspective. The post superior end 40 and rim 44 may be crescent-shaped with a concave recess toward a posterior end of the post 30 as shown and may permit passage of the posterior cruciate ligament. The post superior end 40 may be circular; the rim 44 may provide increased rotational range of motion and surface contact against the femoral component 14 in comparison to traditional posts with a more square or rectangular shape and no rim. Thus, the rounded post superior end 40 and rim 44 may allow for surface contact with the femoral component 14 in contrast to the mere point or edge contact that is achieved by traditional posts that do not have these features.

The PS femoral component 14 depicted in FIGS. 1-8 may include a cam element or cam bar 50 and a box structure 52 for providing posterior stabilization in place of absent ligaments. The cam bar 50 may include a cam articulating surface 51 which may contact the posterior articulation surface 42 of the post 30 during flexion, as in FIGS. 1B and 7. An internal articulation surface 54 may reside on the inside of the box structure 52 and may contact the post 30 during articulation and rotation of the knee joint. The internal articulating surface 54 may be concavely curved and may contact the rim 44 of the post 30 during axial rotation of the knee joint about the post. The PS femoral component 14 may further include a medial condyle 60 having a medial condylar articulation surface 62, and a lateral condyle 64 having a lateral condylar articulation surface 66. The medial and lateral condylar articulation surfaces 62, 66 may articulate against the PS insert 12 medial and lateral condylar articulation surfaces 25, 27, respectively. A gap 68 may be formed between the medial and lateral condyles 60, 64, with the cam bar 50 extending medial-laterally across the gap 68. The internal articulation surface 54 may include a medial portion 70 continuous with a lateral portion 72. In the embodiment depicted, a fixation post 74 may protrude superiorly from the PS femoral component 14. However, in other embodiments of the PS femoral component 14, the fixation post 74 may be absent and/or other fixation features such as posts, spikes, pegs, webs, keels, or teeth may be present to affix the PS femoral component 14 to a prepared femur (not shown).

Figure 9:
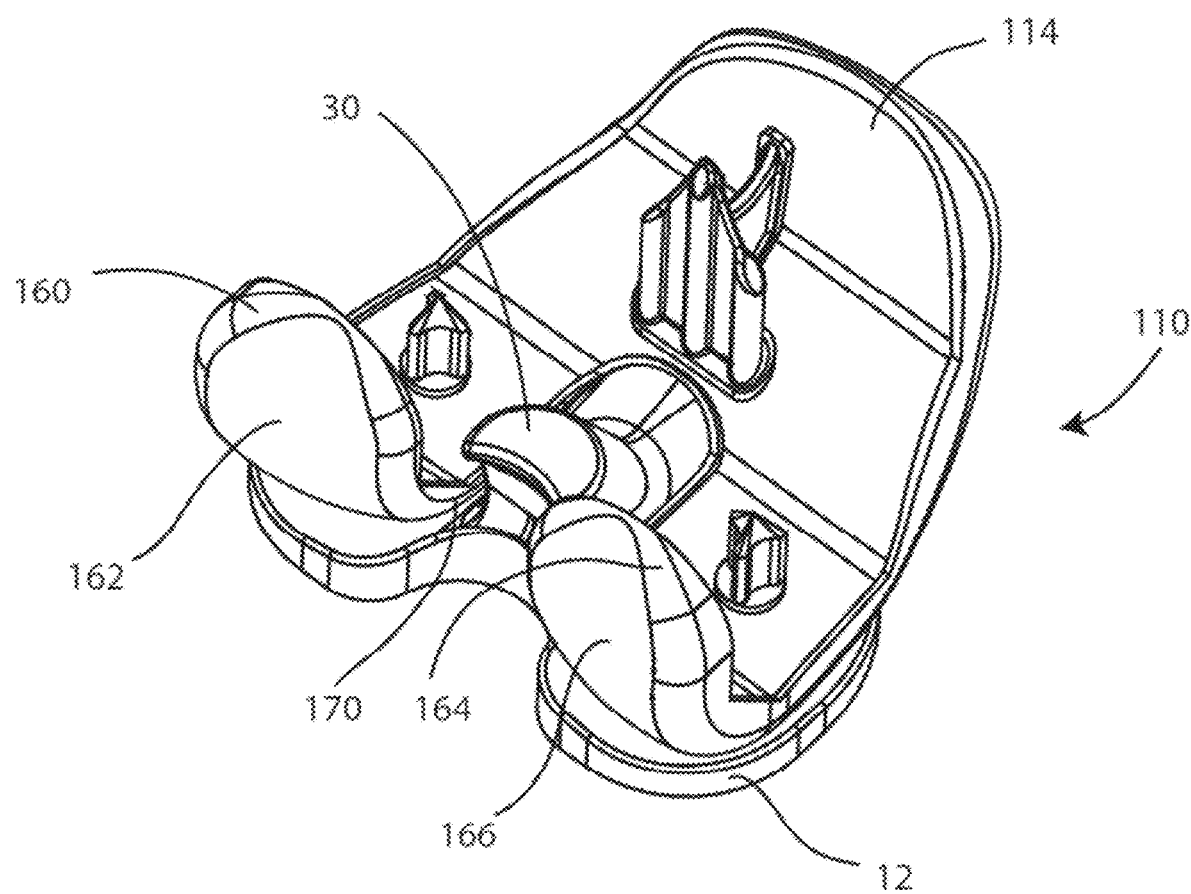
FIG. 9 is a perspective rear view of an assembly of the disclosure, including a cruciate U retaining femoral component and the tibial insert of FIG. 1A coupled in extension.
Figure 10:
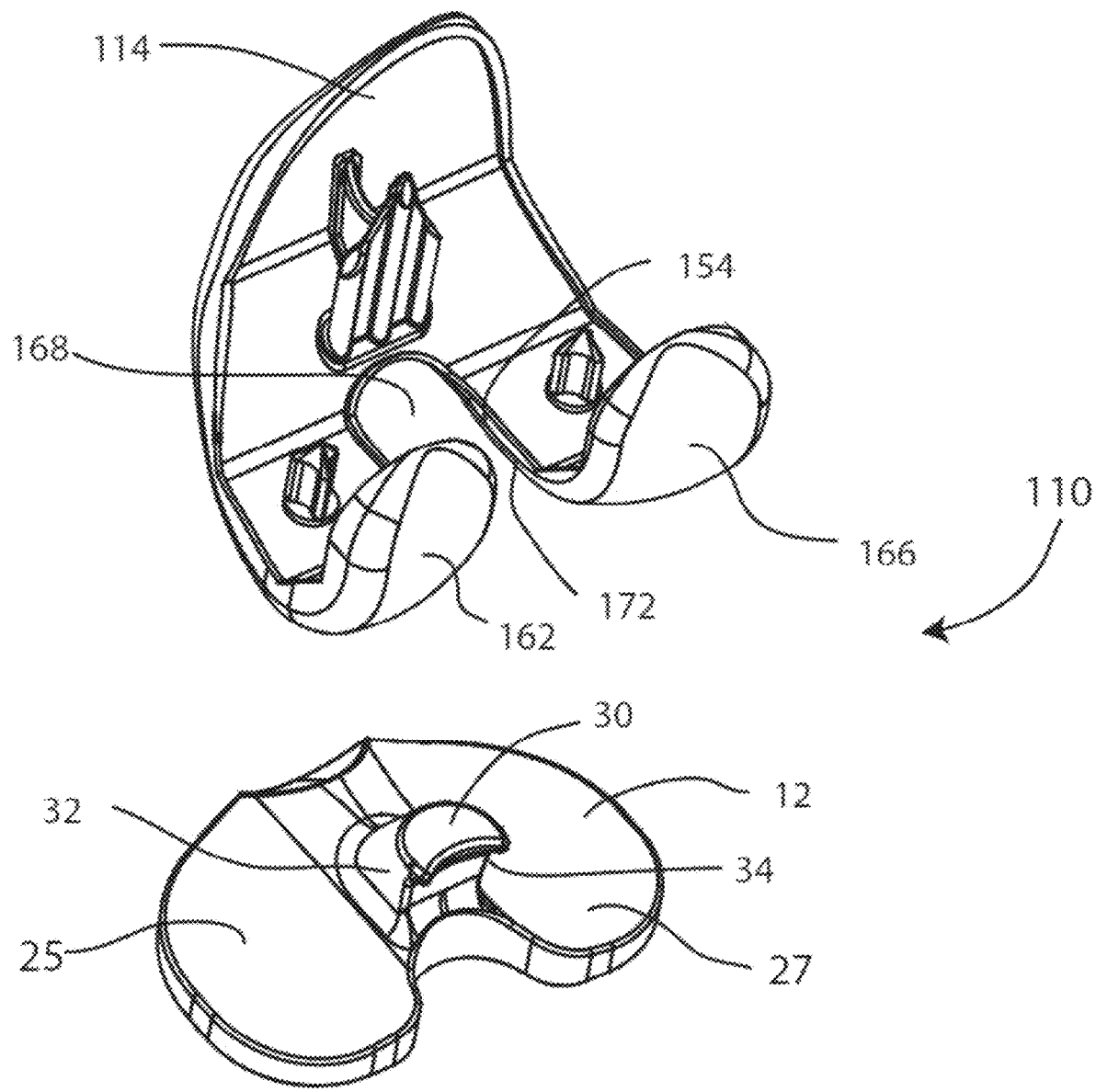
FIG. 10 is an exploded perspective rear view of the assembly of FIG. 9.

Referring to FIGS. 9 and 10, another assembly 110 embodiment of the disclosure may include the PS insert 12 of FIGS. 1-8 coupled with a cruciate retaining femoral component 114 (or "CR femoral component"). The CR femoral component 114 may include medial and lateral condyles 160, 164, with a gap 168 formed between the medial and lateral condyles 160, 164. As a CR femoral component 114, no cam bar or box may be present. The medial and lateral condyles 160, 164 may include medial and lateral condylar articulation surfaces 162, 166, and an internal articulation surface 154 with medial and lateral articulating surfaces 170, 172.

The medial and lateral articulation surfaces 32, 34 of the post 30 may be tapered and may permit natural articulation of the CR femoral component 114 with the PS insert 12, which may not be achievable if the post 30 were not tapered. For example, if the post 30 had straight sides instead of tapered sides, the wider width of the post 30 at the base of the post 30 would interfere with the internal articulating surfaces 170, 172 of the medial and lateral condyles 160, 164. When the PS femoral component 14 is coupled with the PS insert 12 to form assembly 10, as in FIG. 1A and FIG. 4, the circular shape of the post superior end 40 in combination with the tapered medial and lateral articulation surfaces 32, 34 of the post 30, may permit the PS femoral component 14 to articulate relative to the PS insert 12 in the manner of a posterior stabilized femoral component. However, when the PS insert 12 is paired and implanted with the CR femoral component 114, the resultant assembly 110 may provide the native articulation and rotation of a cruciate retaining implant.

Referring to FIGS. 11A-11E, an alternative embodiment of a tibial insert 212 is shown. Tibial insert 212 may be referred to as a cruciate retaining tibial insert 212 (or "CR insert"). In a system of the disclosure, CR insert 212 may be implanted with the CR femoral component 114 and a tibial baseplate component (See FIG. 24A) to form a cruciate retaining knee prosthesis system. The CR insert 212 may include a fixation side 220, which may be an inferior side, opposite an articulation side 222, which may be a superior side. The articulation side 222 may include a medial tibial compartment 224 having a medial condylar articulation surface 225 and a lateral tibial compartment 226 having a lateral condylar articulation surface 227. A central portion 228 may separate the medial tibial compartment 224 from the lateral tibial compartment 226. A recess 245 may be formed posterior to the central portion 228, between the medial and lateral tibial compartments 224, 226, and may provide room for a posterior cruciate ligament. The CR insert 212 may further include an insert base 246 and an engagement feature 248 for engagement with a tibial baseplate component. The CR insert 212 may be coupled with the CR femoral component 114 to form a cruciate retaining assembly. This assembly may be implanted with a suitable tibial baseplate as a cruciate retaining knee prosthesis. The CR insert 212 may also be coupled with the PS femoral component 14 and implanted with a suitable tibial baseplate.

Figure 12A:
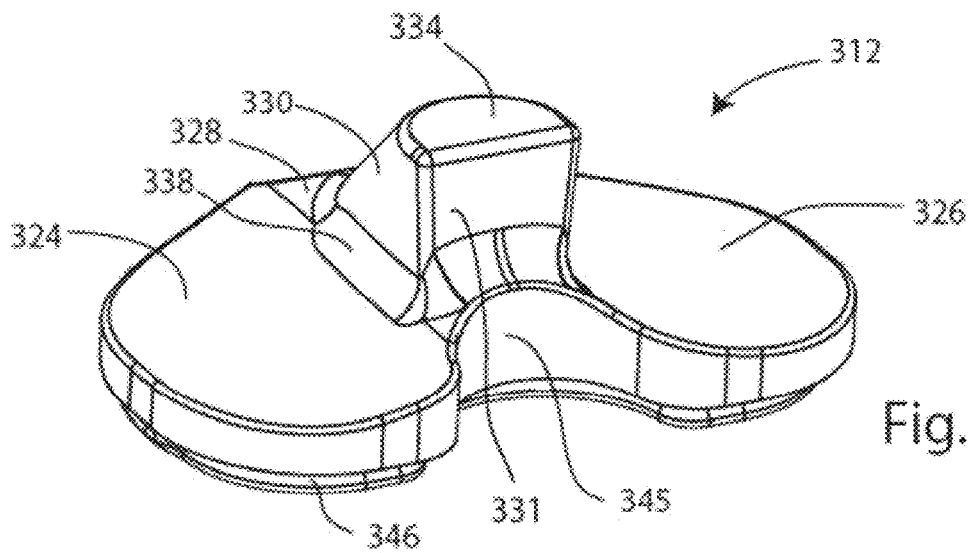
FIG. 12A is a perspective rear view of another tibial insert of the disclosure.
Figure 12B:
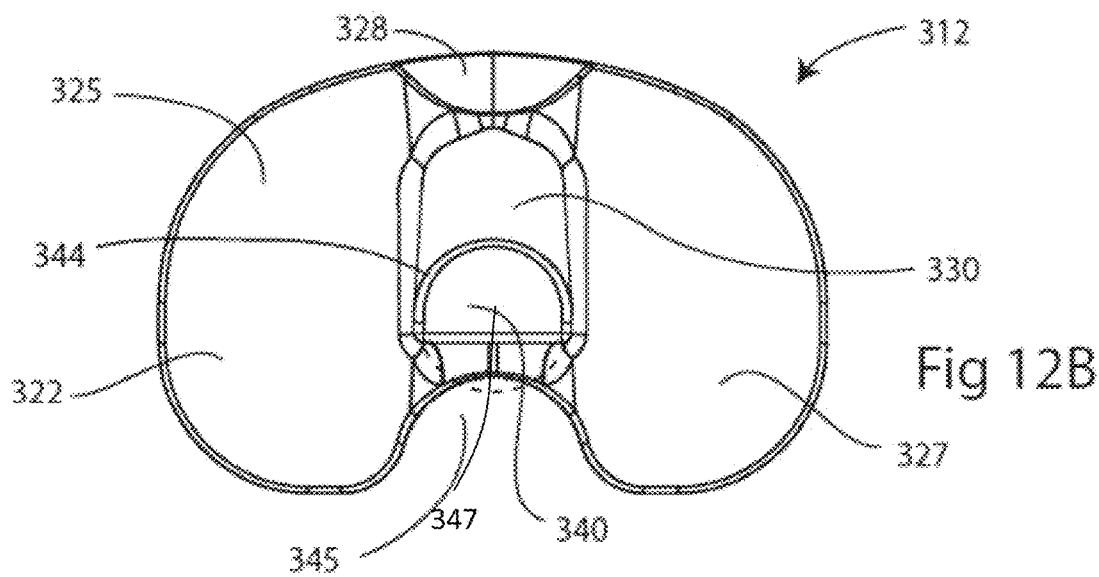
FIG. 12B is a top view of the tibial insert of FIG. 12A.
Figure 12C:
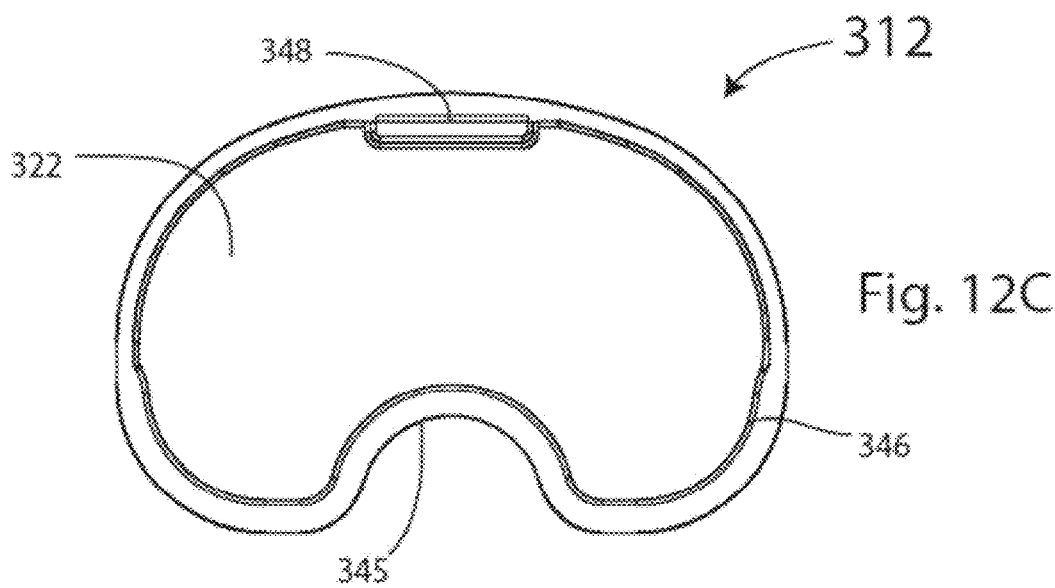
FIG. 12C is a bottom view of the tibial insert of FIG. 12A.
Figure 12D:
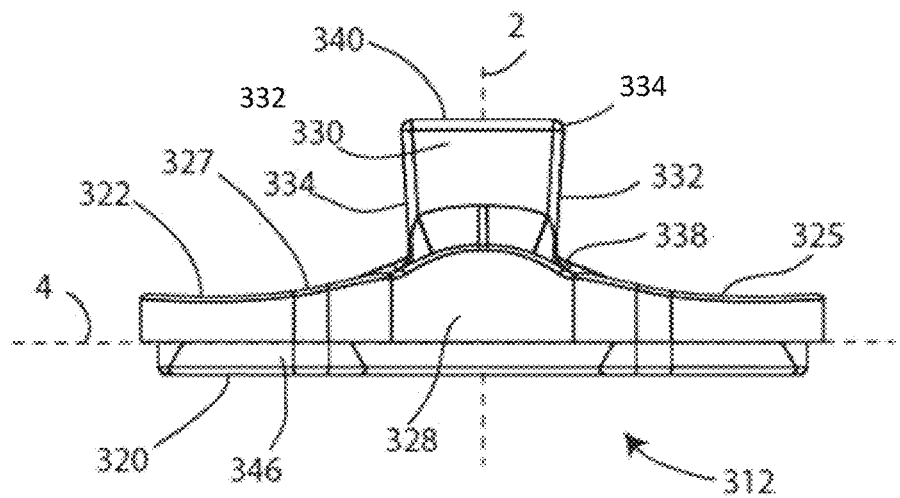
FIG. 12D is a posterior view of the tibial insert of FIG. 12A.
Figure 12E:
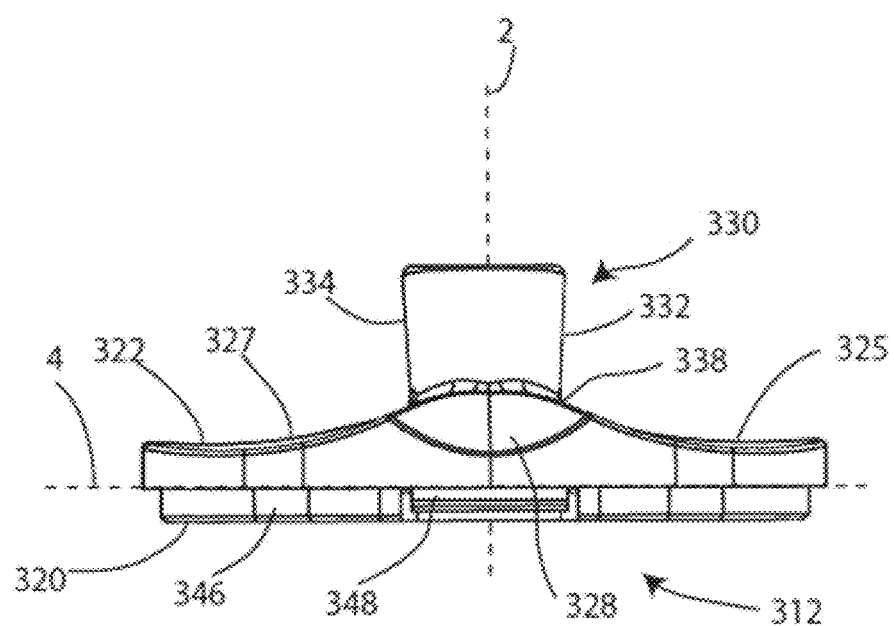
FIG. 12E is an anterior view of the tibial insert of FIG. 12A.

Referring to FIGS. 12A-12F, another alternative embodiment of a tibial insert 312 is shown. The tibial insert 312 may be referred to as a constrained condylar knee (CCK) tibial insert 312 (or "CCK insert"). The CCK insert 312 may include a fixation side 320, which may be an inferior side, opposite an articulation side 322, which may be a superior side. The articulation side 322 may include a medial tibial compartment 324 having a medial condylar articulation surface 325 and a lateral tibial compartment 326 having a lateral condylar articulation surface 327. A central portion 328 may separate the medial tibial compartment 324 from the lateral tibial compartment 326. A post 330 may protrude superiorly from the central portion 328, and extend from a post base 338 to a top, or post superior end 340. From the anterior perspective, as shown in FIG. 12E, and the posterior perspective, as shown in FIG. 12D, the post 330 may have its maximum medial-lateral or horizontal width at the superior end 340 of the post 330, and its minimum medial-lateral or horizontal width at the post base 338 of the post 330. The post 330 may be bilaterally symmetrical from the anterior and posterior perspectives. The CCK insert 312 may further include an insert base 346 and an engagement feature 348 for engagement with a tibial tray (not shown).

Figure 12F:
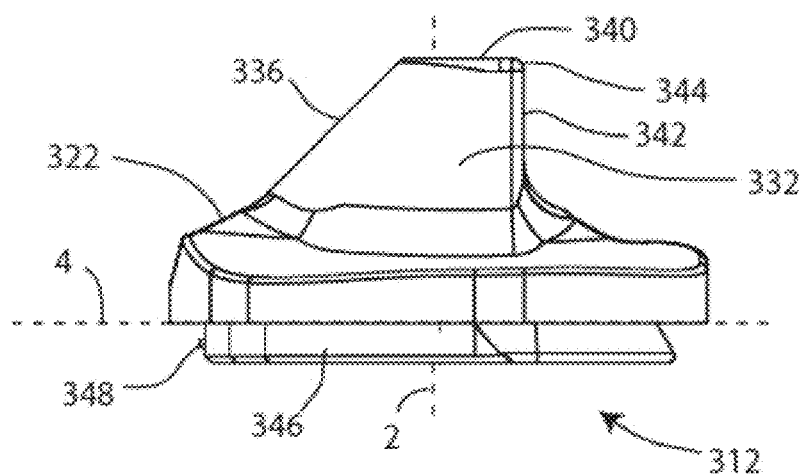
FIG. 12F is a medial side view of the tibial insert of FIG. 12A.

The post 330 may have an articulation surface 331 extending around the post 330 on the medial, posterior, lateral, and anterior aspects of the post 330. The articulation surface 331 may include a medial articulation surface 332, a lateral articulation surface 334, an anterior post surface 336, and a posterior articulation surface 342. The medial and lateral articulation surfaces 332, 334 may taper slightly inward from the post superior end 340 to the post base 338 of the post 330 relative to an insert midline vertical axis 2. However, some embodiments of CCK insert 312 may include no taper of the medial and lateral articulation surfaces 332, 334. The medial articulation surface 332 may be continuous with the medial condylar articulation surface 325, and the lateral articulation surface 334 may be continuous with the lateral condylar articulation surface 327. The anterior post surface 336 may extend between the medial and lateral surfaces 332, 334 and may be convexly rounded. The anterior post surface 336 may taper outward from the post superior end 340 to the post base 338 relative to the midline axis 2, as best seen in FIG. 12F. In other embodiments of the CCK insert 312, the anterior post surface 336 may include less taper, more taper, and/or no taper. The post 330 of the CCK insert 312 may be wider and bigger in diameter than the post 30 of PS insert 12, for example to provide increased stability in the case of removal of the collateral ligaments.

Referring to FIG. 12B, the boundary of the post superior end 340 may define a rounded rim 344 shaped as a portion of a circle, from a superior perspective. The post superior end 340 and rim 344 may be semi-circular as shown, however the rim 344 may define a circular envelope 347.

The post superior end 340 may be circular and rim 344 may provide increased surface contact and rotational range of motion when coupled and implanted with the PS femoral component 14 in comparison to traditionally shaped posts with a more square or rectangular shaped post. Thus, the rounded post superior end 340 and rim 344 may allow for surface contact with the femoral component 14 in contrast to the mere point or edge contact that is achieved by traditional posts that do not have these features. The CCK insert 312 may be coupled with the PS femoral component 14 to form a constrained condylar knee assembly, and this assembly may be implanted with a suitable tibial baseplate as a constrained condylar knee prosthesis. The CCK insert 312 may also be coupled with the CR femoral component 114 and implanted with a suitable tibial baseplate. Thus, all of the tibial inserts 12, 212, and 312 disclosed herein are interchangeable with both the CR femoral component 114 and the PS femoral component 14. FIG. 13 is a chart showing the potential combinations of components.

The tibial inserts 12, 212, 312, PS femoral component 14 and CR femoral component 114 may be grouped together as a modular knee replacement system and provided as a kit in one or more packages, in one non-limiting example. Another kit may include a CR femoral component 114, a PS insert 12 and a CR insert 212, in one or more packages in another non-limiting example. Yet another kit may include a PS femoral component 14, a PS insert 12, a CR insert 212, and a CCK insert 312, in one or more packages in yet another non-limiting example. However, it will also be understood that other kit embodiments may utilize any of the tibial inserts and/or femoral components described herein in any number or combination, in one or more packages. Furthermore, other components may also be including in any kit described herein, such as suitable tibial baseplate components, patellar components, etc., in one or more packages. It will also be understood that any of the tibial inserts disclosed herein may be formed of vitamin E polyethylene, highly cross linked polyethylene, ultra-high molecular weight polyethylene (UHMWPE), or any other suitable material.

Figure 14:
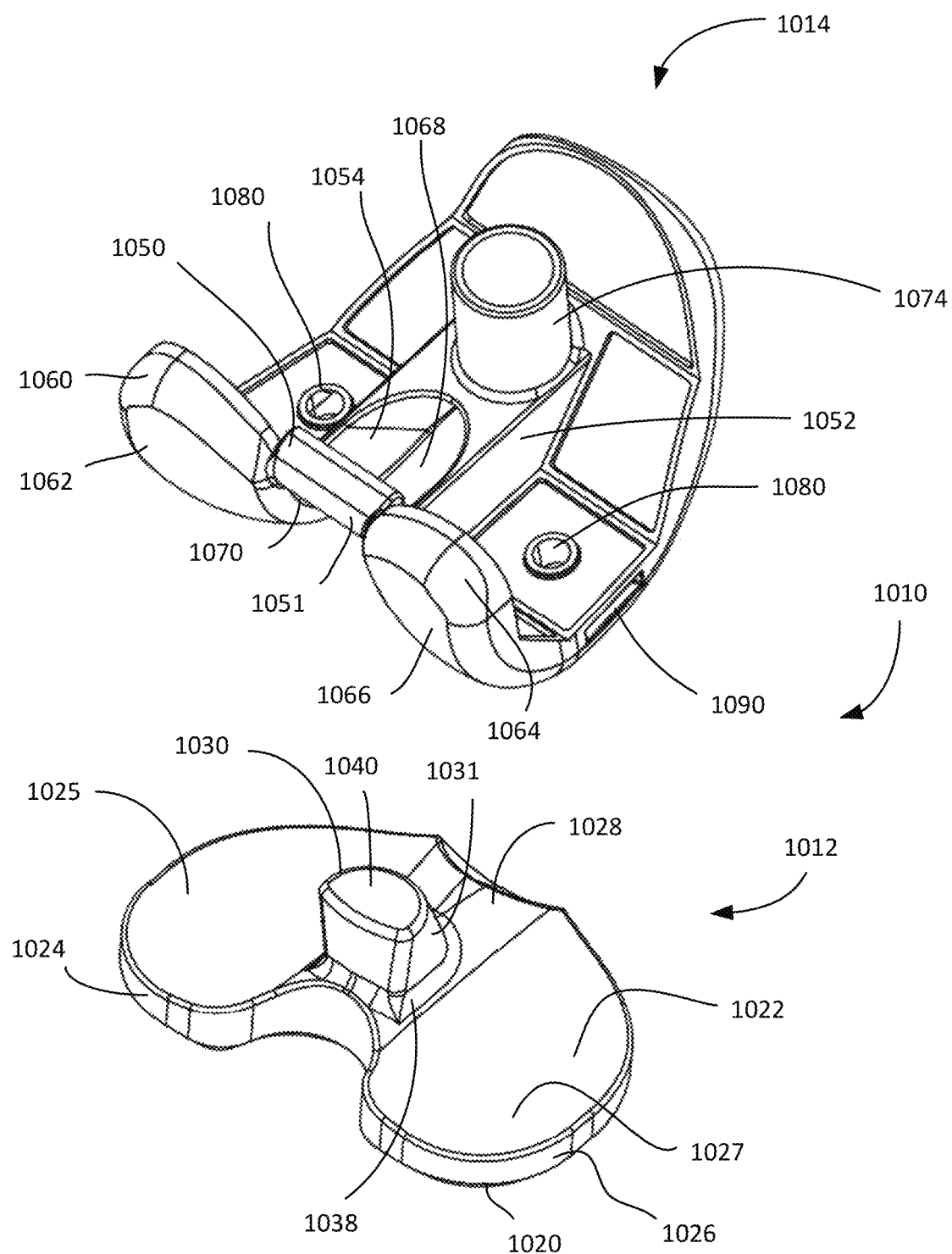
FIG. 14 is an exploded rear view of another assembly of the disclosure, including a posterior stabilizing femoral component and a posterior stabilizing tibial insert.
Figure 15:
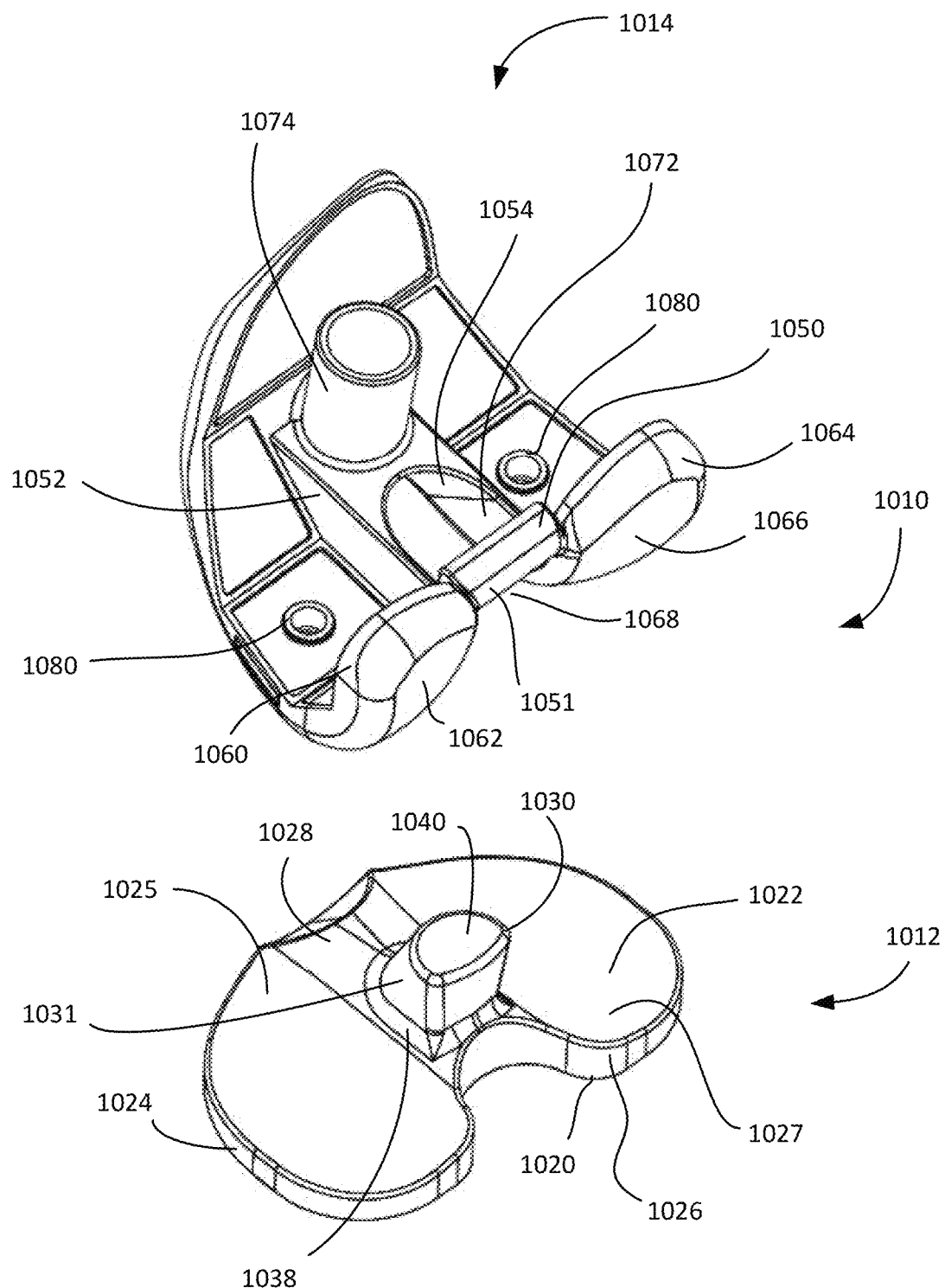
FIG. 15 is another exploded rear view of the assembly of FIG. 14.

Referring to FIGS. 14 and 15, another assembly 1010 of the disclosure for an implantable knee prosthesis is shown in various exploded rear views. The assembly 1010 may include a femoral component 1014 and a tibial insert 1012. The tibial insert 1012 may be further coupled to a tibial baseplate component (not shown) which may also be implanted in a prepared tibia of a patient (not shown). The femoral component 1014 and tibial insert 1012 illustrated in FIGS. 14 and 15 are right side femoral and tibial insert components. Left side femoral and tibial insert components would be mirror images of the right side femoral and tibial insert components that are shown in FIGS. 14 and 15. The femoral component 1014 may also be referred to as a posterior stabilizing femoral component 1014 (or "PS femoral component") and the tibial insert 1012 may also be referred to as a posterior stabilizing tibial insert (or "PS insert").

FIGS. 16A-16D show the PS insert 1012 of FIGS. 15 and 14 in isolation. The PS insert 1012 may include a fixation side 1020, which may be an inferior side, opposite an articulation side 1022, which may be a superior side. The articulation side 1022 may include a medial tibial compartment 1024 having a medial condylar articulation surface 1025 and a lateral tibial compartment 1026 having a lateral condylar articulation surface 1027. A central portion 1028 may separate the medial tibial compartment 1024 from the lateral tibial compartment 1026. A post 1030 may protrude superiorly from the central portion 1028 and extend from a post base 1038 to a post top 1040 or post superior end. From the anterior perspective (shown in FIG. 16B) and/or the posterior perspective (shown in FIG. 16A), the post 1030 may have its maximum medial-lateral or horizontal width toward the top 1040 of the post 1030, and its minimum medial-lateral or horizontal width toward the base 1038 of the post 1030. The post 1030 may also be bilaterally symmetrical from the anterior and/or posterior perspectives. A recess 1045 may be formed posterior to the central portion 1028, between the medial and lateral tibial compartments 1024, 1026, and may provide room for a posterior cruciate ligament (not shown). The PS insert 1012 may further include an insert base 1046, which may further include an engagement feature 1048 for engagement with a tibial baseplate component.

Figure 16A:
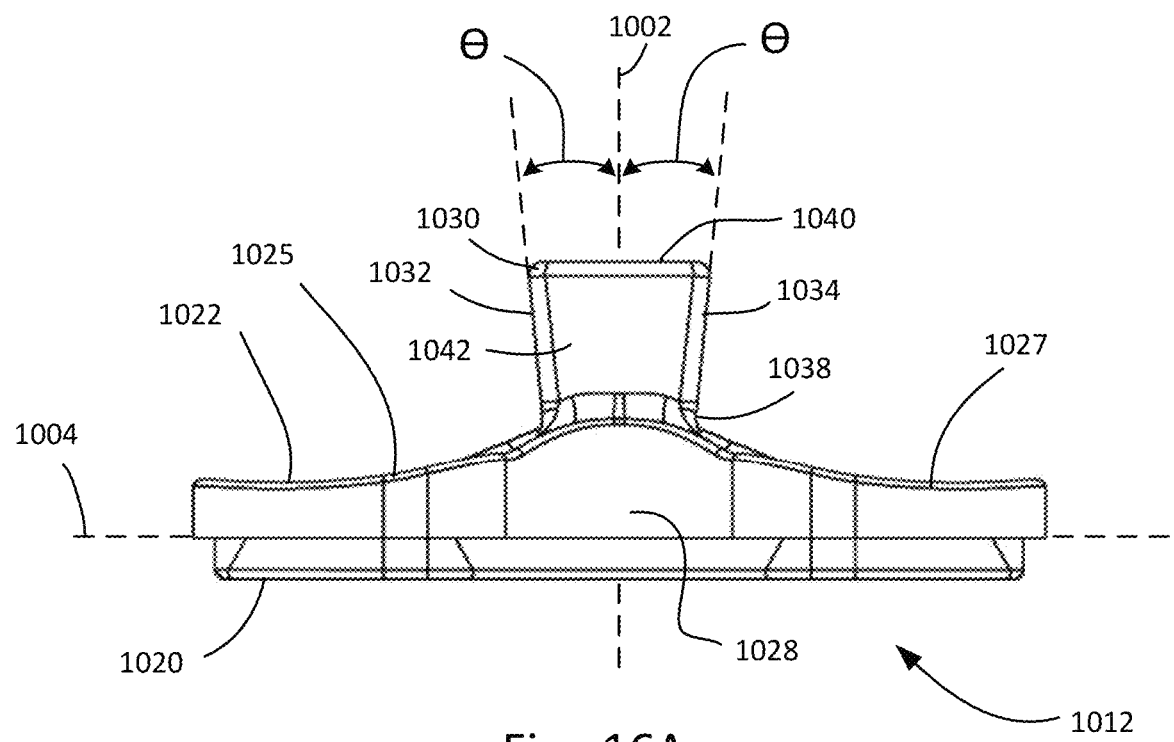
FIG. 16A is a posterior view of the tibial insert of FIG. 14.
Figure 16B:
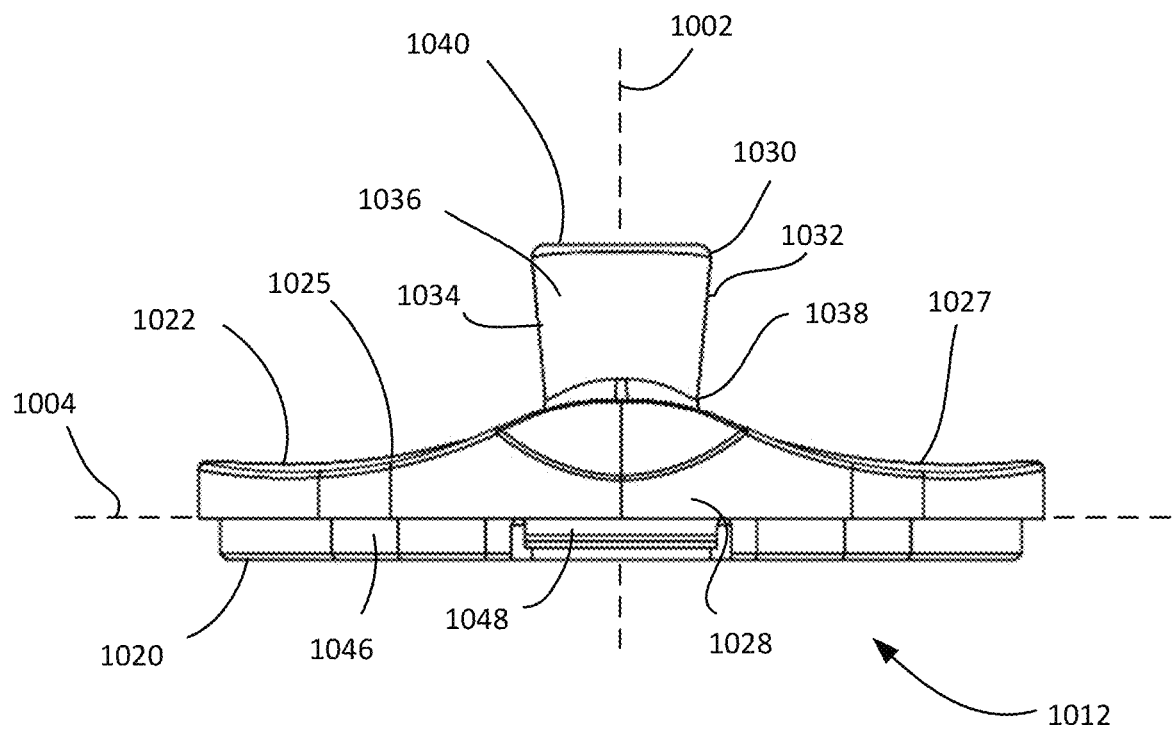
FIG. 16B is an anterior view of the tibial insert of FIG. 14.
Figure 16C:
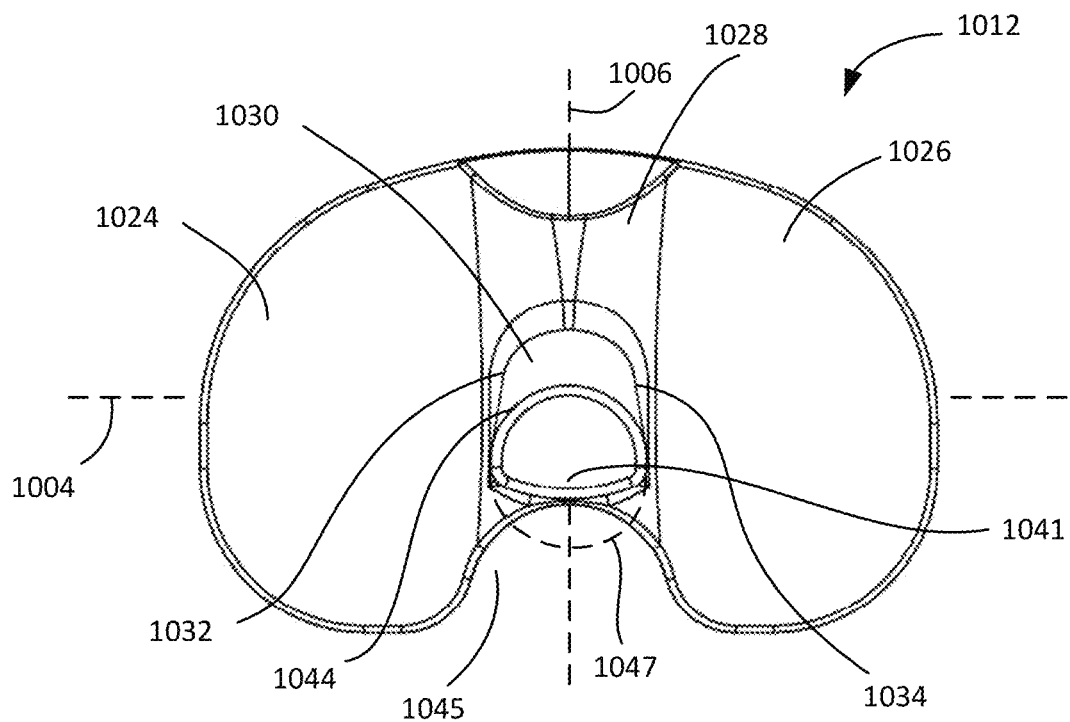
FIG. 16C is a superior view of the tibial insert of FIG. 14.
Figure 16D:
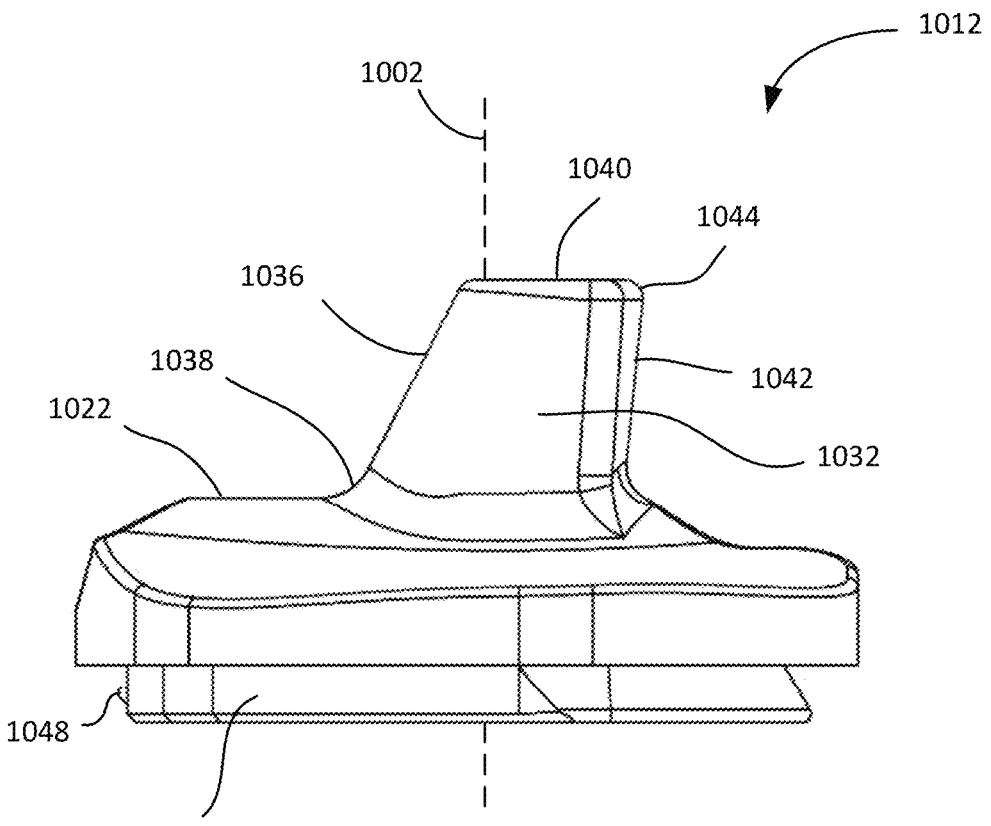
FIG. 16D is a medial side view of the tibial insert of FIG. 14.

Continuing with FIGS. 14-16D, the post 1030 may have an articulation surface 1031 extending around the post 1030 on the medial, posterior, lateral, and anterior aspects of the post 1030. The articulation surface 1031 may include a medial articulation surface 1032, a lateral articulation surface 1034, an anterior post surface 1036, and a posterior articulation surface 1042. The medial and lateral articulation surfaces 1032, 1034 may be non-parallel to one another and taper inward from the post superior end 1040 to the post base 1038 relative to an insert midline vertical axis 1002, as shown in FIGS. 16A and 16B. As shown in FIG. 16A, an angle θ between the vertical axis 1002 and each tapered surface 1032, 1034 may be about 6.5, in at least one embodiment. Since the post 1030 may be bilaterally symmetrical, the angle θ may be the same on both the medial and lateral sides 1032, 1034 of the post 1030. In other embodiments of the disclosure, angle θ may range from about 6° to 11° degrees. The medial articulation surface 1032 may be continuous with the medial condylar articulation surface 1025, and the lateral articulation surface 1034 may be continuous with the lateral condylar articulation surface 1027. The anterior post surface 1036 may extend between the medial and lateral surfaces 1032, 1034 and may be convexly rounded. The anterior post surface 1036 may also taper outward from the post superior end 1040 to the post base 38 relative to the insert midline vertical axis 1002, as best seen in FIG. 16D. In other embodiments of the PS insert 1012, the anterior post surface 1036 may include less taper, more taper, and/or no taper. A midline medial-lateral axis 1004 and a mid-line anterior-posterior axis 1006 are also shown.

Referring to FIG. 16C, the boundary of the superior end 1040 may define a rounded rim 1044 shaped as a portion of a circle defined by a circular envelope 1047, as seen from a superior perspective. The superior end 1040 and rim 1044 may have a convex protrusion 1041 toward a posterior end of the post 1030 as shown and may permit passage of the posterior cruciate ligament. The circular superior end 1040 with rim 1044 may provide increased rotational range of motion and surface contact against the femoral component 1014 in comparison to traditional posts with a more square or rectangular shape and no rim. Thus, the rounded superior end 1040 and rim 1044 may allow for greater surface contact with the femoral component 1014 in contrast to the mere point or edge contact that is achieved by traditional posts that do not have these features.

The PS femoral component 1014 depicted in FIGS. 14-15 may include augment fixation apertures 1080, impact driver apertures 1090, a cam element or cam bar 1050, and a box structure 1052 for providing posterior stabilization in place of absent ligaments. The cam bar 1050 may include a cam articulating surface 1051 which may contact the posterior articulation surface 1042 of the post 1030 during flexion. An internal articulation surface 1054 may reside on the inside of the box structure 1052 and may contact the post 1030 during articulation and rotation of the knee joint. The internal articulating surface 1054 may be concavely curved and may contact the rim 1044 of the post 1030 during axial rotation of the knee joint about the post 1030. The PS femoral component 1014 may further include a medial condyle 1060 having a medial condylar articulation surface 1062, and a lateral condyle 1064 having a lateral condylar articulation surface 1066. The medial and lateral condylar articulation surfaces 1062, 1066 may articulate against the PS insert 1012 medial and lateral articulation surfaces 1025, 1027, respectively. A gap 1068 may be formed between the medial and lateral condyles 1060, 1064, with the cam bar 1050 extending medial-laterally across the gap 1068. The internal articulation surface 1054 may include a medial portion 1070 continuous with a lateral portion 1072. In the embodiment depicted, a fixation post 1074 may protrude superiorly from the PS femoral component 1014. However, in other embodiments of the PS femoral component 1014, the fixation post 1074 may be absent and/or other fixation features such as posts, spikes, pegs, webs, keels, or teeth may be present to affix the PS femoral component 1014 to a prepared femur (not shown).

Figure 17:
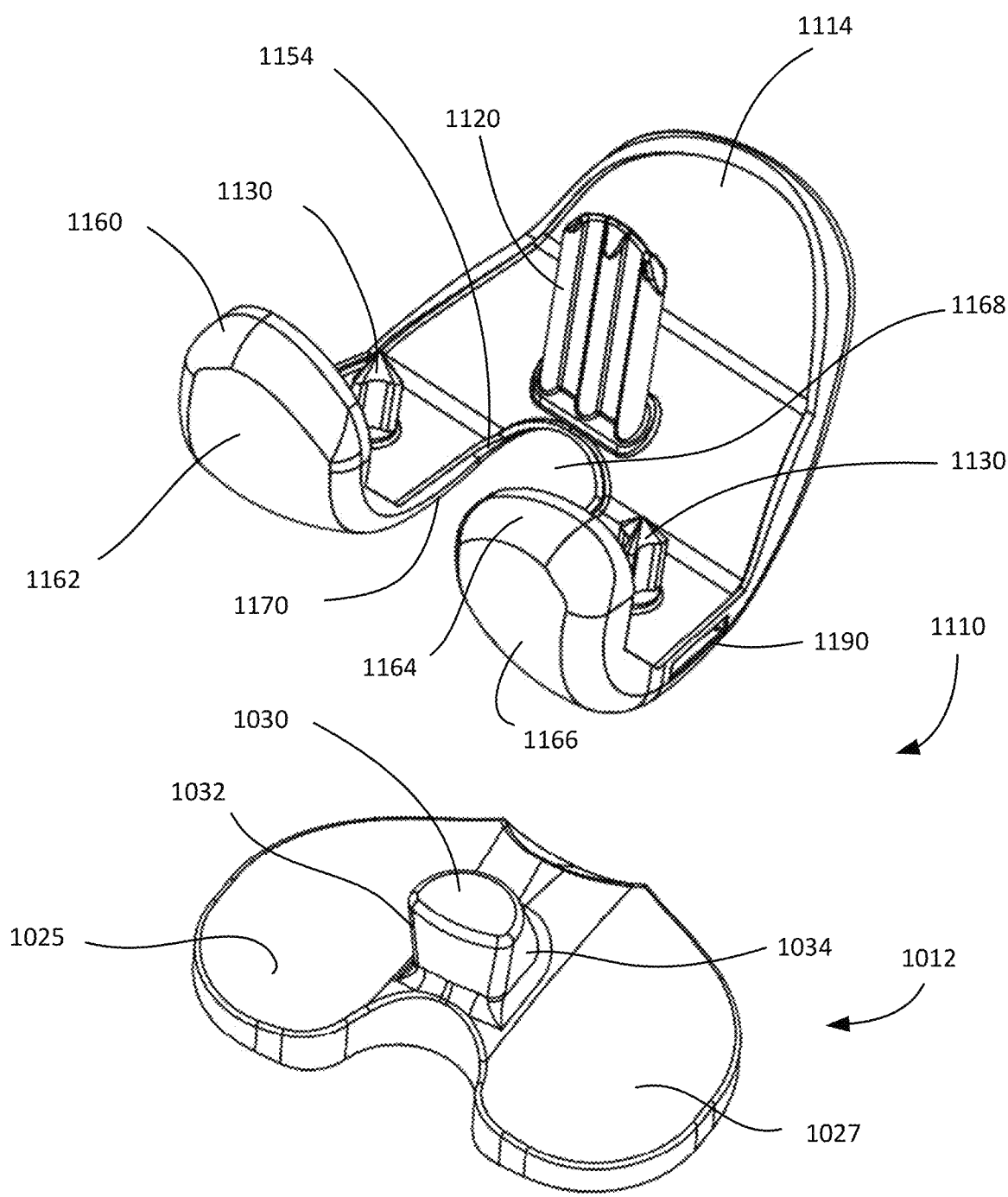
FIG. 17 is an exploded rear view of another assembly of the disclosure, including a cruciate retaining femoral component with a keel and the posterior stabilizing tibial insert of FIG. 14.
Figure 18:
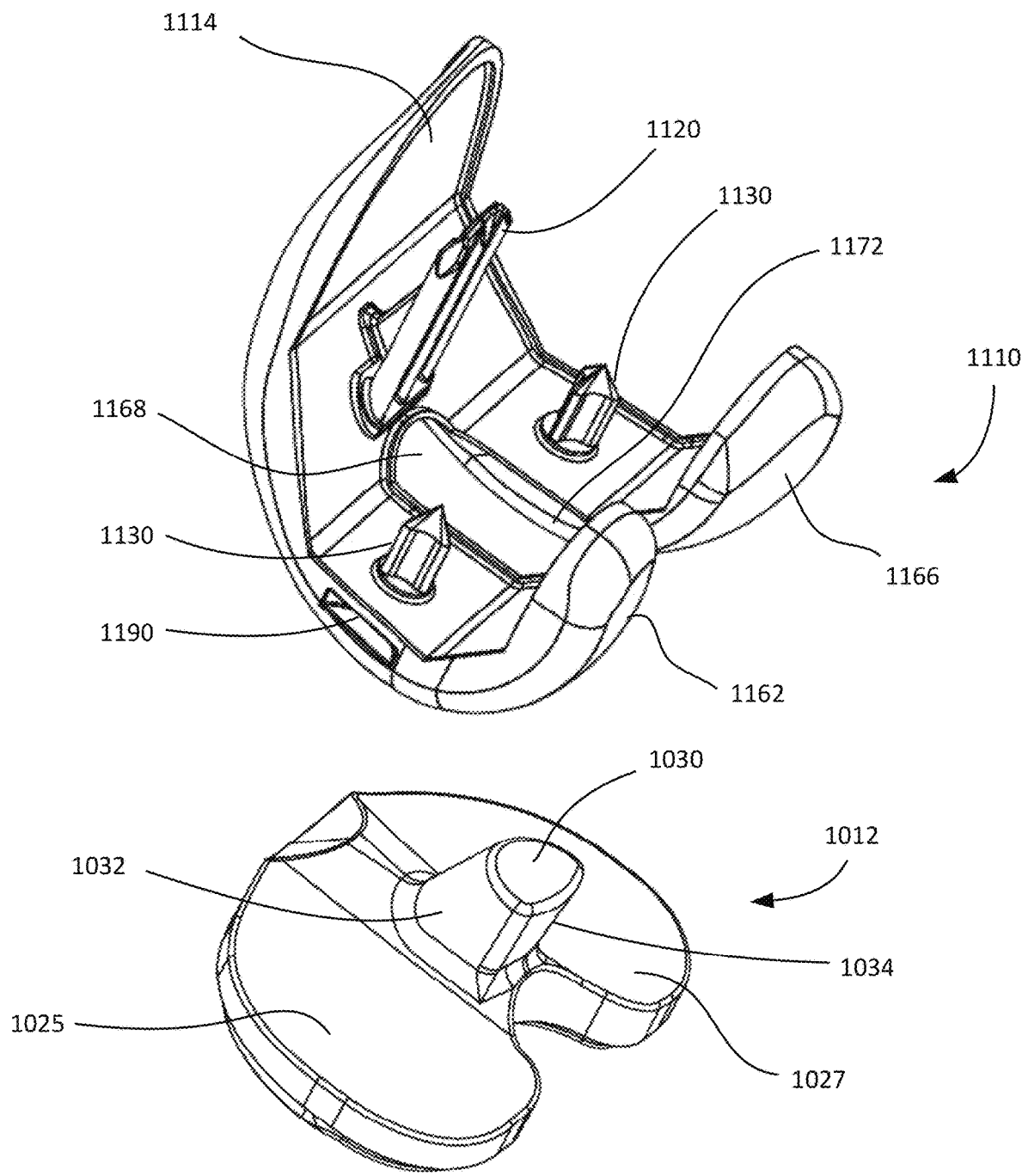
FIG. 18 is another exploded rear view of the assembly of FIG. 17.

Referring to FIGS. 17 and 18, another assembly 1110 embodiment of the disclosure may include the PS insert 1012 of FIGS. 14-16D coupled with a cruciate retaining femoral component 1114 (or "CR femoral component"). The CR femoral component 1114 may include a keel 1120, fixation members 1130, impact driver apertures 1190, and medial and lateral condyles 1160, 1164 with a gap 1168 formed between the condyles 1160, 1164. As a CR femoral component 1114, no cam bar or box may be present. The condyles 1160, 1164 may include medial and lateral condylar articulation surfaces 1162, 1166, and an internal articulation surface 1154 with medial and lateral portions 1170, 1172.

The tapered sides 1032, 1034 of the post 1030 may permit natural articulation of the CR femoral component 1114 with the PS insert 1012, which may not be achievable if the post 1030 were not tapered. For example, if the post 1030 had straight sides instead of tapered sides, the wider width of the post 1030 at the base of the post 1030 may interfere with the internal articulating surfaces 1170, 1172 of the condyles 1160, 1164. When the PS femoral component 1014 is coupled with the PS insert 1012 to form assembly 1010, as in FIGS. 14 and 15, the circular shape of the post superior end 1040 in combination with the tapered medial and lateral surfaces 1032, 1034 of the post 1030, may permit the PS femoral component 1014 to articulate relative to the PS insert 1012 in the manner of a posterior stabilized femoral component. However, when the PS insert 1012 is paired and implanted with the CR femoral component 1114, the resultant assembly 1110 may provide the native articulation and rotation of a cruciate retaining implant.

Figure 19:
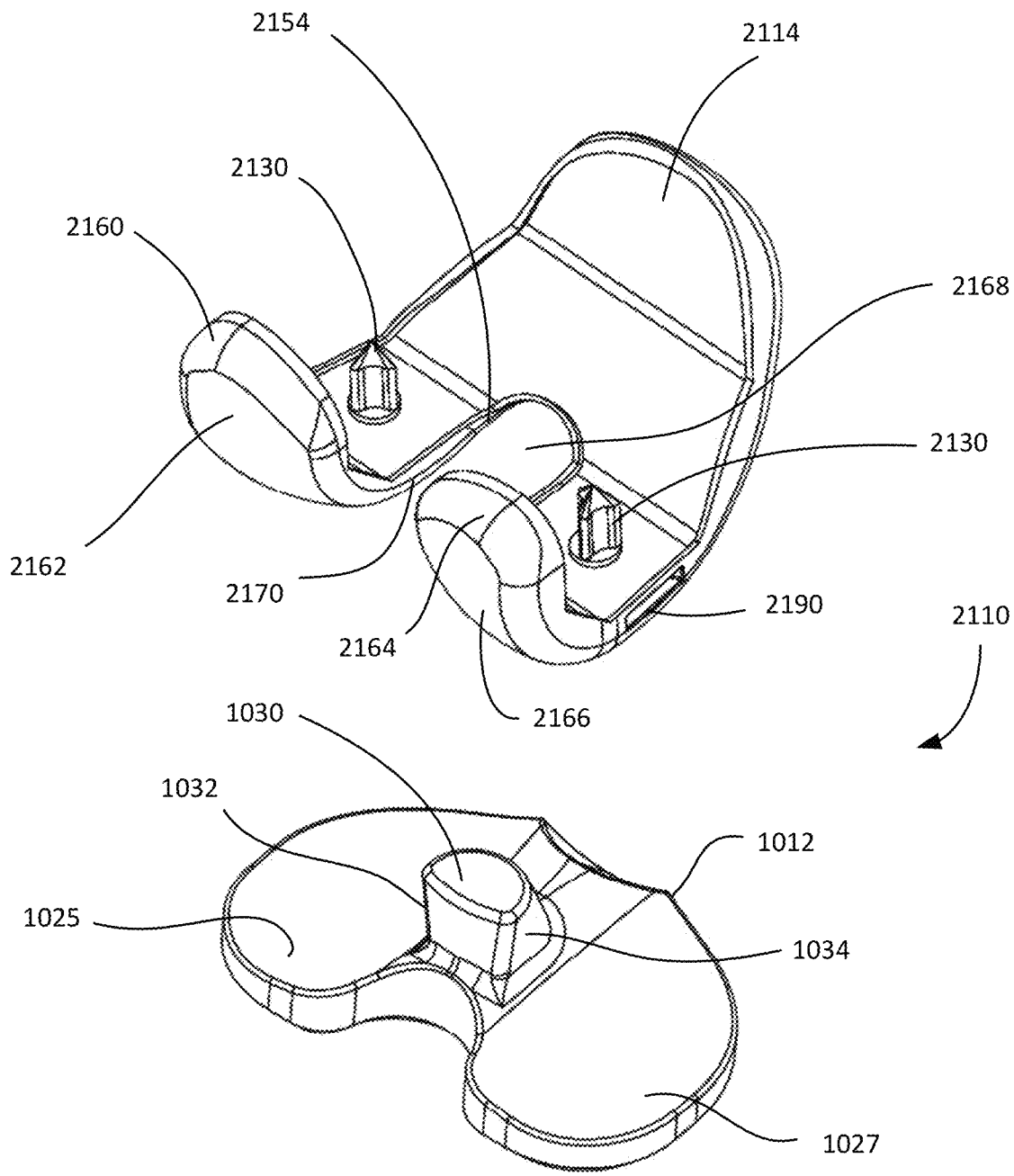
FIG. 19 is an exploded rear view of another assembly of the disclosure, including a cruciate retaining femoral component without a keel and the posterior stabilizing tibial insert of FIG. 14.
Figure 20:
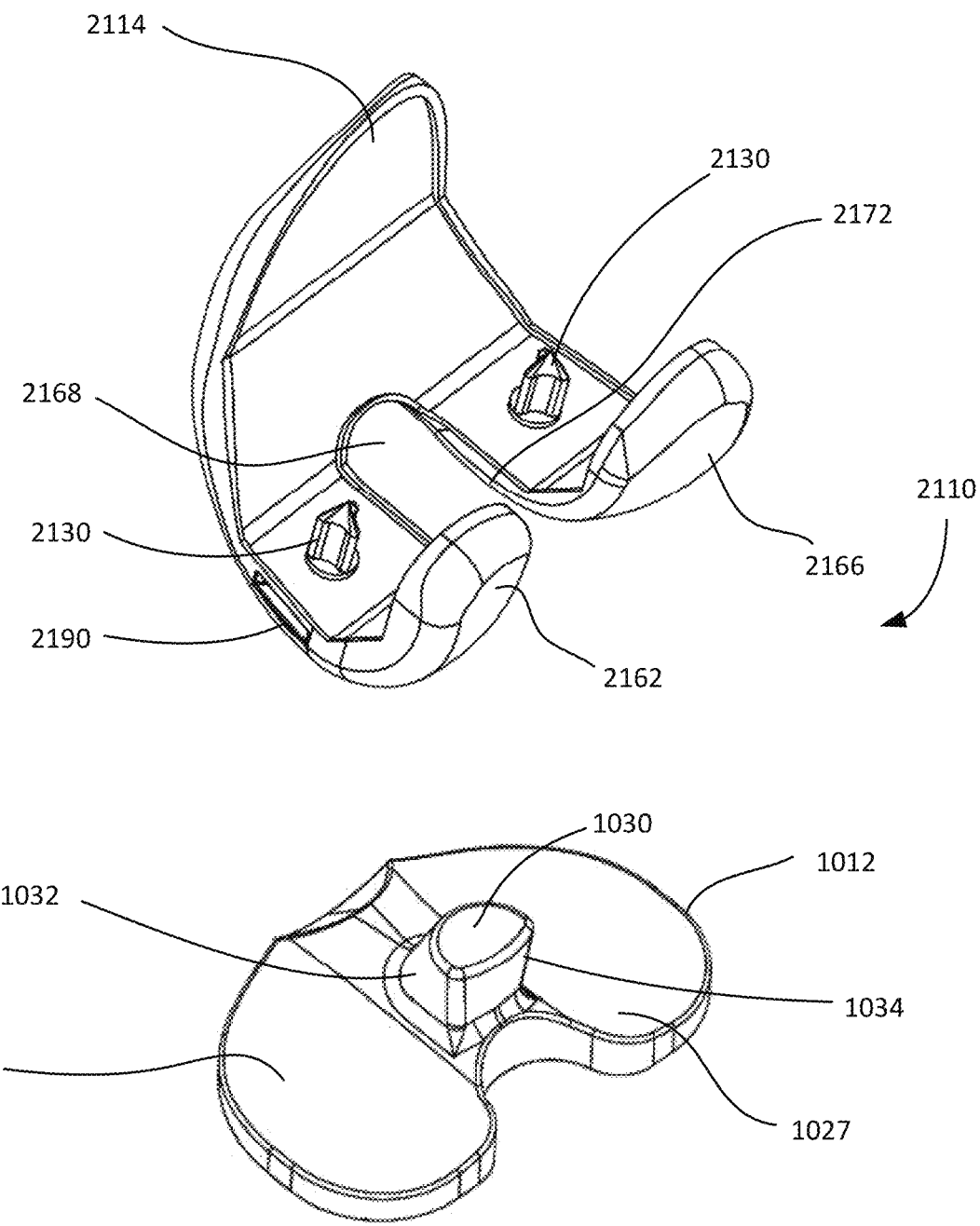
FIG. 20 is another exploded rear view of the assembly of FIG. 19.
Figure 21A:
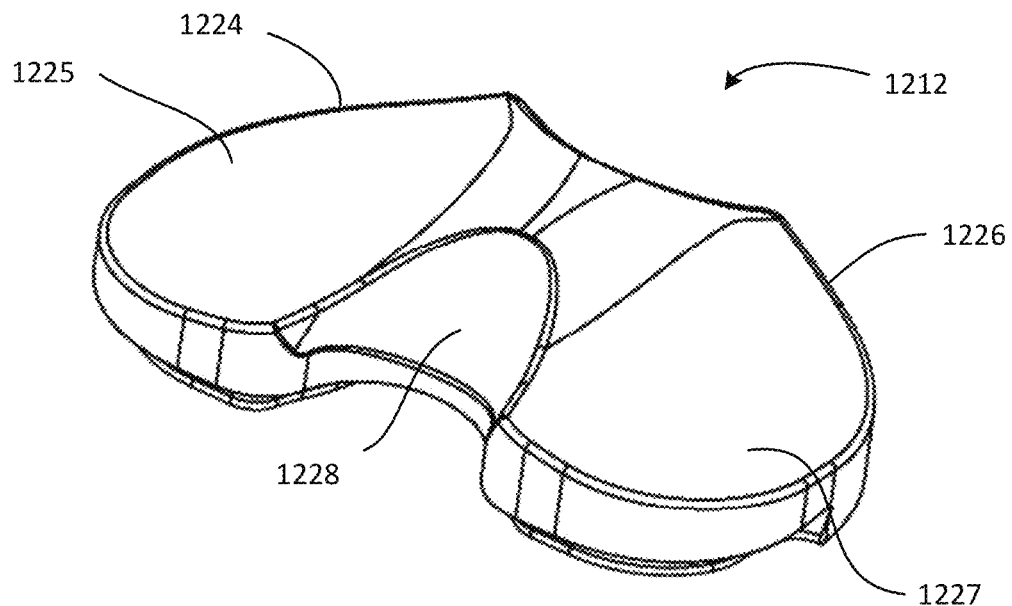
FIG. 21A is a perspective rear view of another tibial insert of the disclosure.
Figure 21B:
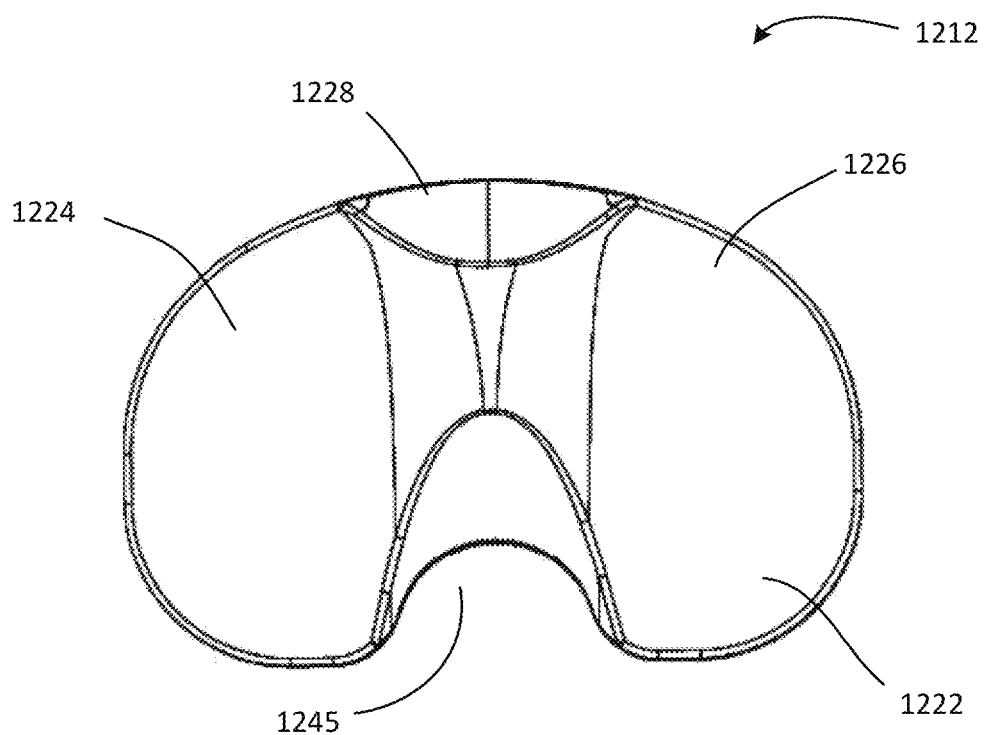
FIG. 21B is a top view of the tibial insert of FIG. 21A.
Figure 21C:
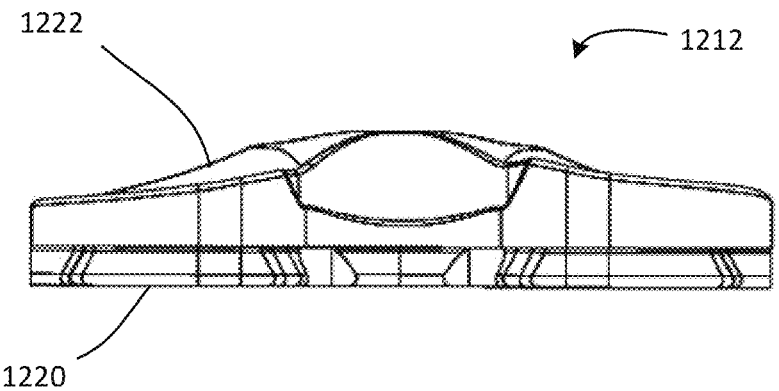
FIG. 21C is a posterior view of the tibial insert of FIG. 21A.
Figure 21D:
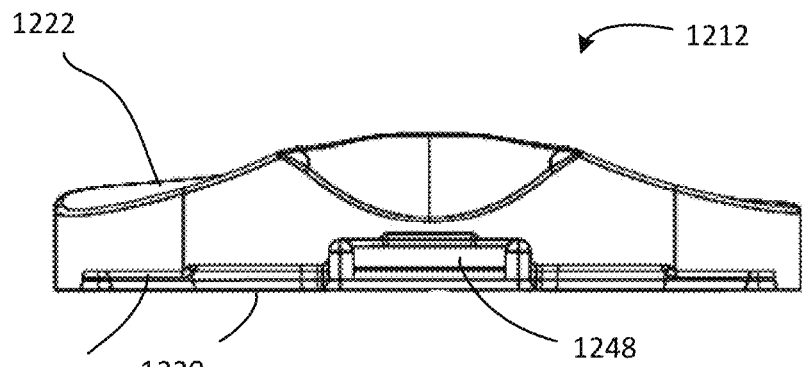
FIG. 21D is an anterior view of the tibial insert of FIG. 21A.
Figure 21E:
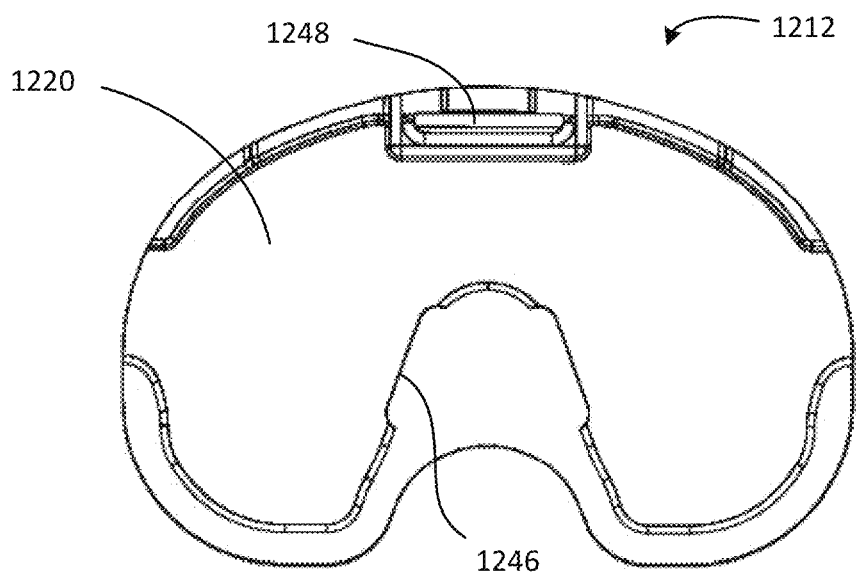
FIG. 21E is a bottom view of the R tibial insert of FIG. 21A.

Referring to FIGS. 19 and 20, another assembly 2110 embodiment of the disclosure may include the PS insert 1012 of FIGS. 14-16D coupled with a cruciate retaining femoral component 2114 (or "CR femoral component"). The CR femoral component 2114 may not include a keel, as opposed to the CR femoral component 1114 shown in FIGS. 17 and 18, and the CR femoral component 2114 may be configured for cemented and/or cementless fixation to a femoral bone. The CR femoral component 2114 may include fixation members 2130, impact driver apertures 2190, and medial and lateral condyles 2160, 2164 with a gap 2168 formed between the condyles 2160, 2164. As a CR femoral component 2114, no cam bar or box may be present. The condyles 2160, 2164 may include medial and lateral condylar articulation surfaces 2162, 2166, and an internal articulation surface 2154 with medial and lateral portions 2170, 2172.

The tapered sides 1032, 1034 of the post 1030 may permit natural articulation of the CR femoral component 2114 with the PS insert 1012, which may not be achievable if the post 1030 were not tapered. For example, if the post 1030 had straight sides instead of tapered sides, the wider width of the post 1030 at the base 1038 of the post 1030 may interfere with the medial and lateral portions 2170, 2172 of the internal articulation surface 2154 of the condyles 2160, 2164. When the PS femoral component 1014 is coupled with the PS insert 1012 to form assembly 1010, as in FIGS. 14 and 15, the circular shape of the post superior end 1040 in combination with the tapered medial and lateral surfaces 1032, 1034 of the post 1030, may permit the PS femoral component 1014 to articulate relative to the PS insert 1012 in the manner of a posterior stabilized femoral component. However, when the PS insert 1012 is paired and implanted with the CR femoral component 2114, the resultant assembly 2110 may provide the native articulation and rotation of a cruciate retaining implant.

Referring to FIGS. 21A-21E, an alternative embodiment of a tibial insert 1212 is shown. The tibial insert 1212 may be referred to as a cruciate retaining tibial insert 1212 (or "CR insert"). In a system of the disclosure, the CR insert 1212 may be implanted with the CR femoral components 114, 1114, 2114 and a tibial baseplate component (See FIG. 24A) to form a cruciate retaining knee prosthesis system. The CR insert 1212 may include a fixation side 1220, which may be an inferior side, opposite an articulation side 1222, which may be a superior side. The articulation side 1222 may include a medial tibial compartment 1224 having a medial condylar articulation surface 1225 and a lateral tibial compartment 1226 having a lateral condylar articulation surface 1227. A central portion 1228 may separate the medial tibial compartment 1224 from the lateral tibial compartment 1226. A recess 1245 may be formed posterior to the central portion 1228, between the medial and lateral tibial compartments 1224, 1226, and may provide room for a posterior cruciate ligament. The CR insert 1212 may further include an insert base 1246 and an engagement feature 1248 for engagement with a tibial baseplate component.

The CR insert 1212 may be coupled with CR femoral components 114, 1114, 2114 to form a cruciate retaining assembly. This cruciate retaining assembly may be implanted with a suitable tibial baseplate as a complete cruciate retaining knee prosthesis. The CR insert 1212 may also be coupled with PS femoral components 14, 1014 to form a posterior stabilizing assembly and implanted with a suitable tibial baseplate as a complete posterior stabilizing knee prosthesis.

Figure 22A:
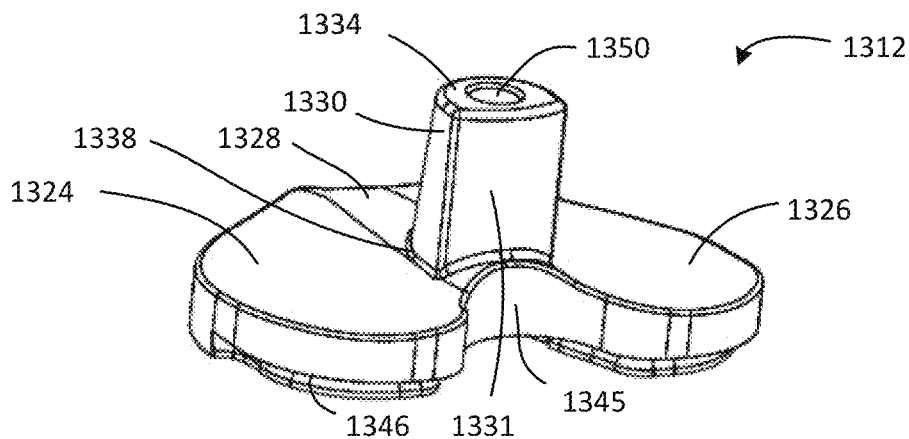
FIG. 22A is a perspective rear view of another tibial insert of the disclosure.
Figure 22B:
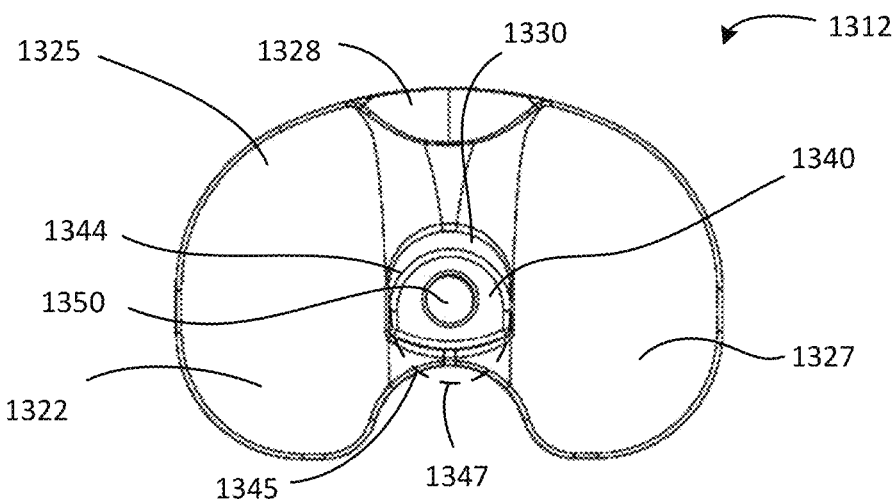
FIG. 22B is a top view of the tibial insert of FIG. 22A.
Figure 22C:
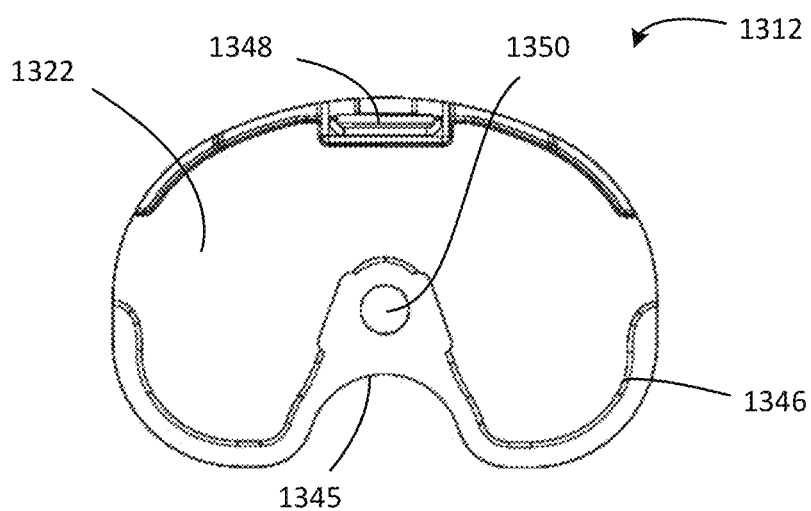
FIG. 22C is a bottom view of the tibial insert of FIG. 22A.
Figure 22D:
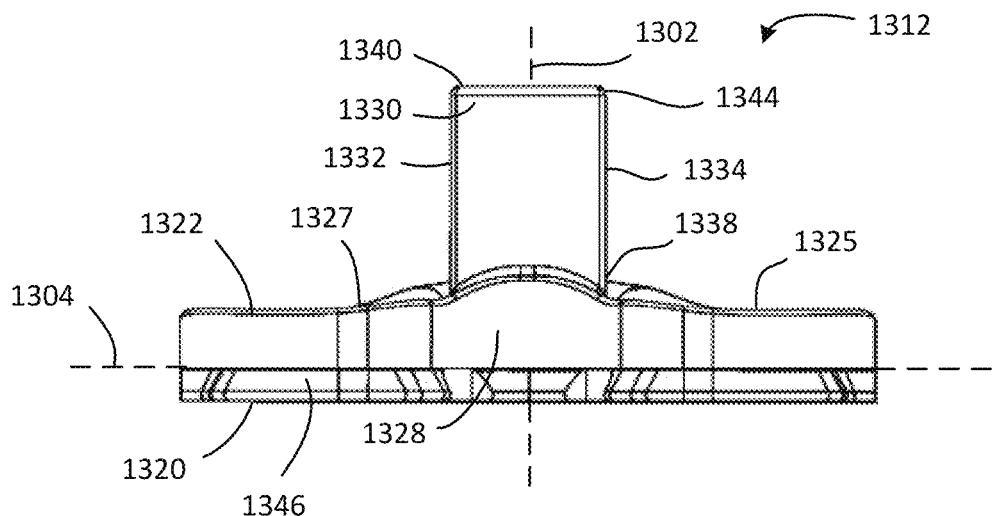
FIG. 22D is a posterior view of the tibial insert of FIG. 22A.
Figure 22E:
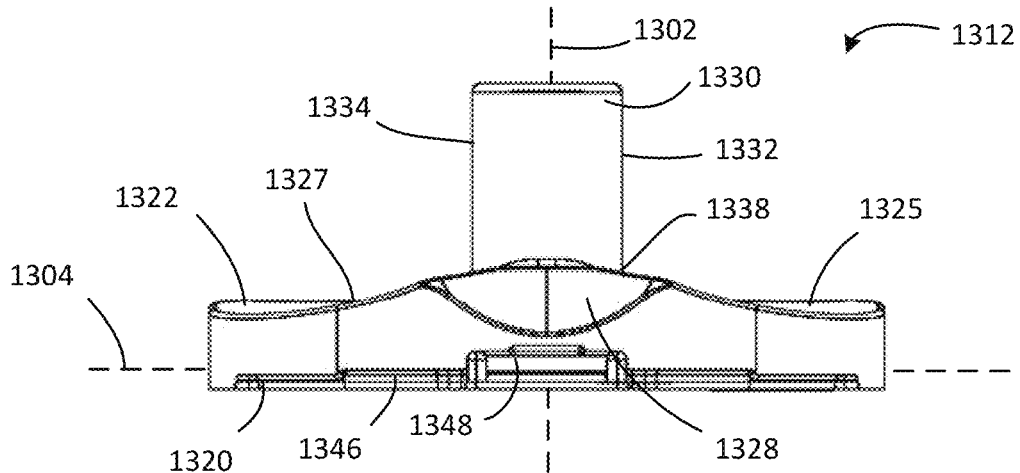
FIG. 22E is an anterior view of the tibial insert of FIG. 22A.

Referring to FIGS. 22A-22F, another alternative embodiment of a tibial insert 1312 is shown. The tibial insert 1312 may be referred to as a constrained condylar knee (CCK) tibial insert 1312 (or "CCK insert"). The CCK insert 1312 may include a fixation side 1320, which may be an inferior side, opposite an articulation side 1322, which may be a superior side. The articulation side 1322 may include a medial tibial compartment 1324 having a medial condylar articulation surface 1325 and a lateral tibial compartment 1326 having a lateral condylar articulation surface 1327. A central portion 1328 may separate the medial tibial compartment 1324 from the lateral tibial compartment 1326. A post 1330 may protrude superiorly from the central portion 1328 and extend from a post base 1338 to a top, or post superior end 1340. From the anterior perspective, as shown in FIG. 22E, and the posterior perspective, as shown in FIG. 22D, the post 1330 may have its maximum medial-lateral or horizontal width at the post superior end 1340 of the post 1330, and its minimum medial-lateral or horizontal width at the post base 1338 of the post 1330. The post 1330 may be bilaterally symmetrical from the anterior and posterior perspectives. The CCK insert 1312 may further include a posterior recess 1345, an insert base 1346, and an engagement feature 1348 for engagement with a tibial tray (not shown). An opening 1350 may be present in the superior surface of the post 1330.

Figure 22F:
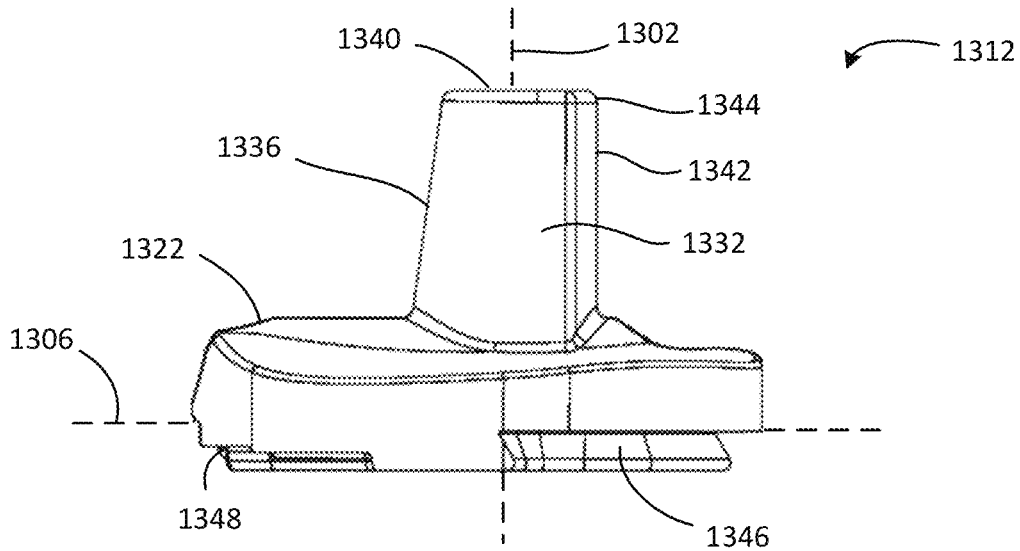
FIG. 22F is a medial side view of the tibial insert of FIG. 22A.

The post 1330 may have an articulation surface 1331 extending around the post 1330 on the medial, posterior, lateral, and anterior aspects of the post 1330. The articulation surface 1331 may include a medial articulation surface 1332, a lateral articulation surface 1334, an anterior post surface 1336, and a posterior articulation surface 1342. The medial and lateral articulation surfaces 1332, 1334 may taper slightly inward from the post superior end 1340 to the post base 1338 of the post 1330 relative to an insert midline vertical axis 1302. However, some embodiments of CCK insert 1312 may include less taper, more taper, and/or no taper of the medial and lateral articulation surfaces 1332, 1334. The medial articulation surface 1332 may be continuous with the medial condylar articulation surface 1325, and the lateral articulation surface 1334 may be continuous with the lateral condylar articulation surface 1327. The anterior post surface 1336 may extend between the medial and lateral articulation surfaces 1332, 1334 and may be convexly rounded. The anterior post surface 1336 may taper outward from the post superior end 1340 to the post base 1338 relative to the midline axis 1302, as best seen in FIG. 22F. In other embodiments of the CCK insert 1312, the anterior post surface 1336 may include less taper, more taper, and/or no taper. The post 1330 of the CCK insert 1312 may be wider and bigger in diameter than the post 30 of PS insert 12, for example to provide increased stability in the case of removal of the collateral ligaments. A midline medial-lateral axis 1304 and a mid-line anterior-posterior axis 1306 are also shown in FIGS. 22D through 22F.

Referring to FIG. 22B, the boundary of the post superior end 1340 may define a rounded rim 1344 shaped as a portion of a circle, from a superior perspective, and may have a convex protrusion toward a posterior end of the post 1330. The post superior end 1340 and rim 1344 may be semicircular as shown, however the rim 1344 may define a circular envelope 1347. The post superior end 1340 may be circular and the rim 1344 may provide increased surface contact and rotational range of motion when coupled and implanted with the PS femoral components disclosed herein in comparison to traditionally shaped posts with a more square or rectangular shaped post. Thus, the rounded post superior end 1340 and rim 1344 may allow for greater surface contact with the femoral components 14, 1014 in contrast to the mere point or edge contact that is achieved by traditional posts that do not include these features.

The CCK insert 1312 may be coupled with the PS femoral components 14, 1014 to form a constrained condylar knee assembly, and this assembly may be implanted with a suitable tibial baseplate as a constrained condylar knee prosthesis. The CCK insert 1312 may also be coupled with any of the CR femoral components disclosed herein and implanted with a suitable tibial baseplate. Thus, all of the tibial inserts disclosed herein are interchangeable with all of the CR and PS femoral components disclosed herein.

Any of the tibial inserts, CR femoral components, and/or PS femoral components ON disclosed herein may be grouped together in any number or combination as one or more modular knee replacement systems or kits. A particular kit may include a CR femoral component, a PS insert, and a CR insert. Yet another particular kit may include a PS femoral component, a PS insert, a CR insert, and a CCK insert. Suitable tibial baseplate components may also be included with any kit. Moreover, any of the tibial inserts disclosed herein may be formed of vitamin E polyethylene, highly cross linked polyethylene, ultra-high molecular weight polyethylene (UHMWPE), and/or the like.

Figure 23A:
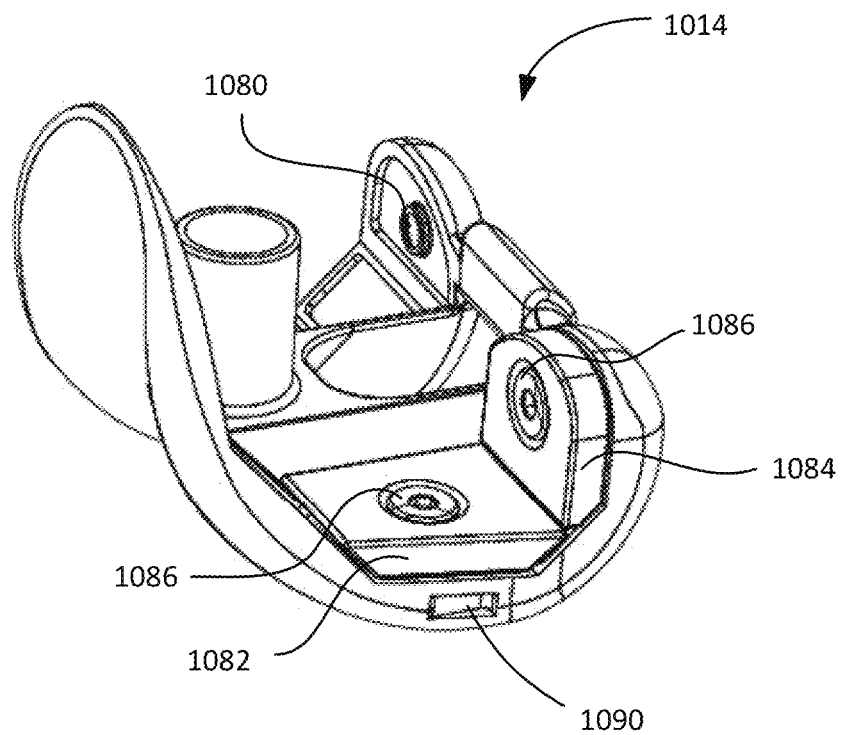
FIG. 23A is a perspective front view of the femoral component of FIG. 14 coupled to one or more augments.
Figure 23B:
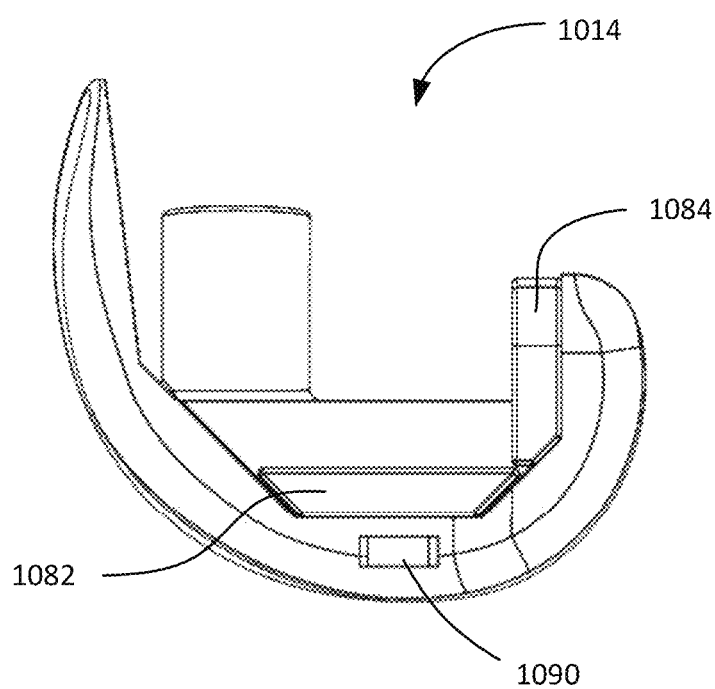
FIG. 23B is a medial side view of the femoral component of FIG. 23A.

Referring now to FIGS. 23A-B, FIG. 23A is a perspective front view of the femoral component 1014 of FIG. 14 coupled to one or more augments 1082, 1084 of the present disclosure and FIG. 23B is a medial side view of the femoral component 1014 of FIG. 23A. As briefly mentioned above with reference to FIGS. 14 and 15, the femoral component 1014 may include augment fixation apertures 1080 that may be configured to secure the one or more augments 1082, 1084 to the femoral component 1014, as well as impact driver apertures 1090 configured to receive a femoral component impact driver tool (not shown) to allow a surgeon to press fit the femoral component 1014 to the end of a prepared femur. The augments 1082, 1084 may be secured to the femoral component 1014 with fixation members 1086 and the augments 1082, 1084 may generally act to replace missing and/or compromised femoral bone and allow the femoral component 1014 to be adequately secured to a femoral bone under such conditions.

Figure 24A:
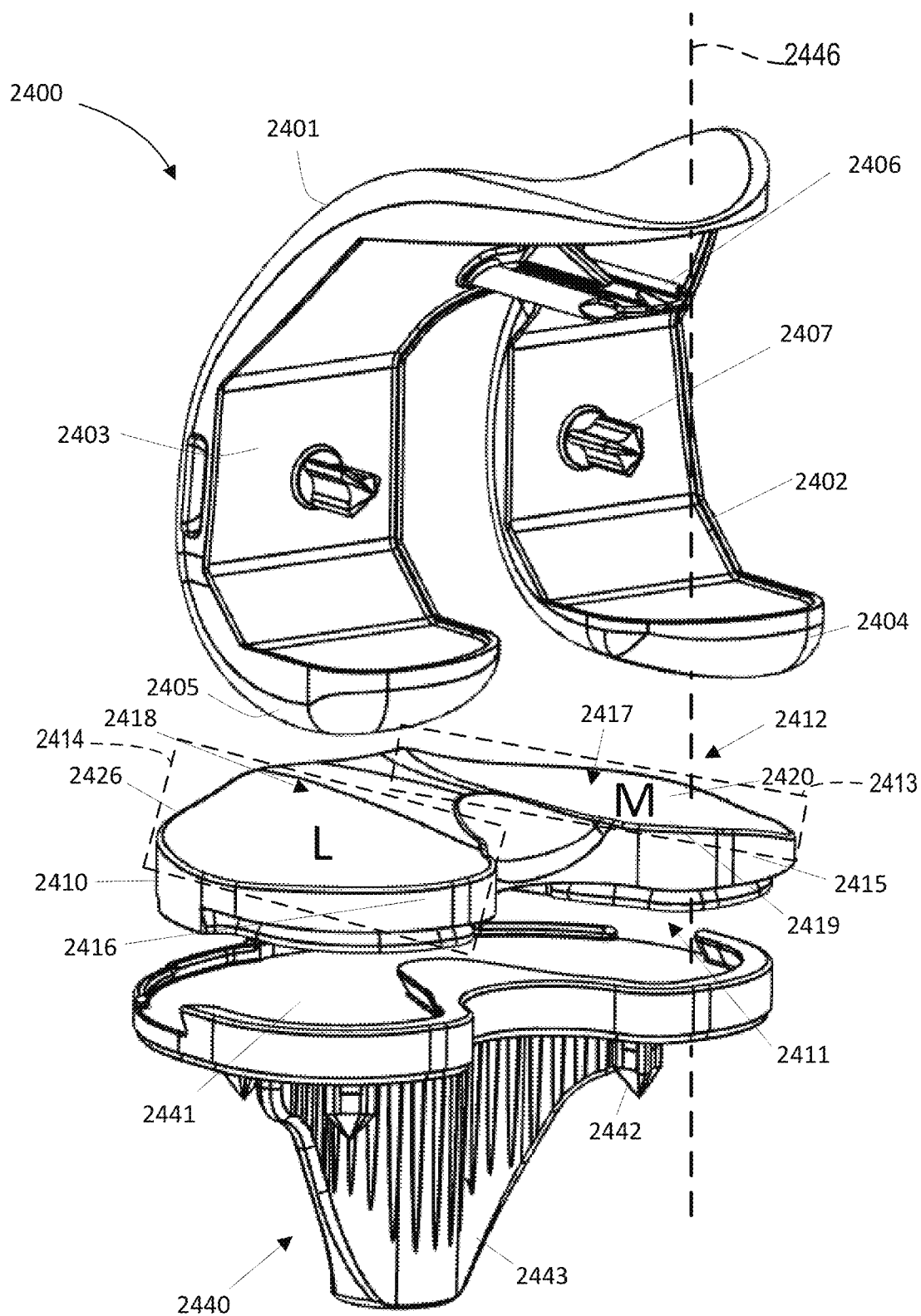
FIG. 24A is a posterior exploded view of a knee prosthesis assembly with an asymmetric tibial insert.

Referring to FIGS. 24A to 24F, an assembly 2400 for an implantable knee prosthesis is shown, according to another embodiment. Assembly 2400 may include a femoral component 2401, an insert 2410, and a tibial baseplate component 2440. FIG. 24A is an exploded view of the assembly 2400 approaching the assembly 2400 from a posterior-lateral side, in reference to the anatomy of a patient. The assembly 2400 is generally asymmetric across the medial and lateral sides, in other words the left side is asymmetric compared to the right side. In FIGS. 24 to 27, a left knee design is shown, and FIGS. 28A-28F illustrate a right knee design. In either a left or right configuration, medial will be proximal to the sagittal plane, or on the inside of the knee, and lateral is distal from the sagittal plane, or outside of the knee.

The femoral component 2401 may be posterior stabilizing or cruciate retaining. In FIG. 24A, the femoral component 2401, the tibial insert 2410, and the tibial baseplate component 2440 are shown in flexion. The femoral component 2401 may include medial condyle 2402 and lateral condyle 2403, similar to femoral component 114 in FIG. 9. The femoral component 2401 having a medial femoral compartment that includes the medial condylar articulation surface 2404 and a lateral femoral compartment that includes the lateral condylar articulation surface 2405. In certain embodiments, the medial condylar articulation surface 2404 defines the medial femoral compartment and the lateral condylar articulation surface 2405 defines the lateral femoral compartment.

The femoral component 2401 includes a femoral articulation surface that includes a medial condylar articulation surface 2404 and lateral condylar articulation surface 2405. In certain embodiments, the femoral articulation surface may include one of the medial condylar articulation surface 2404 and the lateral condylar articulation surface 2405. In other embodiments, the femoral articulation surface may include both of the medial condylar articulation surface 2404 and the lateral condylar articulation surface 2405.

The medial 2402 and lateral 2403 condyles may include the medial condylar articulation surface 2404 and the lateral condylar articulation surface 2405. The femoral component 2401 may include elements to secure the femoral component 2401 in the femur of the patient. For example, the femoral component 2401 may include at least one keel 2406 and at least one post 2407 that penetrate the bone of the associated femur (not shown) to secure the femoral component 2401 to the femur. The at least one post 2407 may be placed on the femoral side of the medial condyle 2402 and/or the lateral condyle 2403. The femoral component 2401 may include surface texturing on the bone-facing side to encourage bone in-growth and securement.

The tibial baseplate component 2440 may be configured to be secured to the tibia of the patient. As used herein, "baseplate" refers to a structure, component, apparatus, or device that serves as a foundation or frame for other structures, components, apparatuses, or devices that may be coupled or connected to the baseplate. In certain embodiments, a baseplate may have a generally planar structure.

The tibial baseplate component 2440 may include an insert interface 2441 configured for the placement and securement of the insert 2410, with one or more tibial posts 2442, which R may be inserted and secured into a patient's tibia. The tibial baseplate component 2440 may further have a base 2443, which may also be designed to penetrate the tibial plateau and may receive a separate keel (not shown) that penetrates more deeply into the intramedullary canal of the tibia. As used herein, a "base" refers to a main or central structure, component, or part of a structure. A base is often a structure, component, or part upon which, or from which other structures extend, are coupled to, or connect to. A base may have a variety of geometric shapes and configurations. A base may be rigid or pliable. A base may be solid or hollow. In one embodiment, a base may include a housing, frame, or framework for a larger system, component, structure, or device. In certain embodiments, a base can be a part at the bottom or underneath a structure designed to extend vertically when the structure is in a desired configuration or position.

FIG. 24A shows the exploded assembly 2400 from a lateral side configured for placement in a left knee and shown in approximately 90 degree extension, or "flexion." While the tibial baseplate component 2440 and the femoral component 2401 may be medially and laterally symmetric across an anterior-posterior plane, the insert 2410 may be medially-laterally asymmetric. The insert 2410 may include a fixation side or insert interface 2411 configured to mate or engage with the insert interface 2441 of the tibial baseplate component 2440. The insert interface 2411 may have features complementary to features on the insert interface 2441. The complementary features may allow for a removable fit for the insert 2410. The removable fit may allow for a modular assembly 2400, benefitting the surgeon and the patient.

In some embodiments, the tibial baseplate component 2440 and the femoral component 2401 may be symmetric, as mentioned previously, enabling them to be used for either left or right knee replacements. Only the insert 2410 may be specific to one side or the other. An assembly for either left or right knee arthroplasty may include only one femoral component 2401, one tibial baseplate component 2440, and two (e.g., left and right) inserts 2410. This may greatly reduce the inventory requirements for the system.

Opposite the insert interface 2411, the insert 2410 has a tibial articulation surface 2412 configured for engagement with the medial 2402 and lateral 2403 condyles on the femoral component 2401. The tibial articulation surface 2412 may include a medial tibial compartment 2413 and a lateral tibial compartment 2414. The medial tibial compartment 2413 may include a medial articulation surface 2420 for direct engagement with the medial condylar articulation surface 2404. The lateral tibial compartment 2414 may include a lateral articulation surface 2421 for direct engagement with the lateral condylar articulation surface 2405. The medial condylar articulation surface 2404 may engage with the medial articulation surface 2420 at a medial dwell point 2435. As used herein, "dwell point" refers to a point or an area where two articular surfaces contact each other during flexion and/or extension of a joint.

The lateral condylar articulation surface 2405 may engage with the lateral articulation surface 2421 at a lateral dwell point 2436 (shown in subsequent figures). The medial articulation surface 2420 may include a medial ramp 2419, which may have no counterpart on the lateral articulation surface 2421 and may create at least part of the asymmetry between the medial tibial compartment 2413 and the lateral tibial compartment 2414.

Figure 24B:
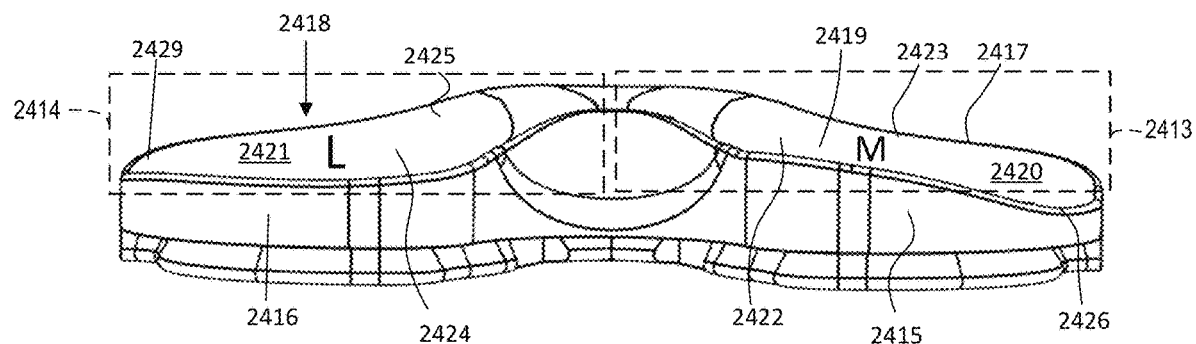
FIG. 24B is a posterior view of the asymmetric tibial insert of FIG. 24A.
Figure 24C:
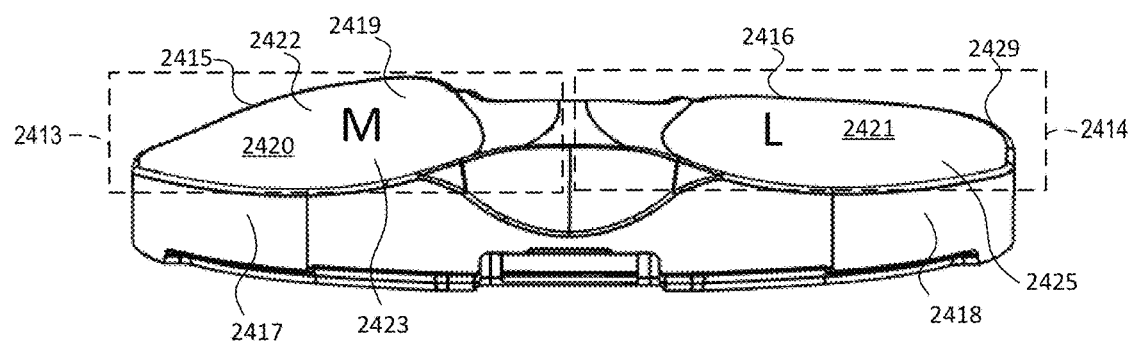
FIG. 24C is an anterior view of the asymmetric tibial insert of FIG. 24A.
Figure 24D:
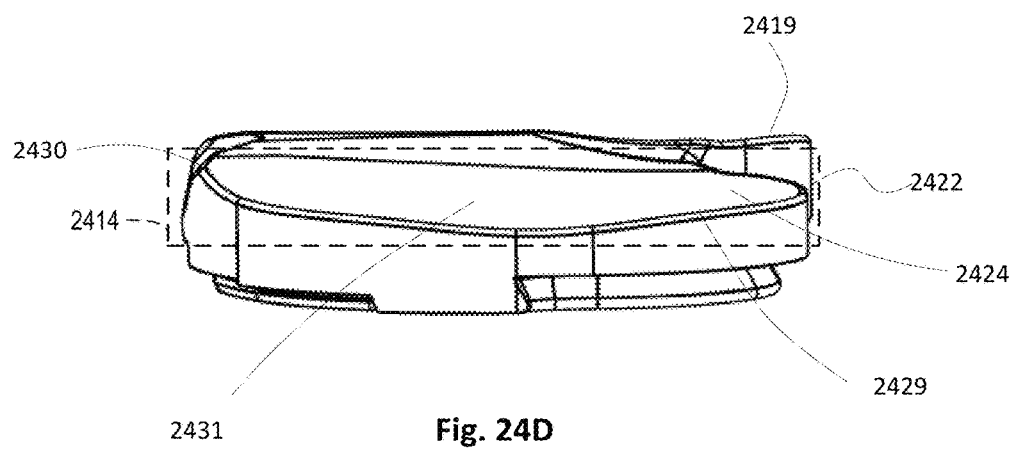
FIG. 24D is a lateral view of the asymmetric tibial insert of FIG. 24A.

FIGS. 24B-24D show details of the shape of the insert 2410. FIG. 24B is a posterior view of the insert 2410. FIG. 24C is an anterior view of the insert 2410. The lateral tibial compartment 2414 may include a lateral posterior side 2416 and a lateral anterior side 2418. The lateral articulation surface 2421 may include a lateral posterior section 2424 and a lateral anterior section 2425 surrounded by a lateral perimeter 2429. The medial tibial compartment 2413 may include a medial posterior side 2415 and a medial anterior side 2417. The medial articulation surface 2420 may include a medial posterior section 2422 and a medial anterior section 2423 surrounded by a medial perimeter 2426.

Figure 24E:
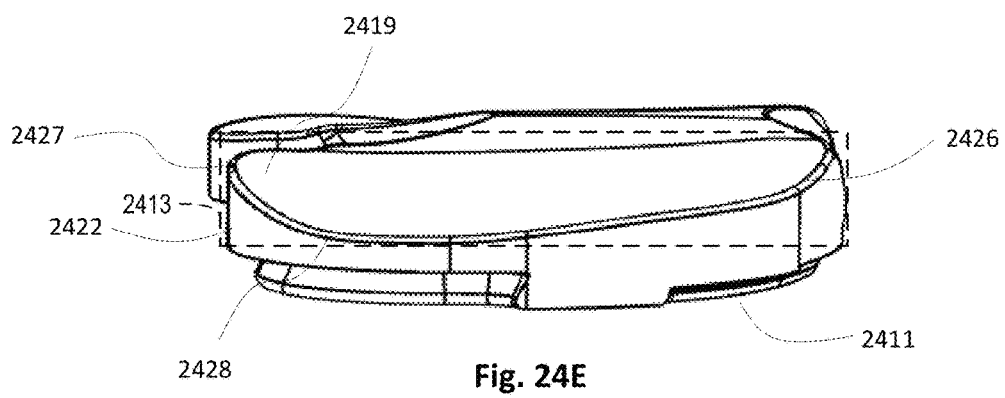
FIG. 24E is a medial view of the asymmetric tibial insert of FIG. 24A.
Figure 24F:
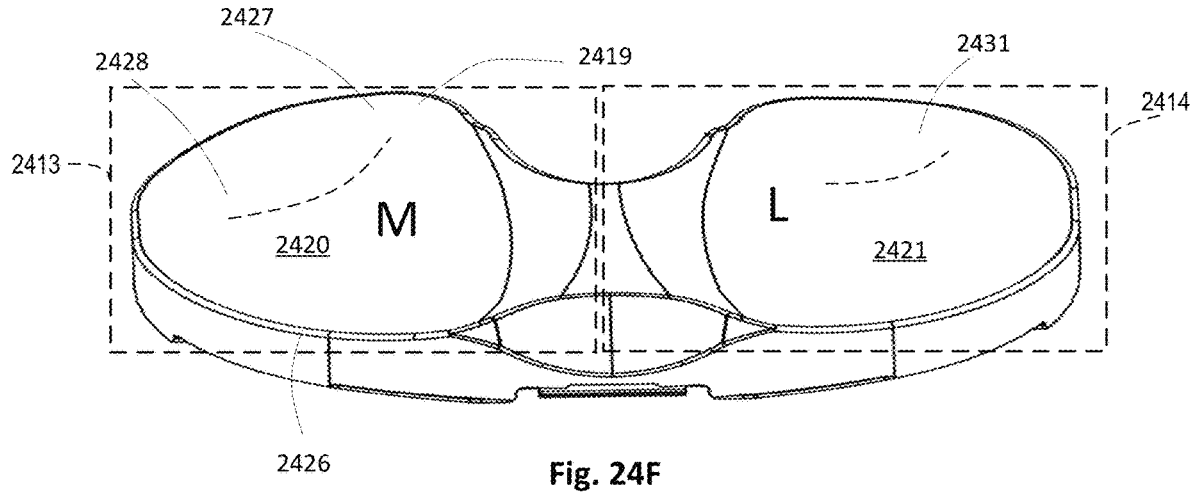
FIG. 24F is an anterior perspective view of the asymmetric tibial insert of FIG. 24A.

FIGS. 24D and 24E show lateral and medial views of the insert 2410, respectively. In 24D, the lateral tibial compartment 2414 with lateral perimeter 2429 is shown. The lateral articulation surface 2421 may meet the lateral perimeter 2429 at a lateral high point 2430. The lateral low point 2431 may be toward the center of the lateral articulation surface 2421. In 24E, the medial tibial compartment 2413 with medial perimeter 2426 is shown. The medial articulation surface 2420 may meet the medial perimeter 2426 at a medial high point 2427 at or adjacent the medial posterior section 2422. The medial low point 2428 may be closer to the medial anterior section 2423 and toward the medial perimeter 2426. The high points 2427 2430 and low points 2428 2431 on both the medial tibial compartment 2413 and lateral tibial R compartment 2414 are in relation to the insert interface 2411. The difference between the medial high point 2427 and the medial low point 2428 may be greater than the difference between the lateral high point 2430 and the lateral low point 2431 The greater difference in height on the medial articulation side may be represented by the medial ramp 2419.

The medial posterior section 2422 may include the medial ramp 2419, which may begin at the medial high point 2427 and extend away from the medial high point 2427 anteriorly toward the medial low point 2428. Following the surface topography of the medial ramp 2419, the medial articulation surface 2420 tends to have a gradient from the medial high point 2427 toward the medial low point 2428 near the medial anterior section 2423 and to the medial perimeter 2426. The gradient of the lateral articulation surface 2421 flows to the lateral low point 2431. Therefore, movement down gradients on the medial articulation surface 2420 and lateral articulation surface 2421 may be asymmetric. The lateral articulation surface 2421 may be generally concave toward the lateral low point 2431. The location of the medial low point 2428 may cause the directionality of the gradient from the medial ramp 2419 along the medial articulation surface 2420, which causes an object or a mass to move down the gradient in the direction created by the medial ramp 2419. The medial ramp 2419 and the different heights along the medial perimeter 2426 and the medial articulation surface 2420 may create a medial dwell point 2435 that is transient along the gradient. The approximate gradient is represented by dashed lines in FIG. 24F.

The medial posterior side 2415, of the medial tibial compartment 2413, may have a medial thickness defined by the medial high point 2427 at the medial perimeter 2426, which may correspond to the medial ramp 2419, and or the insert interface 2411. The lateral posterior side 2416, of the lateral tibial compartment 2414, may have a lateral thickness defined by the lateral high point 2430 at the lateral perimeter 2429 and the insert interface 2411. Because of the medial ramp 2419, the medial tibial compartment 2413 may have a greater thickness than the lateral tibial compartment 2414.

The medial ramp 2419 and the gradient it creates along the medial articulation surface 2420 towards the medial low point 2428 and may cause a translation or movement of the medial condyle 2402 greater than a translation or movement of the lateral condyle 2403, as the knee and assembly 2400 range from 0 degree of flexion, or extension, to 90 degrees of flexion. The medial condyle 2402 may move down the medial ramp 2419 such that the medial dwell point 2435 migrates anteriorly and outwardly toward the medial perimeter 2426 as the degree of flexion increases. The lateral condyle 2403 may remain in generally the same location near the lateral low point 2431 so the lateral dwell point 2436 may remain in generally the same location. The lateral condyle 2403 may also migrate as the knee moves into flexion, so that the lateral dwell point 2436 migrates posteriorly and outwardly concurrently as the medial dwell point 2435 migrates anteriorly and outwardly. The asymmetric translation of the medial dwell point 2435 and lateral dwell point 2436 may create a tibiofemoral rotation between extension and flexion. As used herein, "tibiofemoral rotation" refers to rotation of a tibia bone and/or part of a patient's leg that includes the tibia bone about a longitudinal axis that is parallel to a center axis of a leg of the patient.

Figure 25D:
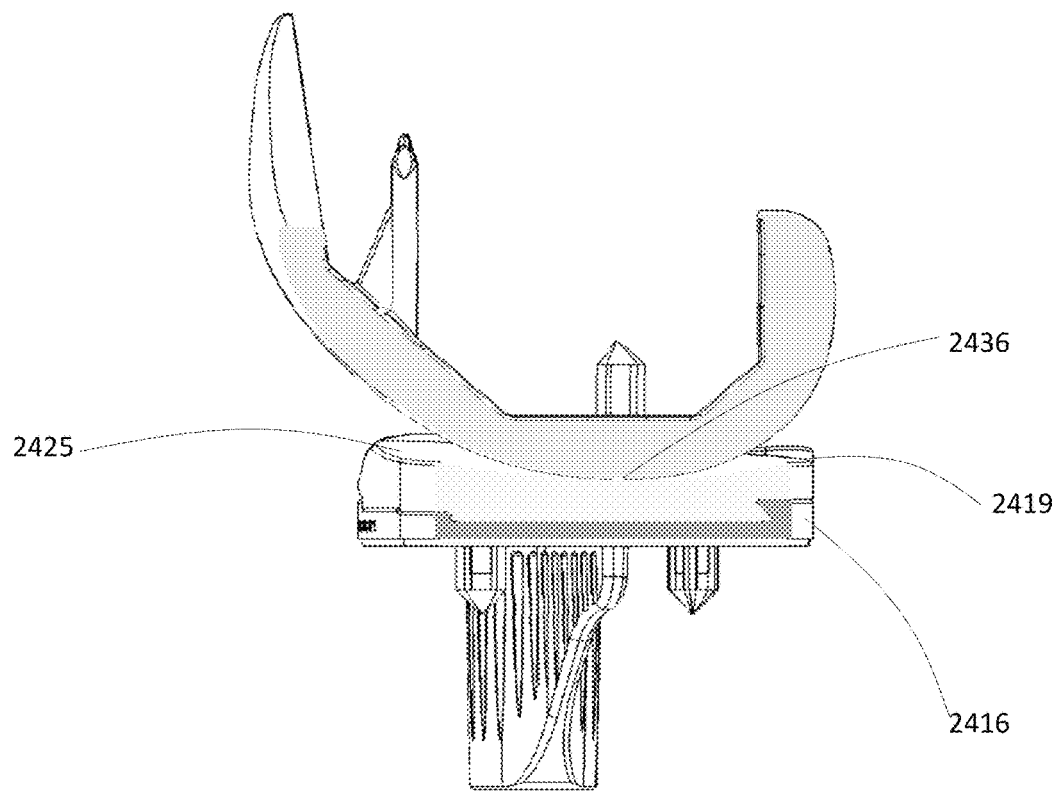
FIG. 25D is a lateral view of the knee prosthesis assembly of FIG. 25A with an anterior-posterior cross-section through the lateral articulation surface.
Figure 25E:
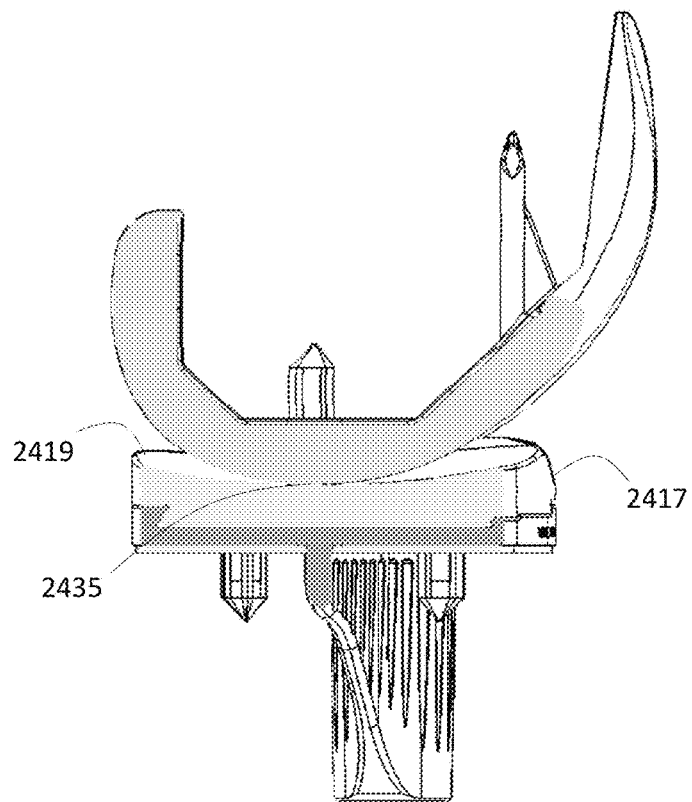
FIG. 25E is a medial view of the knee prosthesis assembly of FIG. 25A an anterior-posterior cross-section through the medial articulation surface.

FIGS. 25-27 demonstrate the movement of the medial dwell point 2435 relative to the lateral dwell point 2436 during flexion of the assembly 2400. FIGS. 25A-25E show a posterior view of the composed assembly 2400 in 0 degree flexion, or "straight leg," in a left knee. FIG. 25A is a medial-lateral cross-section perspective view of the assembly 2400. Generally, the femoral component 2401 contacts the insert 2410 at dwell points. Dwell points are the points of contact between two surfaces. The medial condylar articulation surface 2404 meets the medial articulation surface 2420 at a medial dwell point 2435. The lateral condylar articulation surface 2405 meets the lateral articulation surface 2421 at a lateral dwell point 2436. FIGS. 25B and 25C show the medial dwell point 2435 and the lateral dwell point 2436 at what may be considered a starting position, in 0 degrees flexion. FIG. 25D is an anterior-posterior cross-section through the lateral tibial compartment 2414 of the insert 2410. The medial ramp 2419 is visible (in the background) and shows the height difference between the medial posterior side 2415 and the lateral posterior side 2416. FIG. 25E is an anterior-posterior cross-section through the medial tibial compartment 2413 of the insert 2410; the medial ramp 2419 is visible and is occluding the lower lateral posterior side 2416.

Figure 26A:
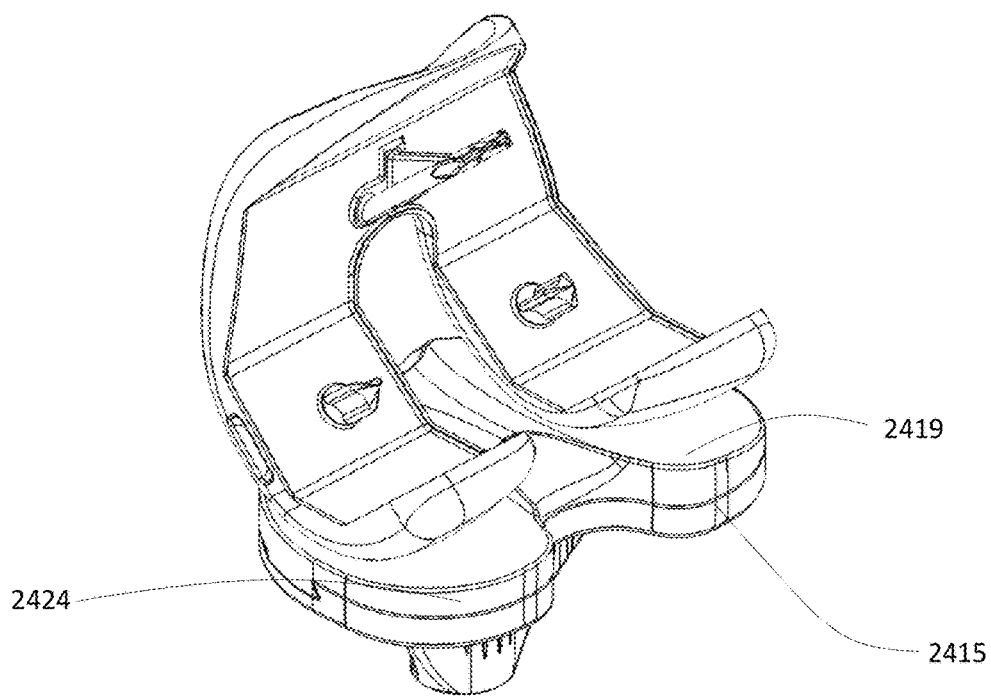
FIG. 26A is perspective posterior view of a knee prosthesis assembly in 45 degree flexion.
Figure 26B:
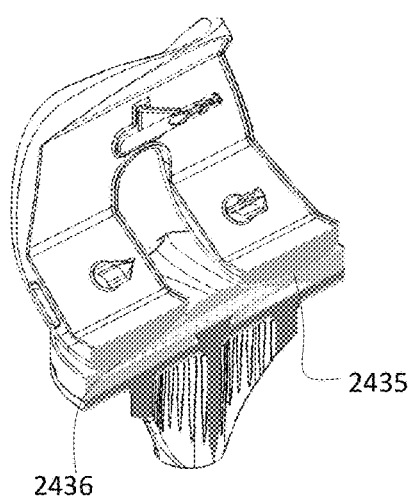
FIG. 26B is a perspective posterior view of the knee prosthesis assembly of FIG. 26A with a medial-lateral cross-section.
Figure 26C:
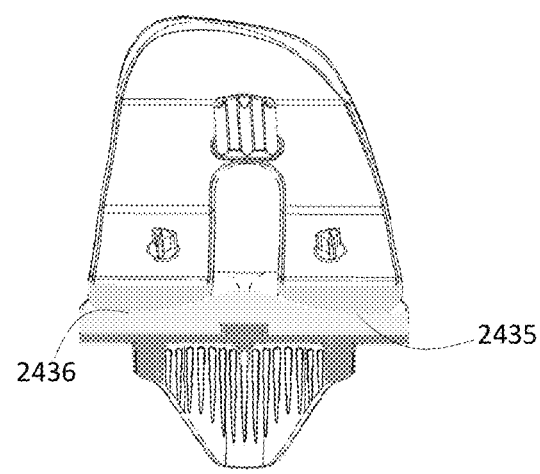
FIG. 26C is a posterior view of the knee prosthesis assembly of FIG. 26B.
Figure 26D:
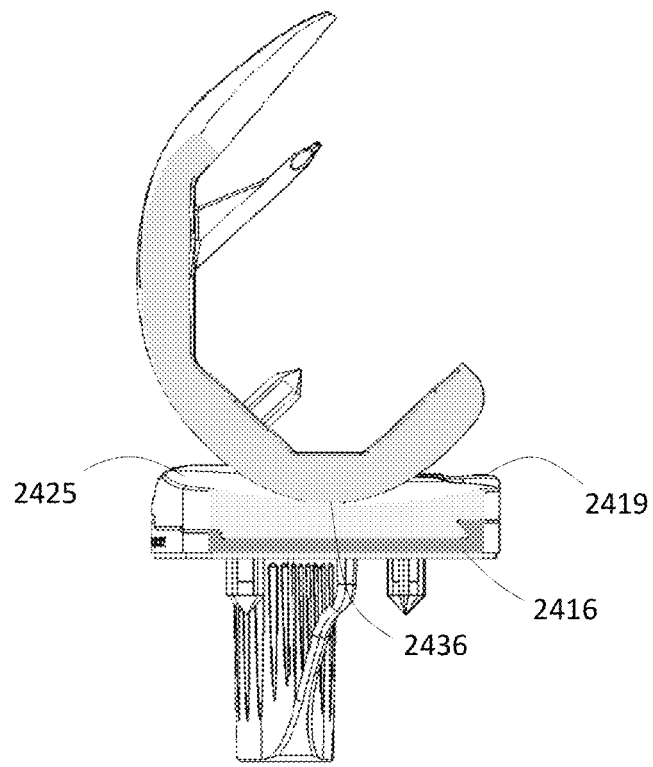
FIG. 26D is a lateral view of the knee prosthesis assembly of FIG. 26A with an anterior-posterior cross-section through the lateral articulation surface.
Figure 26E:
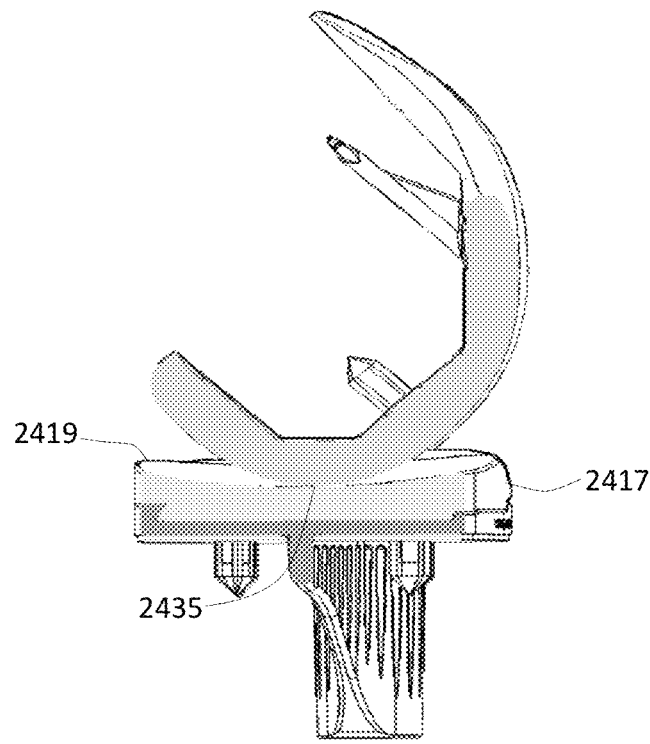
FIG. 26E is a medial view of the knee prosthesis assembly of FIG. 26A an anterior-posterior cross-section through the medial articulation surface.

FIGS. 26A-26E show a posterior view of the composed assembly 2400 in 45 degree flexion, in a left knee. FIG. 26A is a medial-lateral cross-section perspective view of the assembly 2400. The medial condylar articulation surface 2404 meets the medial articulation surface 2420 at a medial dwell point 2435. The lateral condylar articulation surface 2405 meets the lateral articulation surface 2421 at a lateral dwell point 2436. FIGS. 26B and 26C show the medial dwell point 2435 and the lateral dwell point 2436 at what may be considered a starting position, in 45 degrees flexion. FIG. 26D is an anterior-posterior cross-section through the lateral tibial compartment 2414 of the insert 2410. The medial ramp 2419 is visible (in the background) and shows the height difference between the medial posterior side 2415 and the lateral posterior side 2416. FIG. 26E is an anterior-posterior cross-section through the medial tibial compartment 2413 of the insert 2410; the medial ramp 2419 is visible and is occluding the lower lateral posterior side 2416. Relative to 0 degrees flexion, the medial dwell point 2435 has moved slightly and the lateral dwell point 2436 has not moved significantly.

Figure 27D:
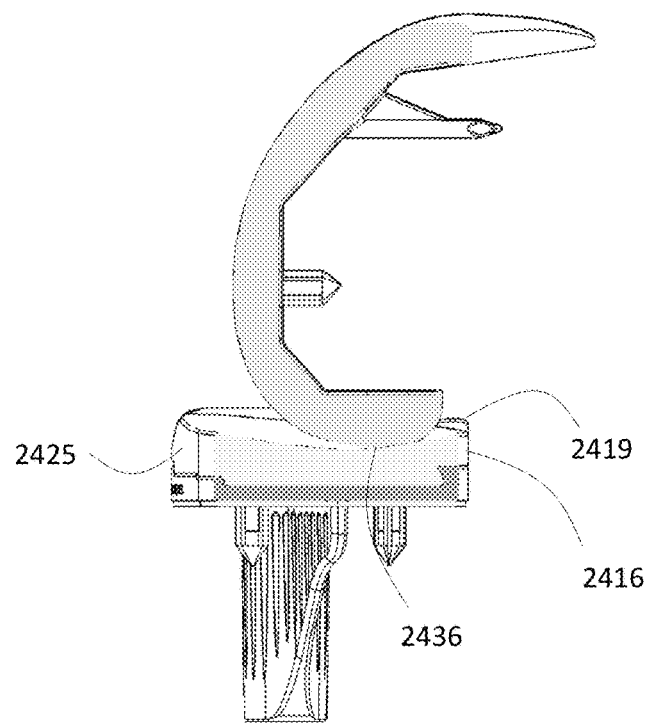
FIG. 27D is a lateral view of the knee prosthesis assembly of FIG. 27A with an anterior-posterior cross-section through the lateral articulation surface.
Figure 27E:
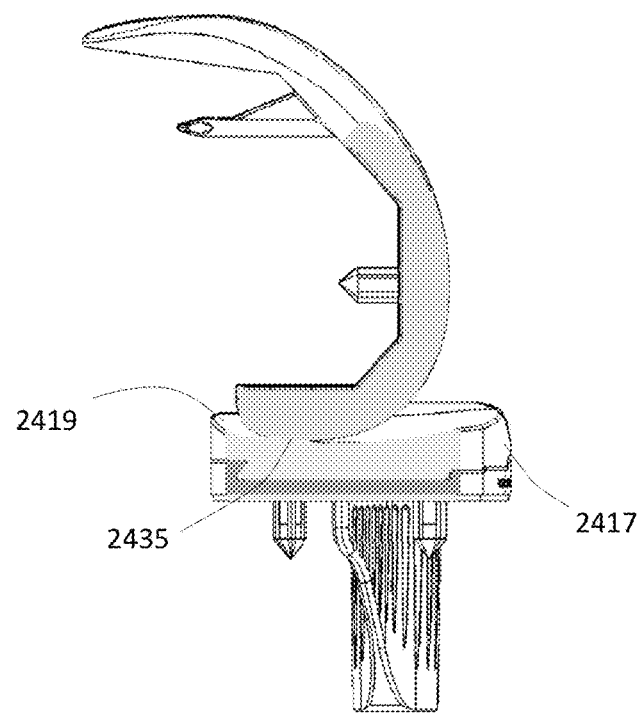
FIG. 27E is a medial view of the knee prosthesis assembly of FIG. 27A an anterior-posterior cross-section through the medial articulation surface.

FIGS. 27A-27E show a posterior view of the composed assembly 2400 in 90 degree flexion, in a left knee. FIG. 27A is a medial-lateral cross-section perspective view of the assembly 2400. The medial condylar articulation surface 2404 meets the medial articulation surface 2420 at a medial dwell point 2435. The lateral condylar articulation surface 2405 meets the lateral articulation surface 2421 at a lateral dwell point 2436. FIGS. 27B and 27C show the medial dwell point 2435 and the lateral dwell point 2436 at what may be considered a starting position, in 90 degrees flexion. FIG. 27D is an anterior-posterior cross-section through the lateral tibial compartment 2414 of the insert 2410. The medial ramp 2419 is visible (in the background) and shows the height difference between the medial posterior side 2415 and the lateral posterior side 2416. FIG. 27E is an anterior-posterior cross-section through the medial tibial compartment 2413 of the insert 2410; the medial ramp 2419 is visible and is occluding the lower lateral posterior side 2416. Relative to 0 degrees flexion, the medial dwell point 2435 has moved substantially anteriorly and outwardly toward the medial perimeter 2426 and the lateral dwell point 2436 has not moved significantly. During the transition from extension to flexion, the medial dwell point 2435 has moved anteriorly from the medial ramp 2419 toward the medial low point 2428. The lateral dwell point 2436 has not substantially moved along the lateral articulation surface 2421.

The asymmetry of the insert 2410, and particularly the medial ramp 2419, may cause greater translation of the medial dwell point 2435 compared to the lateral dwell point 2436. The medial dwell point 2436 translation, alone or in conjunction with lateral dwell point 2435 translation, causes or allows tibiofemoral rotation similar to that of a natural knee. Tibiofemoral rotation in a natural knee is the outward rotation of the tibia and lower leg relative to the femur in flexion. In natural tibiofemoral rotation, the toes point outward in flexion compared to extension. The degree of medial dwell point 2435 translation may correspond to rotation of the tibial baseplate component 2440 and insert 2410 relative to the femoral component 2401.

The resultant tibiofemoral rotation as a result of the asymmetry of the insert 2410 may provide additional joint stability in the patient. As the medial dwell point 1540 migrates medially, toward the sagittal plane, the medial collateral ligaments of the knee may maintain tension as the knee moves from extension to flexion. The tibiofemoral rotation and maintenance of tension of the medial ligaments may more accurately mimic the movement of a healthy knee. Assembly 2400 may allow a more natural biomechanical range of motion of the knee compared to knee prosthetics with symmetric medial and lateral articulation sides.

Referring to FIG. 24A, the exploded assembly 2400 is shown from a lateral side configured for placement in a left knee and shown in approximately 90 degree extension, or "flexion." The tibial articulation surface 2412 may include a medial tibial compartment 2413 (indicated generally by the letter "M") and a lateral tibial compartment 2414 (indicated generally by the letter "L"). In particular, the tibial insert 2410 may be configured and designed specifically for use with a left knee of a patient and may be configured to fit within a tibial baseplate component 2440. Furthermore, the tibial articulation surface 2412 may be configured to contact and interface with a femoral component 2401, which may be specifically configured for a left knee.

Figure 28A:
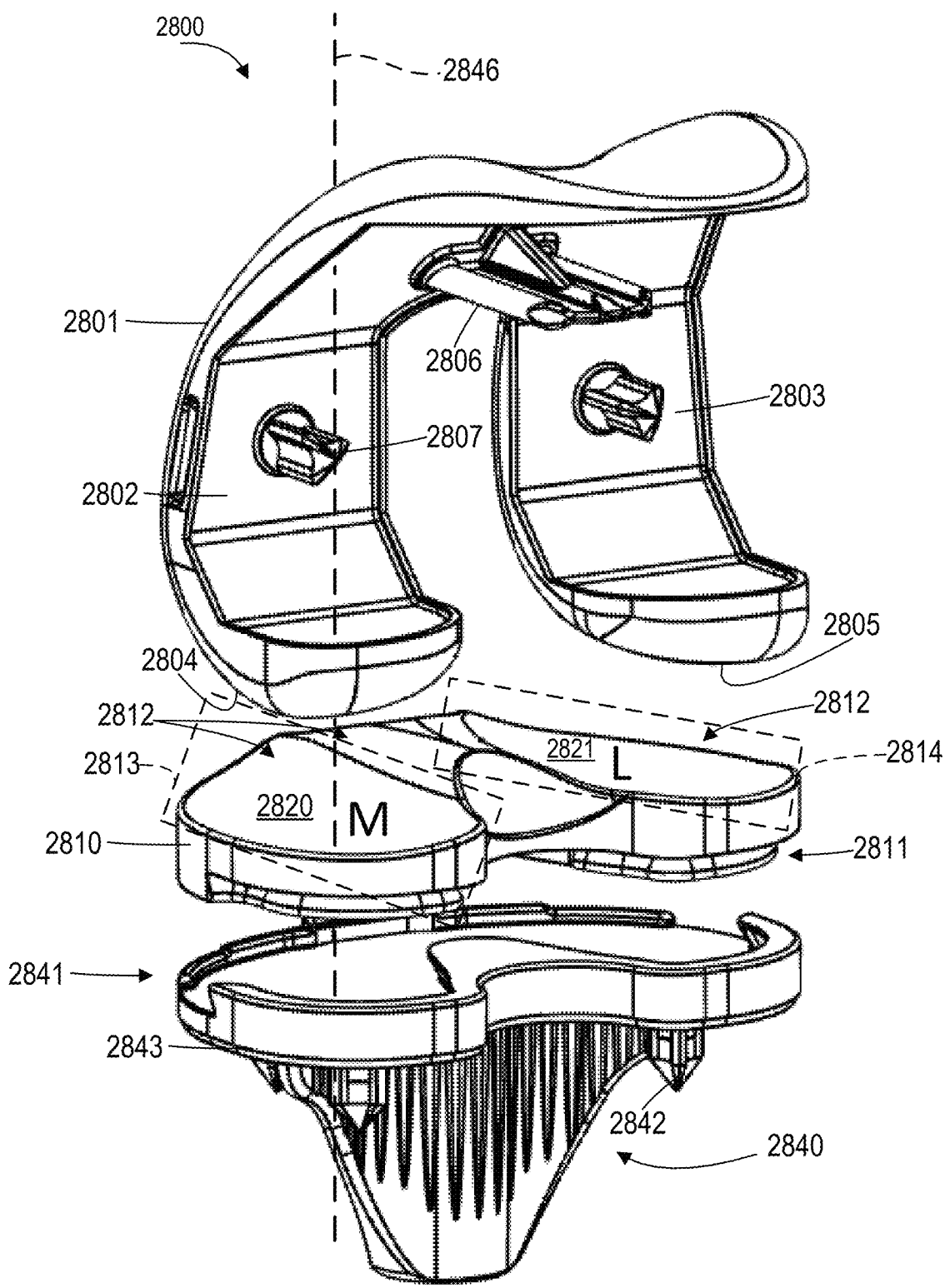
FIG. 28A is a posterior exploded view of a knee prosthesis assembly with an asymmetric tibial insert.

Referring to FIGS. 28A to 28F, an assembly 2800 for an implantable knee prosthesis is shown, according to another embodiment. Assembly 2800 may include a femoral component 2801, an insert 2810, and a tibial baseplate component 2840. FIG. 28A is an exploded view of the assembly 2800 viewed from a posterior-lateral side, in reference to the anatomy of a patient. The assembly 2800 is generally asymmetric across the medial and lateral sides, in other words the left side is asymmetric compared to the right side. FIGS. 28A-28F illustrate a right knee design.

The femoral component 2801 may be posterior stabilizing or cruciate retaining. In FIG. 28A, the femoral component 2801, the tibial insert 2810, and the tibial baseplate component 2840 are shown in flexion. The femoral component 2801 may include medial condyle 2802 and lateral condyle 2803, similar to femoral component 114 in FIG. 9. The medial 2802 and lateral 2803 condyles may include medial condylar articulation surface 2804 and lateral condylar articulation surface 2805. The femoral component 2801 may include elements to secure the femoral component 2801 to a femur of a patient. For example, the femoral component 2801 may include at least one keel 2806 and at least one post 2807 that penetrate the bone of the associated femur (not shown) to secure the femoral component 2801 to the femur. The at least one post 2807 may be placed on the femoral side of the medial condyle 2802 and/or the lateral condyle 2803. The femoral component 2801 may include surface texturing on a bone-facing side to encourage bone in-growth and securement.

The tibial baseplate component 2840 may be configured to be secured to the tibia of the patient. The tibial baseplate component 2840 may include an insert interface 2841 configured for the placement and securement of the insert 2810, with one or more tibial posts 2842, which may be inserted and secured into a patient's tibia. The tibial baseplate component 2840 may further have a base 2843, which, in certain embodiments, may also be designed to penetrate the tibial plateau, and may receive a separate keel (not shown) that penetrates more deeply into an intramedullary canal of the tibia.

FIG. 28A shows the exploded assembly 2800 from a lateral side configured for placement in a left knee and shown in approximately 90 degree extension, or "flexion." While the tibial baseplate component 2840 and the femoral component 2801 may be medially and laterally symmetric across an anterior-posterior plane, the insert 2810 may be medially-laterally asymmetric. The insert 2810 may include a baseplate interface 2811 configured to mate or engage with the insert interface 2841 of the tibial baseplate component 2840. The baseplate interface 2811 may have features complementary to features on the insert interface 2841. The complementary features may allow for a removable fit for the tibial insert 2810. The removable fit may allow for a modular assembly 2800, benefitting the surgeon and the patient.

As used herein, an "interface" refers to an area, a boundary, or a place at which two R separate and/or independent structures, members, apparatus, assemblies, components, and/or systems join, connect, are coupled, or meet and act on, or communicate, mechanically or electronically, with each other. In certain embodiments, "interface" may refer to a surface forming a common boundary of two bodies, spaces, structures, members, apparatus, assemblies, components, or phases. (search "interface" on Merriam-Webster.com. Merriam-Webster, 2021. Web. 15 Nov. 2021. Modified.) In certain embodiments, the term interface may be used with an adjective that identifies a type or function for the interface. For example, an engagement interface may refer to one or more structures that interact or connect to mechanically join or connect two separate structures, each connected to a side of the interface.

In some embodiments, the tibial baseplate component 2840 and the femoral component 2801 may be symmetric, as mentioned previously, enabling them to be used for either left or right knee replacements. In certain embodiments, the tibial insert 2810 may be specific to one side of a patient or the other. An assembly for either left or right knee arthroplasty may include a single femoral component 2801, a single tibial baseplate component 2840, and two (e.g., left and right) inserts 2410, 2810. This may greatly reduce the inventory requirements for the system.

Opposite the baseplate interface 2811, the tibial insert 2810 includes a tibial articulation surface 2812 configured for engagement with the medial condyle 2802 and lateral condyle 2803 on the femoral component 2801. The tibial articulation surface 2812 may be a superior side of the tibial insert 2810. The tibial articulation surface 2812 may include a medial tibial compartment 2813 and a lateral tibial compartment 2814. In certain embodiments, the medial tibial compartment 2813 and/or the lateral tibial compartment 2814 may be respectively defined by a medial perimeter and a lateral perimeter, discussed more below.

The medial tibial compartment 2813 may include a medial articulation surface 2820 for direct engagement with the medial condylar articulation surface 2804. The lateral tibial compartment 2814 may include a lateral articulation surface 2821 for direct engagement with the lateral condylar articulation surface 2805. The medial condylar articulation surface 2804 may engage with the medial articulation surface 2820 at a medial dwell point 2835 (shown in subsequent figures). The lateral condylar articulation surface 2805 may engage with the lateral articulation surface 2821 at a lateral dwell point 2836 (shown in subsequent figures). In certain embodiments, the medial articulation surface 2820 may include a medial ramp 2838, which, in certain embodiments, may have no counterpart on the lateral articulation surface 2821 and may create at least part of the asymmetry between the medial tibial compartment 2813 and the lateral tibial compartment 2814.

In certain embodiments, the assembly 2800 may include a longitudinal axis 2846. The longitudinal axis 2846 may generally indicate an area or vicinity where a condyle articulation surface rotates during tibiofemoral rotation that occurs during arthrosis (joint) flexion. The present disclosure supports one or more embodiments of a knee assembly, for example assembly 2800, that enables, facilitates, and/or provides for tibiofemoral rotation about a longitudinal axis within a medial tibial compartment 2813 (as shown by longitudinal axis 2846 in FIG. 28A). Alternatively, or in addition, tibiofemoral rotation may be about a longitudinal axis within a lateral tibial compartment 2814. In certain embodiments, the shape and/or contour of a lateral articulation surface and/or a medial articulation surface can influence whether the longitudinal axis is within the lateral tibial compartment (generally defined by the lateral articulation surface) or the medial tibial compartment (generally defined by the medial articulation surface).

The present disclosure includes embodiments for which the tibial articulation surface 2812 is contoured to position a longitudinal axis of tibiofemoral rotation within a desired or engineered compartment of the tibial articulation surface 2812. Generally, the more constraint a tibial articulation surface 2412,2812 imparts on a condyle of the femoral component, the more rotation about an axis within that area of the tibial articulation surface 2412,2812. For example, to position the longitudinal axis 2446 within the medial articulation surface 2420 of the tibial articulation surface 2412, the medial articulation surface 2420 is contoured to impose more constraint on the medial condylar articulation surface 2404 of the medial condyle 2402 than the lateral articulation surface 2421. Similarly, to position the longitudinal axis 2846 within the lateral articulation surface 2821 of the tibial articulation surface 2812, the lateral articulation surface 2821 is contoured to impose more constraint on the lateral condylar articulation surface 2805 of the lateral condyle 2803 than the medial articulation surface 2820.

As used herein, "constraint" refers to refers to an apparatus, instrument, structure, device, component, system, or assembly that is structured, organized, configured, designed, arranged, or engineered to prevent, limit, impede, stop, or restrict motion or movement and/or operation of the another object, member, structure, component, part, apparatus, system, or assembly. (Search "constraint" on wordhippo.com. WordHippo, 2021. Web. Accessed 8 Dec. 2021. Modified.) In certain embodiments, "constraint" may refer to a state of an object being constrained, temporarily, permanently, before, after, and/or during motion.

In FIG. 28A, the lateral tibial compartment 2814 and/or medial tibial compartment 2813 are configured such that the longitudinal axis 2846 for tibiofemoral rotation is within the medial tibial compartment 2813. In FIG. 24A, the lateral tibial compartment 2814 and/or medial tibial compartment 2813 are configured such that the longitudinal axis 2446 is within a medial tibial compartment, which may be generally defined by the medial articulation surface 2420. Knee assemblies that are configured, designed, and/or engineered for tibiofemoral rotation is within the lateral tibial compartment 2814 may be referred to as lateral pivot design knee assemblies. Knee assemblies that are configured, designed, and/or engineered for tibiofemoral rotation is within the medial tibial compartment may be referred to as medial pivot design knee assemblies. With certain patients it may be desirable to use a lateral pivot design knee assembly in a left knee and a medial pivot design knee assembly in a right knee. Alternatively, or in addition, it may be desirable to use a medial pivot design knee assembly in a left knee and a lateral pivot design knee assembly in a right knee. Alternatively, or in addition, it may be desirable to use a lateral pivot design knee assembly or a medial pivot design knee assembly in either or both of a left knee and a right knee.

Figure 28B:
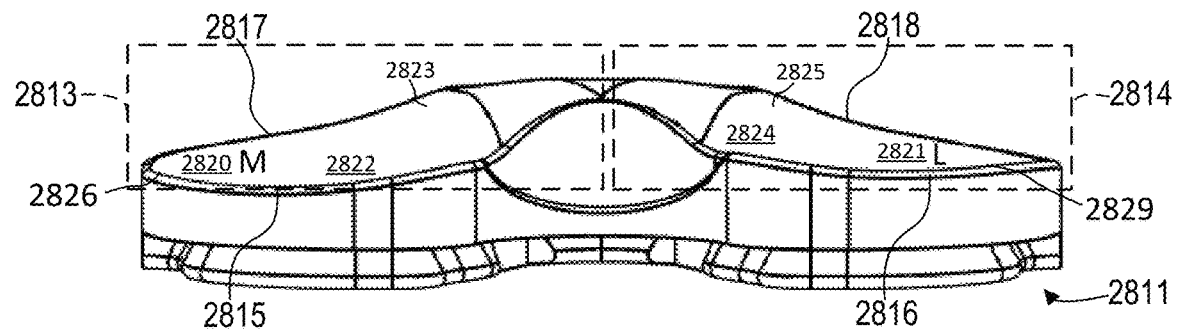
FIG. 28B is a posterior view of the asymmetric tibial insert of FIG. 28A.
Figure 28C:
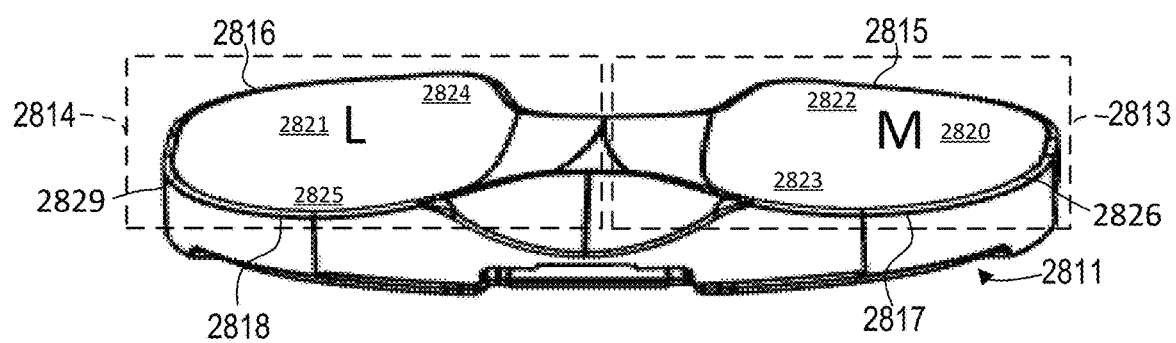
FIG. 28C is an anterior view of the asymmetric tibial insert of FIG. 28A.
Figure 28D:
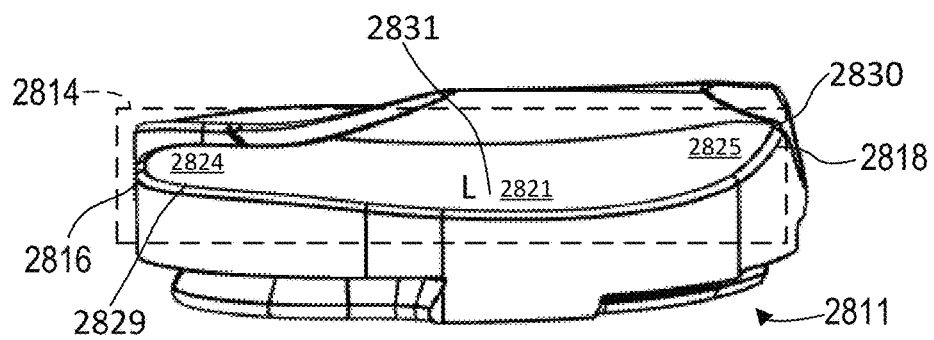
FIG. 28D is a lateral view of the asymmetric tibial insert of FIG. 28A.

FIGS. 28B-28D show details of the shape and/or contours of the tibial insert 2810. FIG. 24B is a posterior view of the tibial insert 2810. FIG. 28C is an anterior view of the tibial insert 2810. The medial tibial compartment 2813 may include a medial posterior side 2815 and a medial anterior side 2817. The medial articulation surface 2820 may include a medial posterior section 2822 and a medial anterior section 2823 surrounded by a medial perimeter 2826. As used herein, "medial perimeter" refers to a perimeter that is near or about a medial compartment. The lateral tibial compartment 2814 may include a lateral posterior side 2816 and a lateral anterior side 2818. The lateral articulation surface 2821 may include a lateral posterior section 2824 and a lateral anterior section 2825 surrounded by a lateral perimeter 2829. As used herein, "lateral perimeter" refers to a perimeter that is near or about a lateral compartment.

Figure 28E:
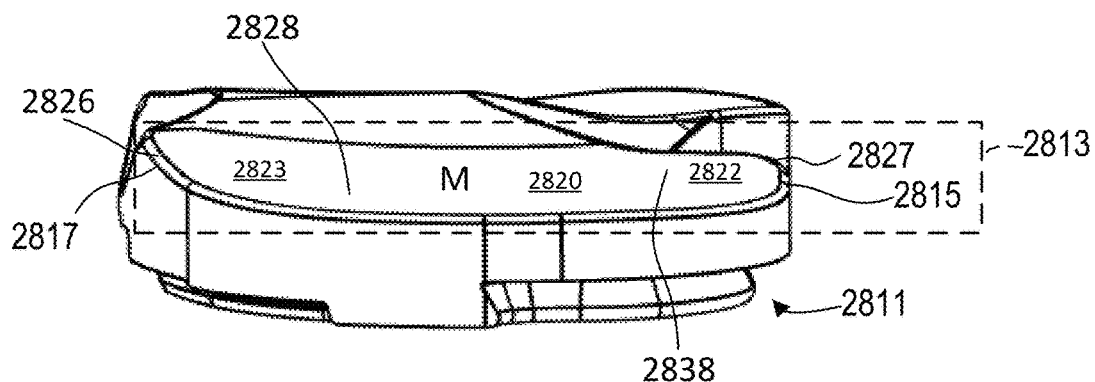
FIG. 28E is a medial view of the asymmetric tibial insert of FIG. 28A.

FIGS. 28D and 28E show lateral and medial views of the tibial insert 2810, respectively. In 24D, the lateral articulation surface 2821 with lateral perimeter 2829 is shown. The lateral articulation surface 2821 may meet the lateral perimeter 2829 at a lateral high point 2830. As used herein, "lateral high point" refers to a point or an area of a lateral compartment that is higher within the lateral compartment than other points or areas within the lateral compartment. The lateral low point 2831 may include a lateral low point 2831 that may be toward the center of the lateral articulation surface 2821. As used herein, "lateral low point" refers to a point or an area of a lateral compartment that is lower within the lateral compartment than other points or areas within the lateral compartment.

In 28E, the medial articulation surface 2820 with medial perimeter 2826 is shown. The medial articulation surface 2820 may meet the medial perimeter 2826 at a medial high point 2827 at, near, or adjacent to the medial posterior section 2822. As used herein, "medial high point" refers to a point or an area of a medial compartment that is higher within the medial compartment than other points or areas within the medial compartment. The medial articulation surface 2820 may include a medial low point 2828 closer to the medial anterior section 2823 and toward the medial perimeter 2826. As used herein, "medial low point" refers to a point or an area of a medial compartment that is lower within the medial compartment than other points or areas within the medial compartment.

The high points 2827,2830 and low points 2828,2831 on both the lateral articulation surface 2821 and medial articulation surface 2820 are in relation to the baseplate interface 2811. The difference between the medial high point 2827 and the medial low point 2828 may be greater than the difference between the lateral high point 2830 and the lateral low point 2831 The greater difference in height on the medial articulation surface 2820 may be represented by the medial ramp 2838 (See representation in FIG. 28F).

The medial posterior section 2822 may include the medial ramp 2838, which may begin at the medial high point 2827 and extend away from the medial high point 2827 anteriorly toward the medial low point 2828. Following the surface topography of the medial ramp 2838, the medial articulation surface 2820 tends to have a gradient from the medial high point 2827 toward the medial low point 2828 near the medial anterior section 2823 and to the medial perimeter 2826. The gradient of the lateral articulation surface 2821 flows to the lateral low point 2831. Therefore, movement down gradients on the medial articulation surface 2820 and lateral articulation surface 2821 may be asymmetric. The lateral articulation surface 2821 may be generally concave toward the lateral low point 2831. The location of the medial low point 2828 may cause the directionality of the gradient from the medial ramp 2838 along the medial articulation surface 2820, which causes an object or a mass to move down the gradient in the direction created by the medial ramp 2838. The medial ramp 2838 and the different heights along the medial perimeter 2826 and the medial articulation surface 2820 may create a medial dwell point 2835 that is transient along the gradient. The approximate gradients within medial tibial compartment 2813 and/or lateral tibial compartment 2814 are represented by dashed lines in FIG. 28F.

The medial posterior side 2815, of the medial tibial compartment 2813, may have a thickness defined by the medial high point 2827 at the medial perimeter 2826, which may correspond to the medial ramp 2838, and/or the baseplate interface 2811. The lateral posterior side 2816, of the lateral tibial compartment 2814, may have a thickness defined by the lateral high point 2830 at the lateral perimeter 2829 and the baseplate interface 2811. Because of the medial ramp 2838, the medial tibial compartment 2813 may have a greater thickness than the lateral tibial compartment 2814.

Figure 28F:
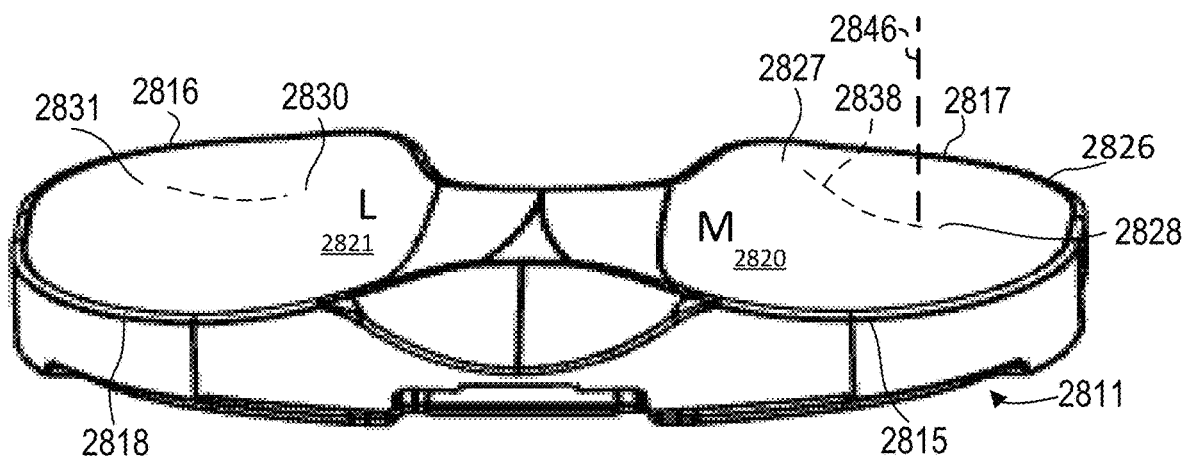
FIG. 28F is an anterior perspective view of the asymmetric tibial insert of FIG. 28A.

Referring to FIG. 28F, the medial ramp 2838 and the gradient it creates along the medial articulation surface 2820 towards the medial low point 2828 and may cause a translation or movement of the medial condyle 2802 greater than a translation or movement of the lateral condyle 2803, as the knee and assembly 2800 range from 0 degrees of flexion, or extension, to 90 degrees of flexion. The medial condyle 2802 may move down the medial ramp 2838 such that the medial dwell point 2835 migrates anteriorly and outwardly toward the medial perimeter 2826 as the degree of flexion increases. The lateral condyle 2803 may remain in generally the same location near the lateral low point 2831 so the lateral dwell point 2836 may remain in generally the same location. In certain embodiments, the lateral condyle 2803 may also migrate as the knee moves into flexion, so that the lateral dwell point 2836 migrates posteriorly and outwardly concurrently as the medial dwell point 2835 migrates anteriorly and outwardly. The asymmetric translation of the medial dwell point 2835 and lateral dwell point 2836 may create a tibiofemoral rotation between extension and flexion. Such tibiofemoral rotation is desired behavior for a healthy knee joint and may be referred to as Screw home Mechanism (SHM) of a knee joint caused, at least in part, by the difference in size of the medial condyle and lateral condyle of the distal femur.

Figure 29:
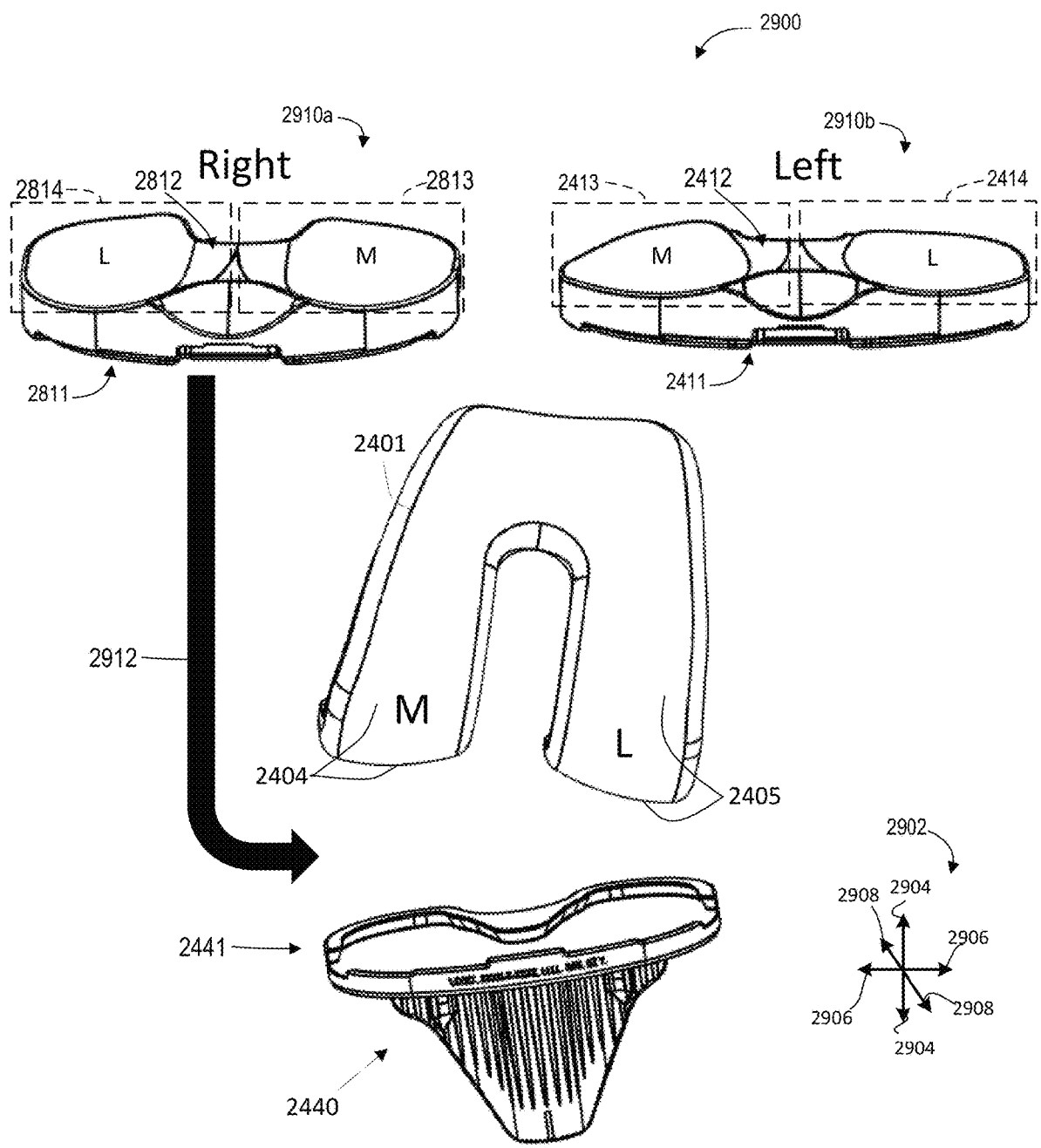
FIG. 29 is a perspective anterior view of knee prosthesis system according to one embodiment of the present disclosure.

FIG. 29 is a perspective anterior view of a knee prosthesis system 2900 according to one embodiment of the present disclosure. The knee prosthesis system 2900 includes a femoral component, an insert, and a tibial baseplate component. In certain embodiments, a particular femoral component and a particular tibial baseplate component are specifically configured for a left knee joint. In certain embodiments, a particular femoral component and a particular tibial baseplate component are specifically configured for a right knee joint. Alternatively, or in addition, the femoral component and tibial baseplate component may be specifically configured for use in either one of a left knee joint or a right knee joint. A knee prosthesis system 2900 for the left knee joint may be configured for a first side of a patient. Alternatively, or in addition, a knee prosthesis system for the right knee joint may be configured for a second side of a patient, the second side being the other side of the right side and the left side.

In the illustrated embodiment, the femoral component is the femoral component 2401 for a left knee (See FIG. 24A) and the tibial baseplate component is the tibial baseplate component 2440 for a left knee. The tibial baseplate component 2440 includes an insert interface 2441. The femoral component 2401 includes a femoral articulation surface that includes one, or both of, the medial condylar articulation surface 2404 and the lateral condylar articulation surface 2405.

FIG. 29 illustrates a three-dimensional axis 2902. The three-dimensional axis 2902 includes a cephalad-caudal axis 2904, a medial-lateral axis 2906, and an anterior-posterior axis 2908. FIG. 29 illustrates the orientation and configuration of the femoral component 2401 and tibial baseplate component 2440 for a left knee of a patient where the left knee has a condition. As used herein, a "condition" refers to a state of something with regard to its appearance, quality, or working order. In certain embodiments, a condition may refer to a patient's state of health or physical fitness or the state of health or physical fitness of an organ or anatomical part of a patient. In certain embodiments, a condition may refer to an illness or deformity of a patient or of an organ or anatomical part of a patient. (Search "condition" on wordhippo.com. WordHippo, 2021. Web. Accessed 8 Dec. 2021. Modified.) In the illustrated embodiment, the left knee of a patient has a varus condition with the knee joint angled about eight degrees away from a vertical axis, such as the cephalad-caudal axis 2904.

As used herein, a "varus condition" refers to a state of a bone or joint having an undesired inward angulation (medial angulation, that is, towards the body's midline) of the distal segment of a bone or joint. The opposite of varus is called valgus. The terms varus and valgus refer to the direction that the distal segment of the joint points. For example, a varus condition at the knee results in a bowlegged appearance with the distal part of the leg deviated inward, in relation to the femur. In a valgus condition of the knee, the distal part of the leg below the knee is deviated outward, in relation to the femur, resulting in a knock-kneed appearance. (Search "varus deformity" on Wikipedia.com Oct. 20, 2020. Modified. Accessed Jan. 6, 2020.) A varus condition can be experienced in a variety of joints, including but not limited to, ankle joints, elbow joints, foot joints, hand joints, hip joints, knee joints, toe joints, wrist joints, and the like. A knee that has a varus condition may also be referred to as a varus knee.

A patient knee with a varus condition may cause one or more problems or challenges in the kinematics of the knee as the knee transitions through various angles of flexion and/or extension. For example, a varus knee may have undesirable stability (insufficient stability) during flexion. This undesired instability may be caused by a gap imbalance between the medial and lateral condyles of the femoral component 2401 (or the distal end of the femur). Such instability is referred to as mediolateral stability.

As used herein, "mediolateral stability" refers to a condition of joint and/or parts associated with a joint being stable or in equilibrium, and thus resistant to change along a medial-lateral axis 2906 of a patient and/or a joint of the patient. (Search "stability" on wordhippo.com. WordHippo, 2021. Web. Accessed 8 Dec. 2021. Modified.) The insufficient or undesirable level of mediolateral stability during flexion may cause anxiety for the patient during flexion and reduced confidence in the integrity and performance of the knee prosthesis system 2900.

Advantageously, the knee prosthesis system 2900 can remediate an undesirable level of mediolateral stability based on a tibial insert used by the surgeon when deploying the knee prosthesis system 2900. In the illustrated embodiment, the surgeon may choose, either pre-operatively and/or intraoperatively, to use tibial insert 2910a with the tibial baseplate component 2440 and the femoral component 2401 for a left knee. The tibial insert 2910a is positioned between the tibial baseplate component 2440 and the femoral component 2401 when deployed, see arrow 2912.

The tibial insert 2910a includes a tibial articulation surface 2812 having a medial tibial compartment 2813 and a lateral tibial compartment 2814. The tibial insert 2910b includes a tibial articulation surface 2412 having medial tibial compartment 2413 and a lateral tibial compartment 2414. Advantageously, in one embodiment, the baseplate interface 2811 of the tibial insert 2910a is complementary to, and/or compatible with, the insert interface 2441 of the tibial baseplate component 2440. The baseplate interface 2411 of the tibial insert 2910b is also complementary to, and/or compatible with, the insert interface 2441 of the tibial baseplate component 2440. The compatible interfaces 2811, 2441 enable the surgeon to deploy the tibial insert 2910a with the tibial baseplate component 2440 and the femoral component 2401 for a left knee to adapt, adjust, refine, or modify kinematics of a patient's left knee joint having a condition. The tibial articulation surface 2812 is shaped to cooperate with the femoral articulation surface to adapt kinematics of a knee joint having a condition. In the illustrated embodiment, the condition is a varus condition, the condition can also be one of a valgus condition and a balanced condition.

In one embodiment, the tibial articulation surface 2812 is configured to include one or more of a medial tibial compartment 2813, a lateral tibial compartment 2814, a medial articulation surface 2820, a lateral articulation surface 2821, and/or high and/or low points within the medial articulation surface 2820, and/or the lateral articulation surface 2821 to R remediate a condition of the knee joint into which the knee prosthesis system 2900 deployed. In one embodiment, the tibial articulation surface 2812 contour and/or features adjust mediolateral stability during flexion of a first knee joint having a varus condition: is a varus knee joint. In one embodiment, a tibial articulation surface 2812 of the tibial insert 2910a may adjust mediolateral stability by increasing constraint on a lateral collateral ligament of the first knee joint and decreases tension on a medial collateral ligament of the first knee joint.

It should be noted that in the illustrated embodiment a surgeon may deploy the tibial insert 2910a in a left knee because the knee has a condition. However, the tibial insert 2910a may also be deployed (e.g., is suitable for implantation) in a patient's right knee joint that lacks the condition. As used herein, "suitable for implantation" refers to device or implant configured such that deployment of the implant in a patient will result in a desired impact on the health and/or wellbeing of the patient. While the tibial insert 2910a may be designed for deployment in a right knee joint that lacks a condition, or has a balanced condition, the tibial insert 2910a is illustrated in FIG. 29 being deployed in a left knee joint that has a varus condition of about eight degrees.

As used herein, "kinematics" refers to an area of mechanics concerned with objects in motion, but not with the forces involved. (Search "compartment" on wordhippo.com. WordHippo, 2021. Web. Accessed 8 Dec. 2021. Modified.) In certain embodiments, kinematics refers to aspects involved in the motion and/or interaction of components in motion in relation to each other and other components. Motions involved in kinematics may include but are not limited to linear, rotary, reciprocating, and/or oscillating.

As used herein, "flexion" refers to the act of bending a joint, especially a bone joint. The counteraction of extension. (Search "flexion" on wordhippo.com. WordHippo, 2021. Web. Accessed 8 Dec. 2021. Modified.) Flexion may include the act of moving parts of a joint from an unflexed or extended state to a nonextended or flexed state and may be expressed in terms of degrees of the flexion and/or extension. The range of degrees available to express the state of extension and/or flexion may depend on the range of motion for a particular joint. As used herein, "extension" refers to the act of unbending a joint, especially a bone joint. The counteraction of flexion. (Search "flexion" on wordhippo.com. WordHippo, 2021. Web. Accessed 8 Dec. 2021. Modified.) Extension may include the act of moving parts of a joint from a flexed state to an extended state and may be expressed in terms of degrees of the extension and/or flexion. The range of degrees available to express the state of extension and/or flexion may depend on the range of motion for a particular joint. As used herein, a "tension" refers to a force that is applied to both ends of a thin elongated structure. For example, a ligament such as a lateral collateral ligament may experience tension due to how the ligament is attached to a femur bone and tibia bone and stretched during flexing of the knee joint.

In one embodiment, the femoral component 2401 is configured for a first side of a patient and the tibial insert 2910*a* is configured for the second side of the patient. In the illustrated embodiment, the first side may be a left side of a patient and the second side may be a right side of a patient. Alternatively, or in addition, the first side may be a right side of a patient and the second side may be a left side of a patient.

Referring still to FIG. 29, with a knee joint having a varus condition, a surgeon may decide to couple, or connect, the tibial insert 2910*a* to the tibial baseplate component 2440. As the surgical procedure is completed, a patient's knee joint, such as a left knee joint, includes the femoral component 2401 having a medial femoral compartment that includes the medial condylar articulation surface 2404 and a lateral femoral compartment that includes the lateral condylar articulation surface 2405. In the illustrated embodiment, the medial condylar articulation surface 2404 defines the medial femoral compartment and the lateral condylar articulation surface 2405 defines the lateral femoral compartment. The tibial insert 2910*a* may be used instead of the tibial insert 2910*b* because the left knee presents a varus condition.

With the tibial insert 2910*a* deployed in the knee joint, the medial tibial compartment 2813 engages the lateral femoral compartment at a lateral dwell point (shown in later figures) during flexion and the lateral tibial compartment 2814 engages the medial femoral compartment at a medial dwell point (shown in later figures) during flexion. Those of skill in the art will recognize that this is different from the arrangement should the tibial insert 2910*b* be deployed between the femoral component 2401 and the tibial baseplate component 2440. Said another way, if the left tibial insert 2910*b* were deployed in a left knee joint, the medial compartments of each of the femoral component 2401 and the tibial baseplate component 2440 would engage with each other and the lateral compartments of each of the femoral component 2401 and the tibial baseplate component 2440 would engage with each other.

Figure 30:
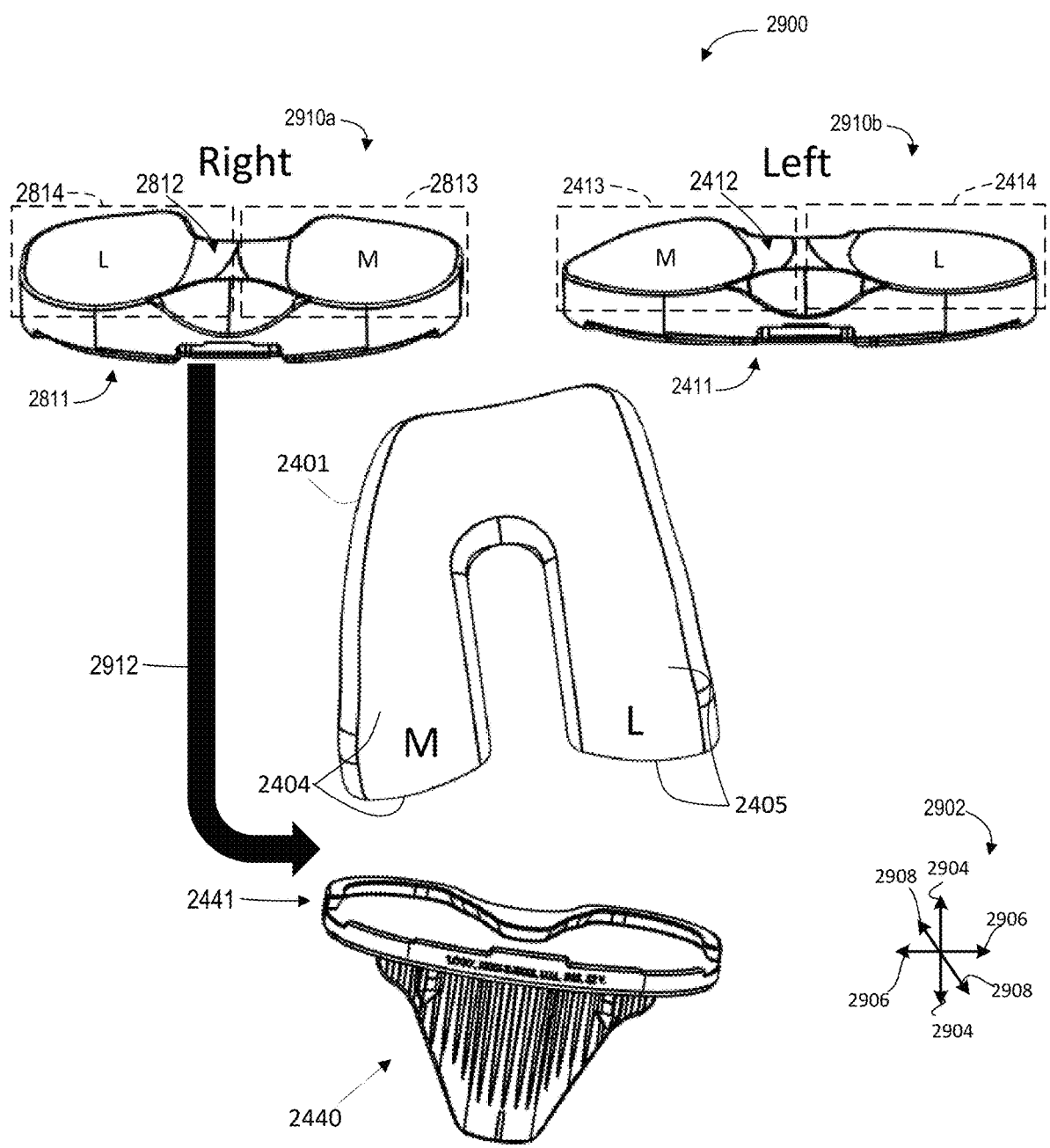
FIG. 30 is a perspective anterior view of knee prosthesis system according to another embodiment of the present disclosure.

FIG. 30 is a perspective anterior view of knee prosthesis system according to another embodiment of the present disclosure. FIG. 30 includes similar components, parts, devices, apparatus, features, and aspects as those disclosed and described in relation to FIG. 29, however the difference in FIG. 30 is that the knee prosthesis system 2900 is to be deployed in a knee joint having a different condition than a knee joint in relation to the knee prosthesis system 2900 of FIG. 29. In FIG. 30, the example knee prosthesis system 2900 is to be deployed in a knee joint having a valgus condition As used herein, a "valgus condition" refers to a state of a bone or joint having an undesired outward angulation (angled laterally, away from the body's midline) of the distal segment of a bone or joint. For example in a valgus condition of the knee, the distal part of the leg below the knee is deviated outward, in relation to the femur, resulting in a knock-kneed appearance. The opposite of varus is called valgus. A varus condition at the knee results in a bowlegged appearance with the distal part of the leg deviated inward, in relation to the femur. (Search "valgus deformity" on Wikipedia.com Oct. 20, 2020. Modified. Accessed Jan. 6, 2020.) A valgus condition can be experienced in a variety of joints, including but not limited to, ankle joints, elbow joints, foot joints, hand joints, hip joints, knee joints, toe joints, wrist joints, and the like. A knee that has a valgus condition may also be referred to as a valgus knee.

A patient knee with a valgus condition may cause one or more problems or challenges in the kinematics of the knee as the knee transitions through various angles of flexion and/or extension. For example, a valgus knee may have impeded, or unnatural, tibiofemoral rotation within the medial tibial compartment during flexion of the knee joint. The impeded, or unnatural, tibiofemoral rotation may cause premature wear on components of the knee prosthesis system 2900, interfere with a patient's balance, interfere with the patient's gait or mobility, or the like.

Advantageously, the knee prosthesis system 3000 can remediate an undesirable or unacceptable tibiofemoral rotation within the medial tibial compartment during flexion of the knee joint. Specifically, the tibial articulation surface 2812 facilitates tibiofemoral rotation within the medial tibial compartment 2813 during flexion of a first knee joint where the condition is a R valgus knee joint. In the illustrated embodiment, the surgeon may choose, either pre-operatively and/or intraoperatively, to use tibial insert 2910*b* with the tibial baseplate component 2840 and the femoral component 2801 for a right knee. The tibial insert 2910*b* is positioned between the tibial baseplate component 2840 and the femoral component 2801 when deployed, see arrow 3012. The tibial insert 2910*b* may be used instead of the tibial insert 2910*a* because the right knee presents a valgus condition.

The tibial insert 2910*b* includes a tibial articulation surface 2412 having a medial tibial compartment 2413 and a lateral tibial compartment 2414. The compatible interfaces 2411, 2841 enable the surgeon to deploy the tibial insert 2910*b* with the tibial baseplate component 2840 and the femoral component 2801 for a right knee to adapt, adjust, refine, or modify kinematics of a patient's right knee joint having a valgus condition.

Figure 32:
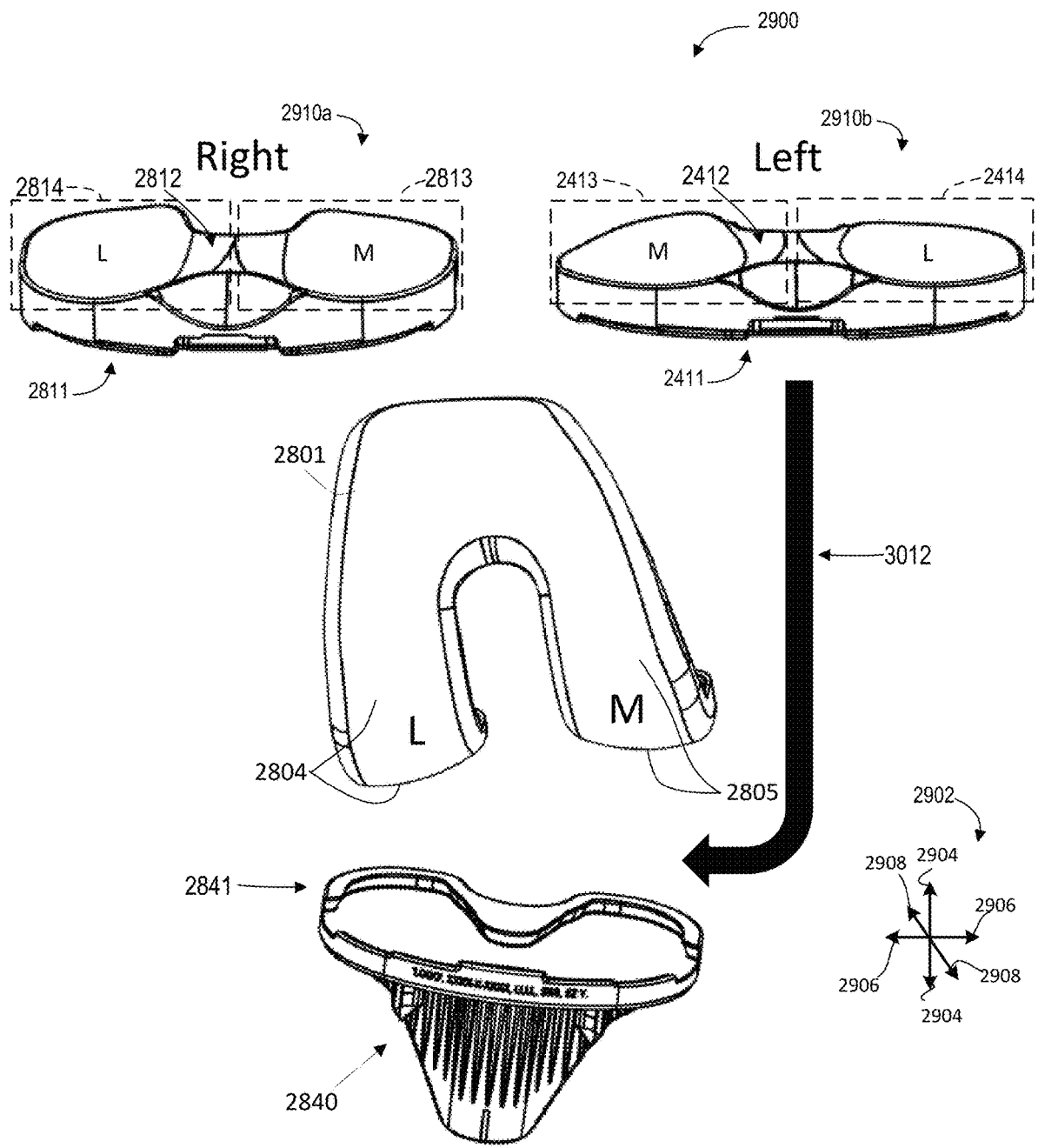
FIG. 32 is a perspective anterior view of knee prosthesis system according to another embodiment of the present disclosure.

It should be noted that in the illustrated embodiment a surgeon may deploy the tibial insert 2910*b* in a right knee because the knee has a valgus condition. However, the tibial insert 2910*b* may also be deployed (e.g., is suitable for implantation) in a patient's left knee joint that lacks the valgus condition. While the tibial insert 2910*b* may be designed for deployment in a left knee joint that lacks a condition, or has a balanced condition, the tibial insert 2910*b* is illustrated in FIG. 32 being deployed in a right knee joint that has a valgus condition of about eight degrees. Referring still to FIG. 30, with a knee joint having a valgus condition, a surgeon may decide to couple, or connect, the tibial insert 2910*a* to the tibial baseplate component 2440.

Figure 31:
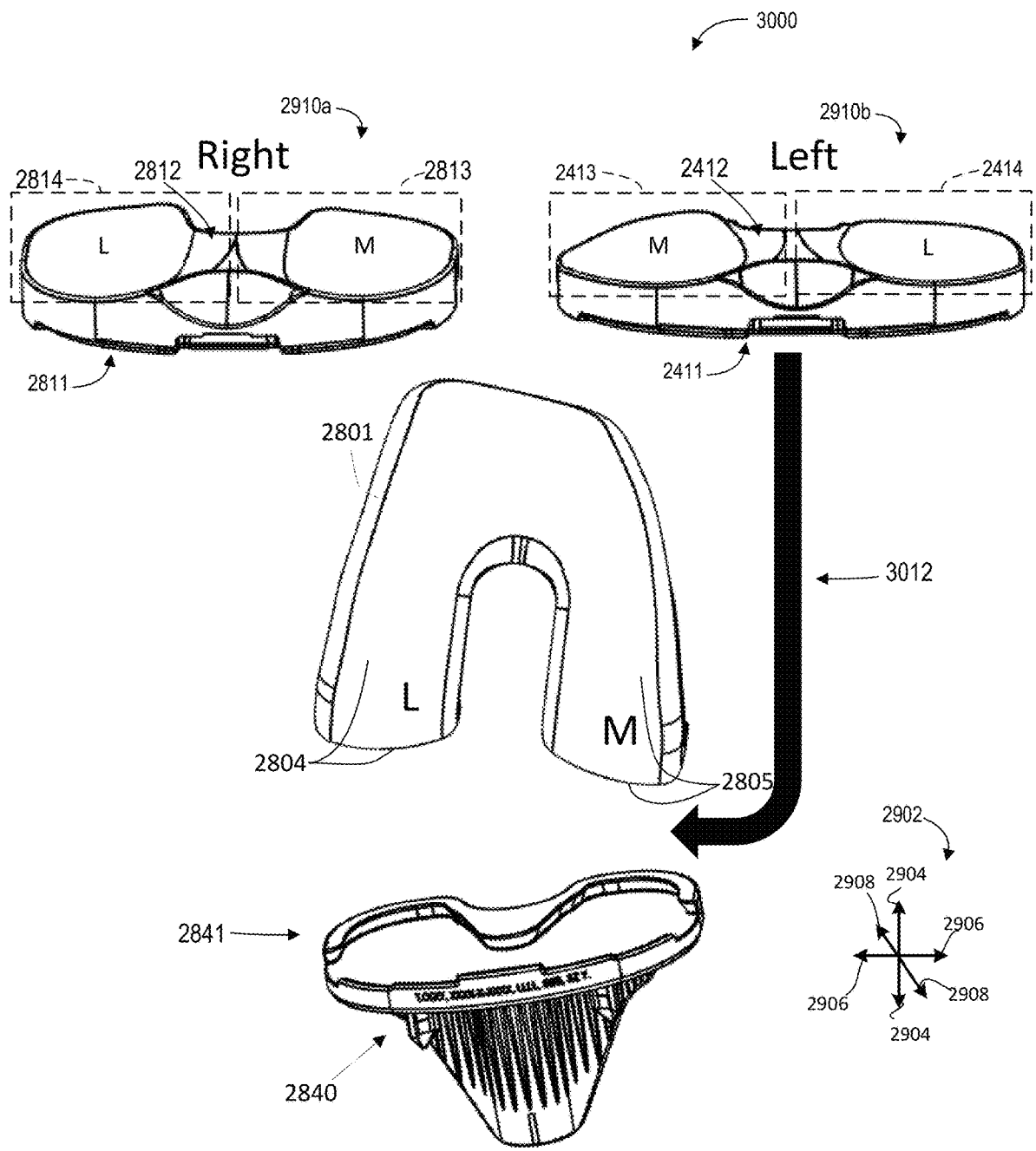
FIG. 31 is a perspective anterior view of knee prosthesis system according to one embodiment of the present disclosure.

FIG. 31 is a perspective anterior view of knee prosthesis system according to one embodiment of the present disclosure. The knee prosthesis system 3000 includes a femoral component, an insert, and a tibial baseplate component. In certain embodiments, a particular femoral component and a particular tibial baseplate component are specifically configured for a right knee joint. In certain embodiments, a particular femoral component and a particular tibial baseplate component are specifically configured for a left knee joint. Alternatively, or in addition, the femoral component and tibial baseplate component may be specifically configured for use in either one of a left knee joint or a right knee joint. A knee prosthesis system 3000 for the right knee joint may be configured for a first side of a patient. Alternatively, or in addition, a knee prosthesis system for the left knee joint may be configured for a second side of a patient, the second side being the other side of the right side and the left side.

In the illustrated embodiment, the femoral component is the femoral component 2801 for a right knee (See FIG. 28A) and the tibial baseplate component is the tibial baseplate component 2840 for a right knee. The tibial baseplate component 2840 includes an insert interface 2841. The femoral component 2801 includes a femoral articulation surface that includes one, or both of, the medial condylar articulation surface 2804 and the lateral condylar articulation surface 2805.

FIG. 31 illustrates the orientation and configuration of the femoral component 2801 and tibial baseplate component 2840 for a right knee of a patient where the right knee has a condition. In the illustrated embodiment, the right knee of a patient has a varus condition with the knee joint angled about eight degrees away from a vertical axis, such as the cephalad-caudal axis 2904. The patient may have two knees, each having a knee joint, such as a right knee of a first knee joint, on a first side of the patient and a second knee, such as a left knee of a second knee joint, on a second side of the patient. The tibial insert 2910b deployed in the knee prosthesis system 3000 is configured for a left knee joint and attached to the insert interface 2841 of the tibial baseplate component 2840 of the right knee joint. In such an implementation, another tibial insert may be configured for the right knee joint of the patient, for example tibial insert 2910a.

A patient knee with a varus condition may cause one or more problems or challenges in the kinematics of the knee as the knee transitions through various angles of flexion and/or extension. For example, a varus knee may have undesirable stability (insufficient stability) during flexion. This undesired instability may be caused by a gap imbalance between the medial and lateral condyles of the femoral component 2801 (or the distal end of the femur). Such instability is referred to as mediolateral stability. The insufficient or undesirable level of mediolateral stability during flexion may cause anxiety for the patient during flexion and reduced confidence in the integrity and performance of the knee prosthesis system 3000.

Advantageously, the knee prosthesis system 3000 can remediate an undesirable level of mediolateral stability based on a tibial insert used by the surgeon when deploying the knee prosthesis system 3000. In the illustrated embodiment, the surgeon may choose, either pre-operatively and/or intraoperatively, to use tibial insert 2910b with the tibial baseplate component 2840 and the femoral component 2801 for a right knee. The tibial insert 2910b is positioned between the tibial baseplate component 2840 and the femoral component 2801 when deployed, see arrow 3012.

The tibial insert 2910b includes a tibial articulation surface 2412 having a medial tibial compartment 2413 and a lateral tibial compartment 2414. The tibial insert 2910a includes a tibial articulation surface 2412 having medial tibial compartment 2413 and a lateral tibial compartment 2414. Advantageously, in one embodiment, the baseplate interface 2411 of the tibial insert 2910b is complementary to, and/or compatible with, the insert interface 2841 of the tibial baseplate component 2840. The baseplate interface 2811 of the tibial insert 2910a is also complementary to, and/or compatible with, the insert interface 2841 of the tibial baseplate component 2840. The compatible interfaces 2411, 2841 enable the surgeon to deploy the tibial insert 2910b with the tibial baseplate component 2840 and the femoral component 2801 for a right knee to adapt, adjust, refine, or modify kinematics of a patient's left knee joint having a condition. The tibial articulation surface 2412 is shaped to cooperate with the femoral articulation surface to adapt kinematics of a knee joint having a condition. In the illustrated embodiment, the condition is a varus condition, the condition can also be one of a valgus condition and a balanced condition.

In one embodiment, the tibial articulation surface 2412 is configured to include one or more of a medial tibial compartment 2413, a lateral tibial compartment 2414, a medial articulation surface 2420, a lateral articulation surface 2421, and/or high and/or low points within the medial articulation surface 2420, and/or the lateral articulation surface 2421 to remediate a condition of the knee joint into which the knee prosthesis system 3000 deployed. In one embodiment, the tibial articulation surface 2412 contour and/or features adjust mediolateral stability during flexion of a first knee joint having a varus condition: is a varus knee joint. In one embodiment, a tibial articulation surface 2412 of the tibial insert 2910b may adjust mediolateral stability by increasing constraint on a lateral collateral ligament of the first knee joint and decreases tension on a medial collateral ligament of the first knee joint.

It should be noted that in the illustrated embodiment a surgeon may deploy the tibial insert 2910b in a right knee because the knee has a condition. However, the tibial insert 2910b may also be deployed (e.g., is suitable for implantation) in a patient's left knee joint that lacks the condition. While the tibial insert 2910b may be designed for deployment in a left knee joint that lacks a condition, or has a balanced condition, the tibial insert 2910b is illustrated in FIG. 31 being deployed in a right knee joint that has a varus condition of about eight degrees.

In one embodiment, the femoral component 2801 is configured for a first side of a patient and the tibial insert 2910b is configured for the second side of the patient. In the illustrated embodiment, the first side may be a right side of a patient and the second side may be a left side of a patient. Alternatively, or in addition, the first side may be a left side of a patient and the second side may be a right side of a patient.

Referring still to FIG. 31, with a knee joint having a varus condition, a surgeon may decide to couple, or connect, the tibial insert 2910b to the tibial baseplate component 2840. As the surgical procedure is completed, a patient's knee joint, such as a right knee joint, includes the femoral component 2801 having a medial femoral compartment that includes the medial condylar articulation surface 2804 and a lateral femoral compartment that includes the lateral condylar articulation surface 2805. In the illustrated embodiment, the medial condylar articulation surface 2804 defines the medial femoral compartment and the lateral condylar articulation surface 2805 defines the lateral femoral compartment. The tibial insert 2910b may be used instead of the tibial insert 2910a because the left knee presents a varus condition.

With the tibial insert 2910b deployed in the knee joint, the medial tibial compartment 2413 engages the lateral femoral compartment at a lateral dwell point (shown in later figures) during flexion and the lateral tibial compartment 2414 engages the medial femoral compartment at a medial dwell point (shown in later figures) during flexion. Those of skill in the art will recognize that this is different from the arrangement should the tibial insert 2910a be deployed between the femoral component 2801 and the tibial baseplate component 2840. Said another way, if the left tibial insert 2910a were deployed in a right knee joint, the medial compartments of each of the femoral component 2801 and the tibial baseplate component 2840 would engage with each other and the lateral compartments of each of the femoral component 2801 and the tibial baseplate component 2840 would engage with each other.

FIG. 32 is a perspective anterior view of knee prosthesis system according to another embodiment of the present disclosure. FIG. 32 includes similar components, parts, devices, apparatus, features, and aspects as those disclosed and described in relation to FIG. 31, however the difference in FIG. 32 is that the knee prosthesis system 3000 is to be deployed in a knee joint having a different condition than a knee joint in relation to the knee prosthesis system 3000 of FIG. 31. In FIG. 32, the example knee prosthesis system 3000 is to be deployed in a right knee joint having a valgus condition.

FIG. 32 illustrates the orientation and configuration of the femoral component 2801 and tibial baseplate component 2840 for a right knee of a patient where the right knee has a condition. In the illustrated embodiment, the right knee of a patient has a valgus condition with the knee joint angled about eight degrees away from a vertical axis, such as the cephalad-caudal axis 2904. The patient may have two knees, each having a knee joint, such as a right knee of a first knee joint, on a first side of the patient and a second knee, such as a left knee of a second knee joint, on a second side of the patient. The tibial insert 2910b deployed in the knee prosthesis system 3000 is configured for a left knee joint and attached to the insert interface 2841 of the tibial baseplate component 2840 of the right knee joint. In such an implementation, another tibial insert may be configured for the right knee joint of the patient, for example tibial insert 2910a.

A patient knee with a valgus condition may cause one or more problems or challenges in the kinematics of the knee as the knee transitions through various angles of flexion and/or extension. For example, a valgus knee may have impeded, or unnatural, tibiofemoral rotation within the medial tibial compartment during flexion of the knee joint. The impeded, or unnatural, tibiofemoral rotation may cause premature wear on components of the knee prosthesis system 3000, interfere with a patient's balance, interfere with the patient's gait or mobility, or the like.

Advantageously, the knee prosthesis system 3000 can remediate an undesirable or unacceptable tibiofemoral rotation within the medial tibial compartment during flexion of the knee joint. Specifically, the tibial articulation surface 2412 facilitates tibiofemoral rotation within the medial tibial compartment 2413 during flexion of a first knee joint where the condition is a R valgus knee joint. In the illustrated embodiment, the surgeon may choose, either pre-operatively and/or intraoperatively, to use tibial insert 2910b with the tibial baseplate component 2840 and the femoral component 2801 for a right knee. The tibial insert 2910b is positioned between the tibial baseplate component 2840 and the femoral component 2801 when deployed, see arrow 3012. The tibial insert 2910b may be used instead of the tibial insert 2910a because the right knee presents a valgus condition.

The tibial insert 2910b includes a tibial articulation surface 2412 having a medial tibial compartment 2413 and a lateral tibial compartment 2414. The compatible interfaces 2411, 2841 enable the surgeon to deploy the tibial insert 2910b with the tibial baseplate component 2840 and the femoral component 2801 for a right knee to adapt, adjust, refine, or modify kinematics of a patient's right knee joint having a valgus condition.

It should be noted that in the illustrated embodiment a surgeon may deploy the tibial insert 2910b in a right knee because the knee has a valgus condition. However, the tibial insert 2910b may also be deployed (e.g., is suitable for implantation) in a patient's left knee joint that lacks the valgus condition. While the tibial insert 2910b may be designed for deployment in a left knee joint that lacks a condition, or has a balanced condition, the tibial insert 2910b is illustrated in FIG. 32 being deployed in a right knee joint that has a valgus condition of about eight degrees. Referring still to FIG. 32, with a knee joint having a valgus condition, a surgeon may decide to couple, or connect, the tibial insert 2910b to the tibial baseplate component 2840.

Those of skill in the art will appreciate that the tibial insert 2910a and/or tibial insert 2910b used with the present disclosure may be tibial inserts configured to a variety of different knee prosthesis systems. For example, the tibial inserts 2910a,b may be one or more of a cruciate retaining tibial insert, a constrained condylar knee tibial insert, a posterior stabilizing tibial insert, and a medially-laterally asymmetric tibial insert. As used herein, "cruciate retaining tibial insert" refers to a tibial insert configured for use with a cruciate retaining ("CR") prosthesis. As used herein, "constrained condylar knee tibial insert" refers to a tibial insert configured for use with a constrained condylar knee ("CCK") prosthesis. As used herein, "posterior stabilizing tibial insert" refers to a tibial insert configured for use with a posterior stabilizing ("PS") prosthesis. As used herein, "medially-laterally asymmetric tibial insert" refers to a tibial insert configured for use with a prosthesis that uses medially-laterally asymmetric articular surfaces on at least one component of the prosthesis.

Figure 33A:
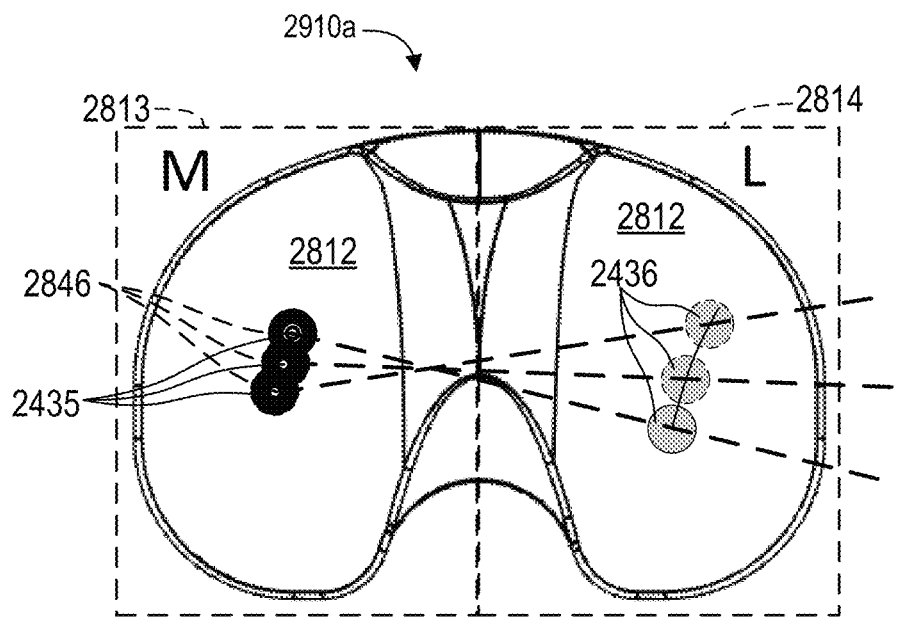
FIG. 33A is a top view of right side tibial insert according to one embodiment of the present disclosure.

FIG. 33A is a top view of right side tibial insert, such as tibial insert 2910a, according to one embodiment of the present disclosure. FIGS. 29 and 30 illustrate that using the tibial insert 2910a with a femoral component 2401 and tibial baseplate component 2440 of a left knee results in the medial tibial compartment 2813 engaging with the lateral condylar articulation surface 2405 (also referred to as the lateral femoral compartment) at a lateral dwell point 2436 and the lateral tibial compartment 2814 engaging with the medial condylar articulation surface 2404 (also referred to as the medial femoral compartment) at a medial dwell point 2435. In certain embodiments, the lateral femoral compartment and medial femoral compartment are symmetrical such that translation and/or rotation of the tibial articulation surface 2812 and lateral condylar articulation surface 2405 and medial condylar articulation surface 2404 is managed by the contour of the tibial articulation surface 2812.

FIG. 33A illustrates positions for the medial dwell point 2435 and lateral dwell point 2436 during flexion of a joint that includes the tibial insert 2910a with a femoral component 2401 and tibial baseplate component 2440 of a left knee. The medial dwell point 2435 and lateral dwell point 2436 translate and/or rotate during flexion. Due, at least in part, to the contour of the tibial articulation surface 2812, the lateral dwell point 2436 migrates anteriorly and outwardly and the medial dwell point 2435 migrates posteriorly and outwardly. In certain embodiments, this migration of the dwell points facilitates tibiofemoral rotation within the medial tibial compartment 2813 during flexion of the knee joint where the condition is a valgus knee joint and/or adjusts mediolateral stability during flexion of the knee joint where the condition is a varus knee joint. In one embodiment, the tibial articulation surface 2812 may increases constraint on a lateral collateral ligament of the knee joint and decreases tension on a medial collateral ligament of the knee joint.

Figure 33B:
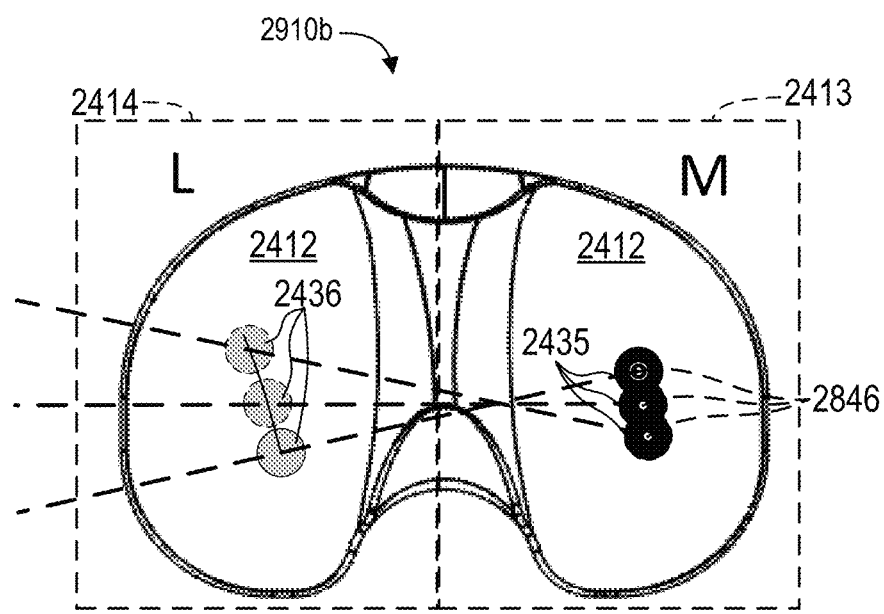
FIG. 33B is a top view of left side tibial insert according to one embodiment of the present disclosure.

FIG. 33B is a top view of right side tibial insert, such as tibial insert 2910b, according to one embodiment of the present disclosure. FIGS. 31 and 32 illustrate that using the tibial insert 2910b with a femoral component 2801 and tibial baseplate component 2840 of a right knee results in the medial tibial compartment 2413 engaging with the lateral condylar articulation R surface 2805 (also referred to as the lateral femoral compartment) at a lateral dwell point 2436 and the lateral tibial compartment 2414 engaging with the medial condylar articulation surface 2804 (also referred to as the medial femoral compartment) at a medial dwell point 2435. In certain embodiments, the lateral femoral compartment and medial femoral compartment are symmetrical such that translation and/or rotation of the tibial articulation surface 2412 and lateral condylar articulation surface 2805 and medial condylar articulation surface 2804 is managed by the contour of the tibial articulation surface 2412.

FIG. 33B illustrates positions for the medial dwell point 2435 and lateral dwell point 2436 during flexion of a joint that includes the tibial insert 2910b with a femoral component 2801 and tibial baseplate component 2840 of a right knee. The medial dwell point 2435 and lateral dwell point 2436 translate and/or rotate during flexion. Due, at least in part, to the contour of the tibial articulation surface 2412, the lateral dwell point 2436 migrates anteriorly and outwardly and the medial dwell point 2435 migrates posteriorly and outwardly. In certain embodiments, this migration of the dwell points facilitates tibiofemoral rotation within the medial tibial compartment 2413 during flexion of the knee joint where the condition is a valgus knee joint and/or adjusts mediolateral stability during flexion of the knee joint where the condition is a varus knee joint. In one embodiment, the tibial articulation surface 2412 may increases constraint on a lateral collateral ligament of the knee joint and decreases tension on a medial collateral ligament of the knee joint.

Referring still to FIG. 33B, in certain embodiments, the knee joint is a right knee joint of a patient. A left side tibial insert 2910b is attached to the insert interface 2841 of the tibial baseplate component 2840 of the right knee joint such that the left side tibial insert 2910b constrains the femoral articulation surface within the medial tibial compartment 2413 and mitigates the condition.

Figure 34:
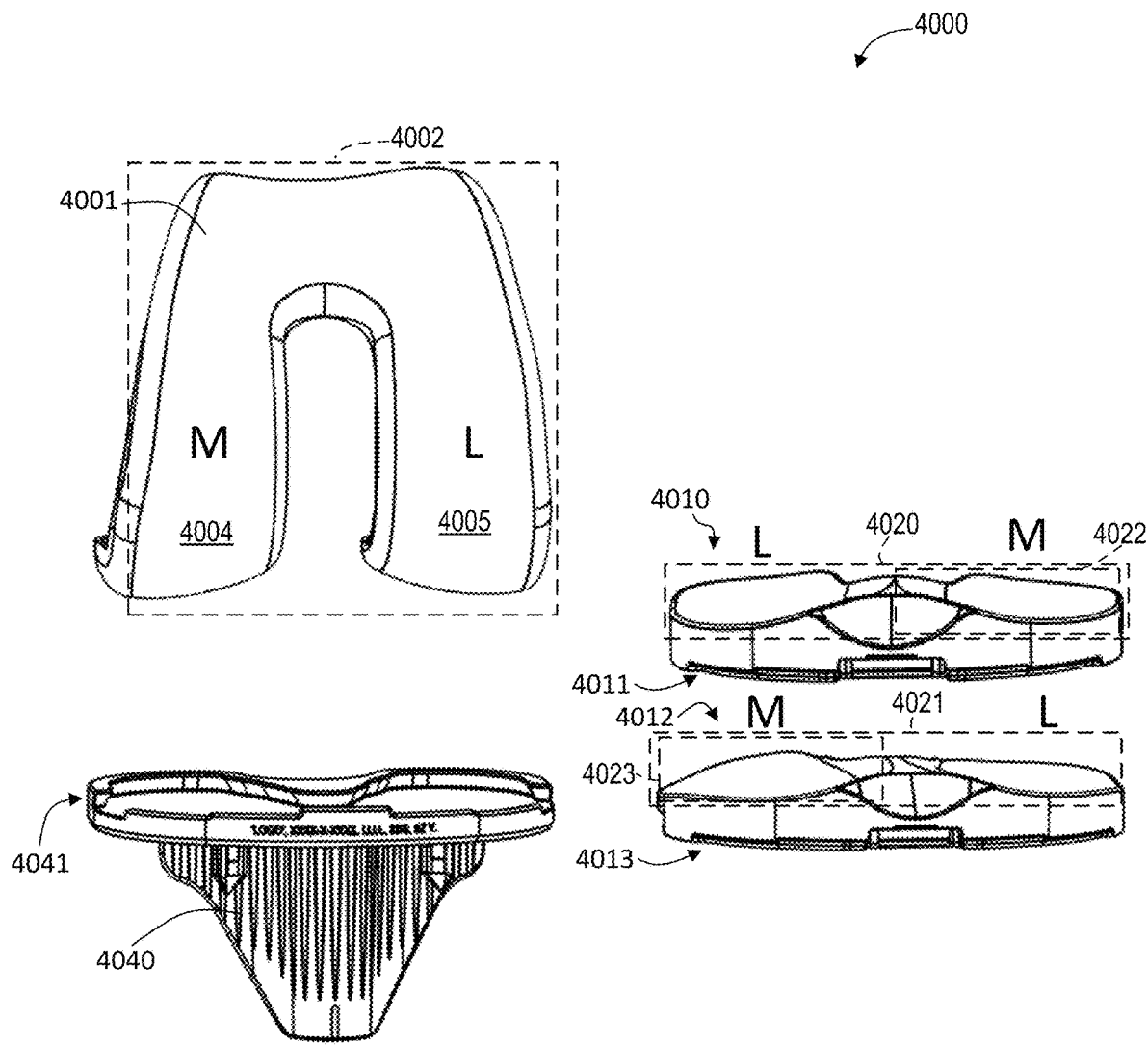
FIG. 34 is a perspective anterior view of knee prosthesis system according to another embodiment of the present disclosure.

FIG. 34 is a perspective anterior view of knee prosthesis system 4000 according to another embodiment of the present disclosure. The knee prosthesis system 4000 is configured for use in a knee joint of a patient. The same knee prosthesis system 4000 can be used in a knee joint with a condition as well as in the same knee joint that lacks the condition. Advantageously, such a knee prosthesis system 4000 reduces the inventory needed to perform knee joint arthroplasty. In one embodiment, the knee prosthesis system 4000 includes a femoral component 4001, a tibial baseplate component 4040, a right tibial insert 4010, and a left tibial insert 4012.

In the illustrated embodiment, the femoral component 4001 and tibial baseplate component 4040 may be very similar to the like named components in the other embodiments disclosed herein. In one embodiment, the same femoral component 4001 and tibial baseplate component 4040 may be configured for use in either a right knee joint or a left knee joint of a patient. Alternatively, or in addition, the femoral component 4001 and/or tibial baseplate component 4040 may be specifically designed for a left knee joint or a right knee joint. By way of example, suppose the knee prosthesis system 4000 is to be deployed on a left knee of a patient (medial and lateral sides identified on the femoral component 4001 by an "M" and an "L").

The femoral component 4001 is configured to be implanted on a femur of a patient for a first knee joint, the femoral component 4001 comprising a femoral articulation surface 4002 that includes a medial condylar articulation surface 4004 and a lateral condylar articulation surface 4005. The tibial baseplate component 4040 is configured to be implanted on a tibia for the first knee joint of a patient. The tibial baseplate component 4040 includes an insert interface 4041.

The right side tibial insert 4010 is configured to attach to the insert interface 4041 of the tibial baseplate component 4040. In one embodiment, the right side tibial insert 4010 may include an interface 4011 that is compatible with the insert interface 4041. The right side tibial insert 4010 also includes a tibial articulation surface 4020. If the right side tibial insert 4010 is installed between the femoral component 4001 and the tibial baseplate component 4040, the tibial articulation surface 4020 articulates with the femoral articulation surface 4002 and rotates the tibia about a longitudinal axis of the tibia passing through a medial tibial compartment 4022 of the right side tibial insert 4010 during flexion or extension of a right side knee joint.

The left side tibial insert 4012 is configured to attach to the insert interface 4041 of the tibial baseplate component 4040. In one embodiment, the left side tibial insert 4012 may include an interface 4013 that is compatible with the insert interface 4041. The left side tibial R insert 4012 also includes a tibial articulation surface 4021. If the left side tibial insert 4012 is installed between the femoral component 4001 and the tibial baseplate component 4040, the tibial articulation surface 4021 articulates with the femoral articulation surface 4002 and rotates the tibia about a longitudinal axis of the tibia passing through a medial tibial compartment 4023 of the left side tibial insert 4010 during flexion or extension of a left side knee joint.

The tibial articulation surface 4020 of the right side tibial insert 4010 is shaped to cooperate with the femoral articulation surface 4002 to change kinematics of a knee joint having the condition if the knee joint is the left side knee joint. The tibial articulation surface 4021 of the left side tibial insert 4012 is shaped to cooperate with the femoral articulation surface 4002 to change kinematics of the knee joint having the condition if the knee joint is the right side knee joint. Advantageously, a surgeon using the knee prosthesis system 4000 can determine intraoperatively whether to use the right side tibial insert 4010 (e.g., if the knee joint has a varus or valgus condition) or the left side tibial insert 4012 (e.g., if the knee joint lacks a varus or valgus condition or has a balanced condition). The knee joint may present with a varus condition, a valgus condition, or a balanced condition. As used herein, a "balanced condition" refers to a state of a bone and/or joint having a desired alignment of the bone or joint with a central axis of a limb or anatomical structure that includes the bone and/or joint. In certain embodiments, a balanced condition refers to a condition of the bone or joint that is not a varus condition and is not a valgus condition.

Referring to FIG. 34, in one embodiment, the knee prosthesis system may include the femoral component 4001 and a right side tibial component and a left side tibial component. A right side tibial component may be a single unitary component that includes the features, functions, attributes, and aspects of both the tibial baseplate component 4040 and the right side tibial insert 4010 combined into a single component. A left side tibial component may be a single unitary component that includes the features, functions, attributes, and aspects of both the tibial baseplate component 4040 (e.g., for example a copy of tibial baseplate component 4040 not shown) and the left side tibial insert 4012 combined into a single component. Those of skill in the art will appreciate that the features, functions, and advantages of a right side tibial insert 4010 that is connected to the tibial baseplate component 4040 and the that the features, functions, and advantages of a left side tibial insert 4012 that is connected to the tibial baseplate component 4040 would be included with a right side tibial component and a left side tibial component, respectively. One potential advantage of using a right side tibial component and a left side tibial component may be that there are fewer parts in the knee prosthesis system.

Figure 35:
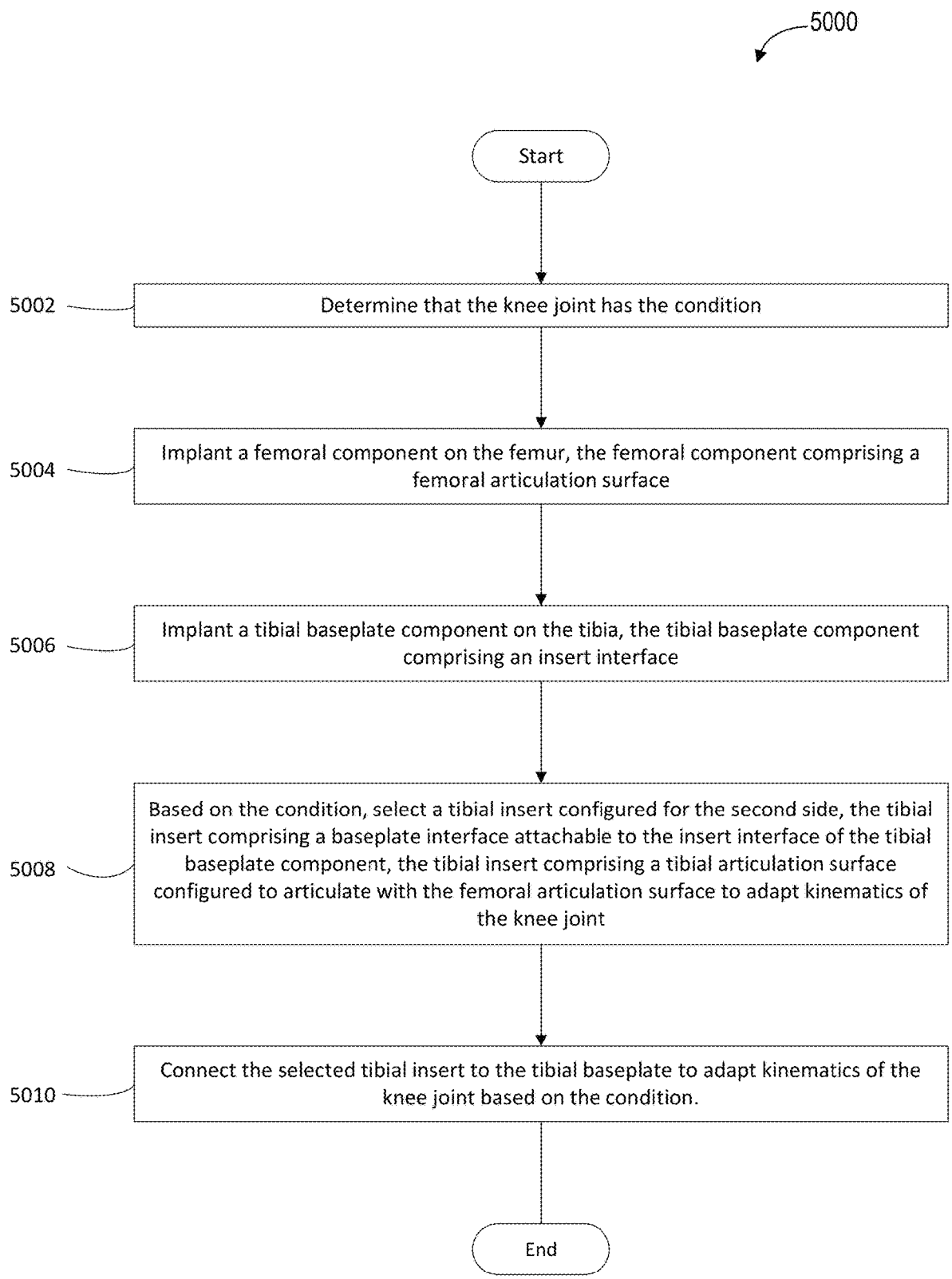
FIG. 35 is a flow chart diagram of one example method for adapting kinematics of a knee joint having a condition.

FIG. 35 illustrates of one example method 5000 for adapting kinematics of a knee joint having a condition. Referring to FIGS. 24A through 34, the method 5000 starts with a user, such as a surgeon, determining 5002 that a knee joint of a patient has a condition. This determination may be made based on an observation of the patient, medical imaging scans, or the like. Furthermore, the determination may be made by a user either before or during a surgical procedure in relation to the knee joint.

Next, a surgeon, or other user, may implant 5004 a femoral component on a femur of the knee joint of the patient. The femoral component may include a femoral articulation surface. Next, a surgeon, or other user, may implant 5006 a tibial baseplate component on a tibia of the knee joint of the patient. The tibial baseplate component may include an insert interface.

Next, based on a condition present in the knee joint, a surgeon, or other user, may select 5008 a tibial insert configured for the second side (a side of a patient other than the side that includes the knee joint). The selected tibial insert includes a baseplate interface attachable to the insert interface of the tibial baseplate component. The selected tibial insert also includes a tibial articulation surface configured to articulate with the femoral articulation surface to adapt kinematics of the knee joint.

Next, a surgeon, or other user, may connect 5010 the selected tibial insert to the tibial baseplate to adapt kinematics of the knee joint based on the condition and the method 5000 ends.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects can exist in a combination of fewer than all features, components, aspects, parts, and/or structures of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" may refer to a location on the device that is closest to the clinician using the device and farthest from the patient in connection with whom the device is used when the device is used in its normal operation. Conversely, the term "distal", "bottom", "down" or "downwardly" may refer to a location on the device that is farthest from the clinician using the device and closest to the patient in connection with whom the device is used when the device is used in its normal operation. Moreover, the terms "upper" and "lower", and "top" and "bottom", "front" and "rear" may be used as relative terms herein for ease of description and understanding. It is understood that in embodiments of the disclosure, upper and lower entities may be reversed, as may top and bottom, front and rear.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

What is claimed is:

1. A knee joint prosthesis system for implantation in a first knee joint of a patient, the first knee joint comprising a femur and a tibia, the first knee joint having a condition, wherein the first knee joint is on a first side of the patient, selected from a right side and a left side, and is not on a second side of the patient, the second side comprising the other of the right side and the left side, the knee joint prosthesis system comprising:
a tibial baseplate component configured to be implanted on the tibia, the tibial baseplate component comprising an insert interface;
a femoral component configured to be implanted on the femur, the femoral component comprising a femoral articulation surface; and
a tibial insert comprising a baseplate interface attachable to the insert interface of the tibial baseplate component, the tibial insert comprising a tibial articulation surface configured to articulate with the femoral articulation surface;
wherein:
the tibial articulation surface comprises a medial tibial compartment and a lateral tibial compartment that is asymmetrical to the medial tibial compartment;
the tibial articulation surface is shaped to cooperate with the femoral articulation surface to adapt kinematics of the first knee joint having the condition;
the tibial articulation surface is suitable for implantation in a second knee joint on the second side, the second knee joint lacking the condition; and
one of the following is true:
the tibial articulation surface facilitates tibiofemoral rotation within the medial tibial compartment during flexion of the first knee joint where the condition is a valgus knee joint; and
the tibial articulation surface adjusts mediolateral stability during flexion of the first knee joint where the condition is a varus knee joint.

2. The knee joint prosthesis system of claim 1, wherein the femoral component is configured for the first side and the tibial insert is configured for the second side of the patient.

3. The knee joint prosthesis system of claim 1, wherein:
the first knee joint is a right knee joint of the patient;
the second knee joint is a left knee joint of the patient; and
wherein
the tibial insert is configured for the left knee joint and attached to the insert interface of the tibial baseplate component of the right knee joint; and
another tibial insert is configured for the right knee joint.

4. The knee joint prosthesis system of claim 1, wherein the tibial articulation surface is configured to facilitate tibiofemoral rotation within the medial tibial compartment during flexion of the first knee joint where the condition is a valgus knee joint.

5. The knee joint prosthesis system of claim 1, wherein the tibial articulation surface is configured to adjust mediolateral stability during flexion of the first knee joint where the condition is a varus knee joint.

6. The knee joint prosthesis system of claim 5, wherein the tibial articulation surface is configured to increase constraint on a lateral collateral ligament of the first knee joint and decreases tension on a medial collateral ligament of the first knee joint.

7. The knee joint prosthesis system of claim 1, wherein the medial tibial compartment comprises a medial perimeter, a medial high point, and a medial low point and wherein the lateral tibial compartment comprises a lateral perimeter, a lateral high point, and a lateral low point.

8. The knee joint prosthesis system of claim 1, wherein the femoral articulation surface comprises a medial femoral compartment and a lateral femoral compartment and wherein the medial tibial compartment engages the lateral femoral compartment at a lateral dwell point during flexion and the lateral tibial compartment engages the medial femoral compartment at a medial dwell point during flexion.

9. The knee joint prosthesis system of claim 8, wherein, the lateral dwell point migrates anteriorly and outwardly and the medial dwell point migrates posteriorly and outwardly.

10. The knee joint prosthesis system of claim 8, wherein the medial femoral compartment and the lateral femoral compartment are symmetrical.

11. The knee joint prosthesis system of claim 1, wherein the tibial insert comprises one of a cruciate retaining tibial insert, a constrained condylar knee tibial insert, a posterior stabilizing tibial insert, and a medially-laterally asymmetric tibial insert and wherein the condition comprises one of a varus condition and a valgus condition.

12. A knee joint prosthesis system for implantation in a knee joint of a patient, the knee joint comprising a femur and a tibia, the knee joint having a condition, wherein the knee joint is on a first side of the patient, selected from a right side and a left side, and is not on a second side of the patient, the second side comprising the other of the right side and the left side, the knee joint prosthesis system comprising:
a tibial baseplate component configured to be implanted on the tibia, the tibial baseplate component comprising an insert interface;
a femoral component configured to be implanted on the femur, the femoral component comprising a femoral articulation surface;
a right side tibial insert attachable to the insert interface of the tibial baseplate component, the right side tibial insert comprising a tibial articulation surface configured to articulate with the femoral articulation surface and rotate the tibia about a longitudinal axis of the tibia passing through a medial tibial compartment of the right side tibial insert during flexion or extension of a right side knee joint;

a left side tibial insert attachable to the insert interface of the tibial baseplate component, the left side tibial insert comprising a tibial articulation surface configured to articulate with the femoral articulation surface and rotate the tibia about the longitudinal axis passing through a medial tibial compartment of the left side tibial insert during flexion or extension of a left side knee joint; and wherein:
the tibial articulation surface of the right side tibial insert is shaped to cooperate with the femoral articulation surface to change kinematics of the knee joint having the condition if the knee joint comprises the left side knee joint; and the tibial articulation surface of the left side tibial insert is shaped to cooperate with the femoral articulation surface to change kinematics of the knee joint having the condition if the knee joint comprises the right side knee joint.

13. The knee joint prosthesis system of claim 12, wherein:
the knee joint is a right knee joint of the patient; and
wherein the left side tibial insert is attached to the insert interface of the tibial baseplate component of the right knee joint such that the left side tibial insert constrains the femoral articulation surface within the medial tibial compartment and mitigates the condition.

14. The knee joint prosthesis system of claim 12, wherein the tibial articulation surface facilitates tibiofemoral rotation within the medial tibial compartment during flexion of the knee joint where the condition is a valgus knee joint.

15. The knee joint prosthesis system of claim 12, wherein the tibial articulation surface adjusts mediolateral stability during flexion of the knee joint where the condition is a varus knee joint.

16. The knee joint prosthesis system of claim 15, wherein the tibial articulation surface increases constraint on a lateral collateral ligament of the knee joint and decreases tension on a medial collateral ligament of the knee joint.

17. The knee joint prosthesis system of claim 12, wherein the medial tibial compartment comprises a medial perimeter, a medial high point, and a medial low point and wherein each of the right side tibial insert and the left side tibial insert comprise a lateral tibial compartment that comprises a lateral perimeter, a lateral high point, and a lateral low point.

18. The knee joint prosthesis system of claim 12, wherein each of the right side tibial insert and the left side tibial insert comprise a lateral tibial compartment and a medial tibial compartment and wherein the femoral articulation surface comprises a medial femoral compartment and a lateral femoral compartment and wherein the medial tibial compartment engages the lateral femoral compartment at a lateral dwell point during flexion and the lateral tibial compartment engages the medial femoral compartment at a medial dwell point during flexion.

19. A method for adapting kinematics of a knee joint having a condition, the knee joint comprising a femur and a tibia, wherein the knee joint is on a first side of a patient, selected from a right side and a left side, and is not on a second side of the patient, the second side comprising the other of the right side and the left side, the method comprising:
determining that the knee joint has the condition;
implanting a femoral component on the femur, the femoral component comprising a femoral articulation surface;
implanting a tibial baseplate component on the tibia, the tibial baseplate component comprising an insert interface;
based on the condition, selecting a tibial insert configured for the second side, the tibial insert comprising a baseplate interface attachable to the insert interface of the tibial baseplate component, the tibial insert comprising a tibial articulation surface configured to articulate with the femoral articulation surface to adapt kinematics of the knee joint; and
connecting the selected tibial insert to the tibial baseplate to adapt kinematics of the knee joint based on the condition.

20. The method of claim 19, wherein condition of the knee joint comprises one of a varus condition, a valgus condition, and a balanced condition.

21. A knee joint prosthesis system for implantation in a knee joint of a patient, the knee joint comprising a femur and a tibia, the knee joint having a condition, wherein the knee joint is on a first side of the patient, selected from a right side and a left side, and is not on a second side of the patient, the second side comprising the other of the right side and the left side, the knee joint prosthesis system comprising:
a femoral component configured to be implanted on the femur, the femoral component comprising a femoral articulation surface;
a right side tibial component attachable on the tibia, the right side tibial component comprising a tibial articulation surface configured to articulate with the femoral articulation surface and rotate the tibia about a longitudinal axis passing through a medial tibial compartment of the right side tibial component during flexion or extension of a right side knee joint;
a left side tibial component attachable on the tibia, the left side tibial component comprising a tibial articulation surface configured to articulate with the femoral articulation surface and rotate the tibia about a longitudinal axis passing through a medial tibial compartment of the left side tibial component during flexion or extension of a left side knee joint; and
wherein:
the tibial articulation surface of the right side tibial component is shaped to cooperate with the femoral articulation surface to change kinematics of the knee joint having the condition if the knee joint comprises the left side knee joint; and
the tibial articulation surface of the left side tibial component is shaped to cooperate with the femoral articulation surface to change kinematics of the knee joint having the condition if the knee joint comprises the right side knee joint.

* * * * *